(12) United States Patent
Mirkin et al.

(10) Patent No.: US 9,889,209 B2
(45) Date of Patent: Feb. 13, 2018

(54) NANOCONJUGATES ABLE TO CROSS THE BLOOD-BRAIN BARRIER

(75) Inventors: Chad A. Mirkin, Wilmette, IL (US); Caroline H. Ko, Chicago, IL (US); Alexander Stegh, Chicago, IL (US); David A. Giljohann, Chicago, IL (US); Janina Luciano, Champaign, IL (US); Samuel A. Jensen, Bloomington, MN (US)

(73) Assignee: NORTHWESTERN UNIVERSITY, Evanston, IL (US)

( * ) Notice: Subject to any disclaimer, the term of this patent is extended or adjusted under 35 U.S.C. 154(b) by 0 days.

(21) Appl. No.: 14/344,576

(22) PCT Filed: Sep. 14, 2012

(86) PCT No.: PCT/US2012/055635
§ 371 (c)(1),
(2), (4) Date: Jul. 11, 2014

(87) PCT Pub. No.: WO2013/040499
PCT Pub. Date: Mar. 21, 2013

(65) Prior Publication Data
US 2015/0031745 A1    Jan. 29, 2015

Related U.S. Application Data

(60) Provisional application No. 61/534,853, filed on Sep. 14, 2011.

(51) Int. Cl.
| | | |
|---|---|---|
| *A61K 48/00* | (2006.01) | |
| *A61K 47/48* | (2006.01) | |
| *A61K 49/18* | (2006.01) | |
| *C12N 15/113* | (2010.01) | |
| *A61K 47/69* | (2017.01) | |

(52) U.S. Cl.
CPC .... *A61K 47/48861* (2013.01); *A61K 47/6923* (2017.08); *A61K 47/6929* (2017.08); *A61K 49/1851* (2013.01); *C12N 15/113* (2013.01); *C12N 2310/14* (2013.01); *C12N 2320/32* (2013.01); *C12N 2320/35* (2013.01)

(58) Field of Classification Search
CPC ....................................................... A61K 48/00
See application file for complete search history.

(56) References Cited

U.S. PATENT DOCUMENTS

| | | |
|---|---|---|
| 3,687,808 A | 8/1972 | Merigan et al. |
| 4,179,337 A | 12/1979 | Davis et al. |
| 4,289,872 A | 9/1981 | Denkewalter et al. |
| 4,301,144 A | 11/1981 | Iwashita et al. |
| 4,469,863 A | 9/1984 | Ts'o et al. |
| 4,476,301 A | 10/1984 | Imbach et al. |
| 4,489,055 A | 12/1984 | Couvreur et al. |
| 4,496,689 A | 1/1985 | Mitra |
| 4,587,044 A | 5/1986 | Miller et al. |
| 4,605,735 A | 8/1986 | Miyoshi et al. |
| 4,640,835 A | 2/1987 | Shimizu et al. |
| 4,667,025 A | 5/1987 | Miyoshi et al. |
| 4,670,417 A | 6/1987 | Iwasaki et al. |
| 4,762,779 A | 8/1988 | Snitman |
| 4,789,737 A | 12/1988 | Miyoshi et al. |
| 4,791,192 A | 12/1988 | Nakagawa et al. |
| 4,824,941 A | 4/1989 | Gordon et al. |
| 4,828,979 A | 5/1989 | Kievan et al. |
| 4,835,263 A | 5/1989 | Nguyen et al. |
| 4,845,205 A | 7/1989 | Huynh Dinh et al. |
| 4,876,335 A | 10/1989 | Yamane et al. |
| 4,904,582 A | 2/1990 | Tullis |
| 4,948,882 A | 8/1990 | Ruth |
| 4,958,013 A | 9/1990 | Letsinger |
| 4,981,957 A | 1/1991 | Lebleu et al. |
| 5,013,830 A | 5/1991 | Ohtsuka et al. |
| 5,023,243 A | 6/1991 | Tullis |
| 5,034,506 A | 7/1991 | Summerton et al. |
| 5,082,830 A | 1/1992 | Brakel et al. |
| 5,109,124 A | 4/1992 | Ramachandran et al. |
| 5,112,963 A | 5/1992 | Pieles et al. |
| 5,118,800 A | 6/1992 | Smith et al. |
| 5,118,802 A | 6/1992 | Smith et al. |
| 5,130,302 A | 7/1992 | Spielvogel et al. |
| 5,134,066 A | 7/1992 | Rogers et al. |
| 5,138,045 A | 8/1992 | Cook et al. |
| 5,149,797 A | 9/1992 | Pederson et al. |
| 5,166,315 A | 11/1992 | Summerton et al. |
| 5,175,273 A | 12/1992 | Bischofberger et al. |
| 5,177,196 A | 1/1993 | Meyer, Jr. et al. |
| 5,185,444 A | 2/1993 | Summerton et al. |
| 5,188,897 A | 2/1993 | Suhadolnik et al. |

(Continued)

FOREIGN PATENT DOCUMENTS

| | | |
|---|---|---|
| EP | 1072679 A2 | 1/2001 |
| EP | 1674128 A1 | 6/2006 |

(Continued)

OTHER PUBLICATIONS

Siegel et al. (Brain Research Reviews 33 (2000) 199-227).*
Bonoiu, et al. "Nanotechnology approach for drug additional therapy: Gene silencing using delivery of gold nanorod-siRNA nanoplex in dopaminergic neurons," PNAS 160(14):5546-5550 (2009).
Ljubimova, et al. "Nanoconjugate based on polymalic acid for tumor targeting," Chemical-Biological Interactions, 171:195-203 (2008).
Patil, et al. Temozolomide Delivery to Tumor Cells by a Maltifunctional Nano Vehicle Based on Poly(β-L-malic acid), Pharm Res 27:2317-2329 (2010).

(Continued)

*Primary Examiner* — Kimberly Chong
(74) *Attorney, Agent, or Firm* — Marshall, Gerstein & Borun LLP

(57) ABSTRACT

The present disclosure is directed to nanoconjugates that cross the blood-brain barrier and methods of their therapeutic use.

38 Claims, 7 Drawing Sheets

(56) References Cited

U.S. PATENT DOCUMENTS

| | | |
|---|---|---|
| 5,194,599 A | 3/1993 | Froehler et al. |
| 5,214,134 A | 5/1993 | Weis et al. |
| 5,214,136 A | 5/1993 | Lin et al. |
| 5,216,141 A | 6/1993 | Benner |
| 5,218,105 A | 6/1993 | Cook et al. |
| 5,220,007 A | 6/1993 | Pederson et al. |
| 5,229,490 A | 7/1993 | Tam |
| 5,235,033 A | 8/1993 | Summerton et al. |
| 5,245,022 A | 9/1993 | Weis et al. |
| 5,254,469 A | 10/1993 | Warren, III et al. |
| 5,256,775 A | 10/1993 | Froehler |
| 5,258,506 A | 11/1993 | Urdea et al. |
| 5,262,536 A | 11/1993 | Hobbs, Jr. |
| 5,264,423 A | 11/1993 | Cohen et al. |
| 5,264,562 A | 11/1993 | Matteucci |
| 5,264,564 A | 11/1993 | Matteucci |
| 5,270,163 A | 12/1993 | Gold et al. |
| 5,272,250 A | 12/1993 | Spielvogel et al. |
| 5,276,019 A | 1/1994 | Cohen et al. |
| 5,278,302 A | 1/1994 | Caruthers et al. |
| 5,286,717 A | 2/1994 | Cohen et al. |
| 5,292,873 A | 3/1994 | Rokita et al. |
| 5,317,098 A | 5/1994 | Shizuya et al. |
| 5,319,080 A | 6/1994 | Leumann |
| 5,321,131 A | 6/1994 | Agrawal et al. |
| 5,359,044 A | 10/1994 | Cook et al. |
| 5,366,878 A | 11/1994 | Pederson et al. |
| 5,367,066 A | 11/1994 | Urdea et al. |
| 5,371,241 A | 12/1994 | Brush |
| 5,391,723 A | 2/1995 | Priest |
| 5,393,878 A | 2/1995 | Leumann |
| 5,399,676 A | 3/1995 | Froehler |
| 5,403,711 A | 4/1995 | Walder et al. |
| 5,405,938 A | 4/1995 | Summerton et al. |
| 5,405,939 A | 4/1995 | Suhadolnik et al. |
| 5,414,077 A | 5/1995 | Lin et al. |
| 5,416,203 A | 5/1995 | Letsinger |
| 5,432,272 A | 7/1995 | Benner |
| 5,434,257 A | 7/1995 | Matteucci et al. |
| 5,446,137 A | 8/1995 | Maag et al. |
| 5,451,463 A | 9/1995 | Nelson et al. |
| 5,453,496 A | 9/1995 | Caruthers et al. |
| 5,455,233 A | 10/1995 | Spielvogel et al. |
| 5,457,187 A | 10/1995 | Gmeiner et al. |
| 5,457,272 A | 10/1995 | Hooykaas |
| 5,459,255 A | 10/1995 | Cook et al. |
| 5,466,677 A | 11/1995 | Baxter et al. |
| 5,466,786 A | 11/1995 | Buhr et al. |
| 5,470,967 A | 11/1995 | Huie et al. |
| 5,472,881 A | 12/1995 | Beebe et al. |
| 5,476,925 A | 12/1995 | Letsinger et al. |
| 5,484,908 A | 1/1996 | Froehler et al. |
| 5,486,603 A | 1/1996 | Buhr |
| 5,489,677 A | 2/1996 | Sanghvi et al. |
| 5,491,133 A | 2/1996 | Walder et al. |
| 5,502,177 A | 3/1996 | Matteucci et al. |
| 5,510,475 A | 4/1996 | Agrawal et al. |
| 5,512,439 A | 4/1996 | Hornes et al. |
| 5,512,667 A | 4/1996 | Reed et al. |
| 5,514,785 A | 5/1996 | Van Ness et al. |
| 5,519,126 A | 5/1996 | Hecht |
| 5,519,134 A | 5/1996 | Acevedo et al. |
| 5,525,465 A | 6/1996 | Haralambidis et al. |
| 5,525,711 A | 6/1996 | Hawkins et al. |
| 5,527,899 A | 6/1996 | Froehler |
| 5,536,821 A | 7/1996 | Agrawal et al. |
| 5,539,082 A | 7/1996 | Nielsen et al. |
| 5,541,306 A | 7/1996 | Agrawal et al. |
| 5,541,307 A | 7/1996 | Cook et al. |
| 5,541,313 A | 7/1996 | Ruth |
| 5,545,730 A | 8/1996 | Urdea et al. |
| 5,547,842 A | 8/1996 | Hogan et al. |
| 5,550,111 A | 8/1996 | Suhadolnik et al. |
| 5,552,538 A | 9/1996 | Urdea et al. |
| 5,552,540 A | 9/1996 | Haralambidis |
| 5,561,225 A | 10/1996 | Maddry et al. |
| 5,563,253 A | 10/1996 | Agrawal et al. |
| 5,565,350 A | 10/1996 | Kmiec |
| 5,565,552 A | 10/1996 | Magda et al. |
| 5,565,555 A | 10/1996 | Froehler et al. |
| 5,567,810 A | 10/1996 | Weis et al. |
| 5,567,811 A | 10/1996 | Misiura et al. |
| 5,571,799 A | 11/1996 | Tkachuk et al. |
| 5,574,142 A | 11/1996 | Meyer, Jr. et al. |
| 5,576,427 A | 11/1996 | Cook et al. |
| 5,578,717 A | 11/1996 | Urdea et al. |
| 5,578,718 A | 11/1996 | Cook et al. |
| 5,580,731 A | 12/1996 | Chang et al. |
| 5,585,481 A | 12/1996 | Arnold, Jr. et al. |
| 5,587,361 A | 12/1996 | Cook et al. |
| 5,587,371 A | 12/1996 | Sessler et al. |
| 5,587,469 A | 12/1996 | Cook et al. |
| 5,591,584 A | 1/1997 | Chang et al. |
| 5,591,722 A | 1/1997 | Montgomery et al. |
| 5,594,121 A | 1/1997 | Froehler et al. |
| 5,595,726 A | 1/1997 | Magda et al. |
| 5,596,086 A | 1/1997 | Matteucci et al. |
| 5,596,091 A | 1/1997 | Switzer |
| 5,597,696 A | 1/1997 | Linn et al. |
| 5,597,909 A | 1/1997 | Urdea et al. |
| 5,599,923 A | 2/1997 | Sessler et al. |
| 5,599,928 A | 2/1997 | Hemmi et al. |
| 5,602,240 A | 2/1997 | De Mesmaeker et al. |
| 5,608,046 A | 3/1997 | Cook et al. |
| 5,610,289 A | 3/1997 | Cook et al. |
| 5,610,300 A | 3/1997 | Altmann et al. |
| 5,614,617 A | 3/1997 | Cook et al. |
| 5,618,704 A | 4/1997 | Sanghvi et al. |
| 5,623,065 A | 4/1997 | Cook et al. |
| 5,623,070 A | 4/1997 | Cook et al. |
| 5,625,050 A | 4/1997 | Beaton et al. |
| 5,627,053 A | 5/1997 | Usman et al. |
| 5,633,360 A | 5/1997 | Bischofberger et al. |
| 5,637,459 A | 6/1997 | Burke et al. |
| 5,639,873 A | 6/1997 | Barascut et al. |
| 5,645,985 A | 7/1997 | Froehler et al. |
| 5,646,265 A | 7/1997 | McGee |
| 5,646,269 A | 7/1997 | Matteucci et al. |
| 5,652,355 A | 7/1997 | Metelev et al. |
| 5,652,356 A | 7/1997 | Agrawal |
| 5,658,873 A | 8/1997 | Bertsch-Frank et al. |
| 5,663,312 A | 9/1997 | Chaturvedula |
| 5,670,633 A | 9/1997 | Cook et al. |
| 5,672,697 A | 9/1997 | Buhr et al. |
| 5,677,437 A | 10/1997 | Teng et al. |
| 5,677,439 A | 10/1997 | Weis et al. |
| 5,681,941 A | 10/1997 | Cook et al. |
| 5,688,941 A | 11/1997 | Cook et al. |
| 5,700,920 A | 12/1997 | Altmann et al. |
| 5,700,922 A | 12/1997 | Cook |
| 5,714,331 A | 2/1998 | Buchardt et al. |
| 5,719,262 A | 2/1998 | Buchardt et al. |
| 5,721,218 A | 2/1998 | Froehler |
| 5,750,692 A | 5/1998 | Cook et al. |
| 5,763,588 A | 6/1998 | Matteucci et al. |
| 5,792,608 A | 8/1998 | Swaminathan et al. |
| 5,792,747 A | 8/1998 | Schally et al. |
| 5,830,653 A | 11/1998 | Froehler et al. |
| 6,005,096 A | 12/1999 | Matteucci et al. |
| 6,287,860 B1 | 9/2001 | Monia et al. |
| 6,361,944 B1 | 3/2002 | Mirkin et al. |
| 6,403,312 B1 | 6/2002 | Dahiyat et al. |
| 6,417,340 B1 | 7/2002 | Mirkin et al. |
| 6,495,324 B1 | 12/2002 | Mirkin et al. |
| 6,506,564 B1 | 1/2003 | Mirkin et al. |
| 6,544,776 B1 | 4/2003 | Gold et al. |
| 6,582,921 B2 | 6/2003 | Mirkin et al. |
| 6,602,669 B2 | 8/2003 | Letsinger et al. |
| 6,610,491 B2 | 8/2003 | Mirkin et al. |
| 6,656,730 B1 | 12/2003 | Manoharan |
| 6,677,122 B2 | 1/2004 | Mirkin et al. |
| 6,677,153 B2 | 1/2004 | Iversen |
| 6,678,548 B1 | 1/2004 | Echauz et al. |
| 6,682,895 B2 | 1/2004 | Mirkin et al. |

(56) References Cited

U.S. PATENT DOCUMENTS

| | | |
|---|---|---|
| 6,709,825 B2 | 3/2004 | Mirkin et al. |
| 6,720,147 B2 | 4/2004 | Mirkin et al. |
| 6,720,411 B2 | 4/2004 | Mirkin et al. |
| 6,750,016 B2 | 6/2004 | Mirkin et al. |
| 6,759,199 B2 | 7/2004 | Mirkin et al. |
| 6,767,702 B2 | 7/2004 | Mirkin |
| 6,773,884 B2 | 8/2004 | Mirkin et al. |
| 6,777,186 B2 | 8/2004 | Mirkin et al. |
| 6,812,334 B1 | 11/2004 | Mirkin et al. |
| 6,818,753 B2 | 11/2004 | Mirkin et al. |
| 6,827,979 B2 | 12/2004 | Mirkin et al. |
| 6,828,432 B2 | 12/2004 | Mirkin et al. |
| 6,844,161 B2 | 1/2005 | Siani et al. |
| 6,861,221 B2 | 3/2005 | Mirkin et al. |
| 6,878,814 B2 | 4/2005 | Mirkin et al. |
| 6,974,669 B2 | 12/2005 | Mirkin et al. |
| 6,991,900 B2 | 1/2006 | Shizuya |
| 7,001,616 B2 | 2/2006 | Batich et al. |
| 7,098,320 B1 | 8/2006 | Mirkin et al. |
| 7,223,833 B1 | 5/2007 | Nielsen et al. |
| 7,238,472 B2 | 7/2007 | Mirkin et al. |
| 7,323,309 B2 | 1/2008 | Mirkin et al. |
| 7,332,586 B2 | 2/2008 | Franzen et al. |
| 7,611,728 B2 | 11/2009 | Kidane et al. |
| 7,638,557 B2 | 12/2009 | Lipkin et al. |
| 7,667,004 B2 | 2/2010 | Zhong et al. |
| 7,727,969 B2 | 6/2010 | Farokhzad et al. |
| 2002/0172953 A1 | 11/2002 | Mirkin et al. |
| 2003/0147966 A1 | 8/2003 | Franzen et al. |
| 2003/0181412 A1 | 9/2003 | Erikson |
| 2004/0219565 A1 | 11/2004 | Kauppinen et al. |
| 2004/0247680 A1 | 12/2004 | Farokhzad et al. |
| 2004/0248099 A1 | 12/2004 | Goppelt et al. |
| 2005/0059016 A1 | 3/2005 | Ecker et al. |
| 2005/0074753 A1 | 4/2005 | Goldsborough |
| 2005/0096263 A1 | 5/2005 | Keay et al. |
| 2005/0136258 A1 | 6/2005 | Nie et al. |
| 2005/0197315 A1 | 9/2005 | Taira et al. |
| 2005/0214782 A1 | 9/2005 | Chen et al. |
| 2005/0244858 A1 | 11/2005 | Rossi et al. |
| 2006/0008907 A1 | 1/2006 | Friedman et al. |
| 2006/0019917 A1 | 1/2006 | Guerciolini et al. |
| 2006/0025363 A1 | 2/2006 | Breitenbach et al. |
| 2006/0035344 A1 | 2/2006 | Pachuk et al. |
| 2006/0088599 A1* | 4/2006 | Prasad .................. A61K 9/5115 424/490 |
| 2006/0105343 A1 | 5/2006 | Zetter et al. |
| 2006/0159921 A1 | 7/2006 | Murthy et al. |
| 2006/0183247 A1 | 8/2006 | Kim et al. |
| 2006/0188560 A1 | 8/2006 | Cheresh et al. |
| 2006/0233712 A1 | 10/2006 | Penades et al. |
| 2006/0252037 A1 | 11/2006 | Kolesnick et al. |
| 2006/0252053 A1* | 11/2006 | Stegh .................. C07K 14/4747 435/6.13 |
| 2006/0275371 A1 | 12/2006 | Dai et al. |
| 2007/0105139 A1 | 5/2007 | Nishigaki et al. |
| 2008/0057128 A1 | 3/2008 | Li et al. |
| 2008/0118912 A1* | 5/2008 | Dickson ............. A61K 49/0065 435/6.12 |
| 2008/0194463 A1 | 8/2008 | Weller et al. |
| 2008/0213177 A1* | 9/2008 | Rademacher ...... A61K 49/0054 424/1.73 |
| 2008/0213179 A1 | 9/2008 | Gaillard et al. |
| 2008/0220072 A1 | 9/2008 | Unger et al. |
| 2008/0274202 A1 | 11/2008 | Kraig et al. |
| 2008/0279946 A1 | 11/2008 | Hainfeld |
| 2008/0305106 A1 | 12/2008 | Brennan et al. |
| 2008/0306016 A1 | 12/2008 | Mirkin et al. |
| 2008/0317749 A1 | 12/2008 | Kastelein et al. |
| 2008/0317768 A1 | 12/2008 | Bianchi |
| 2009/0035576 A1 | 2/2009 | Prasad et al. |
| 2009/0081244 A1 | 3/2009 | Glenn et al. |
| 2009/0148384 A1 | 6/2009 | Fischer et al. |
| 2009/0155173 A1 | 6/2009 | Scherman et al. |
| 2009/0209629 A1 | 8/2009 | Mirkin et al. |
| 2009/0263331 A1 | 10/2009 | Wu et al. |
| 2009/0286853 A1 | 11/2009 | Gryaznov et al. |
| 2010/0047163 A1 | 2/2010 | Forte et al. |
| 2010/0158931 A1 | 6/2010 | Weinschenk et al. |
| 2010/0167051 A1 | 7/2010 | Goia et al. |
| 2010/0183504 A1 | 7/2010 | Chen |
| 2010/0183634 A1 | 7/2010 | Luo et al. |
| 2010/0209425 A1 | 8/2010 | Shusta et al. |
| 2010/0233084 A1* | 9/2010 | Narasimhaswamy .................. A61K 47/48238 424/9.1 |
| 2010/0233270 A1* | 9/2010 | Mirkin ................ A61K 9/5094 424/489 |
| 2010/0267814 A1 | 10/2010 | Bennett et al. |
| 2011/0034422 A1* | 2/2011 | Kannan ................ A61K 9/0048 514/152 |
| 2011/0111974 A1 | 5/2011 | Mirkin et al. |
| 2011/0172404 A1 | 7/2011 | Luo et al. |
| 2011/0262976 A1 | 10/2011 | Kandula et al. |

FOREIGN PATENT DOCUMENTS

| | | |
|---|---|---|
| JP | 2010500567 A | 1/2010 |
| WO | WO-89/002439 | 3/1989 |
| WO | WO-93/007883 A1 | 4/1993 |
| WO | WO-93/021259 | 10/1993 |
| WO | WO-95/006731 | 3/1995 |
| WO | WO-95/011910 | 5/1995 |
| WO | WO-97/012896 A1 | 4/1997 |
| WO | WO-98/004740 | 2/1998 |
| WO | WO-98/039352 A1 | 9/1998 |
| WO | WO-98/047343 | 10/1998 |
| WO | WO-99/011655 | 3/1999 |
| WO | WO-99/014226 A2 | 3/1999 |
| WO | WO-00/043045 A1 | 7/2000 |
| WO | WO-01/000876 A1 | 1/2001 |
| WO | WO-01/049869 | 7/2001 |
| WO | WO-01/051665 | 7/2001 |
| WO | WO-01/073123 A2 | 10/2001 |
| WO | WO-02/096262 A2 | 12/2002 |
| WO | WO-03/08539 A2 | 1/2003 |
| WO | WO-2003/008539 A2 | 1/2003 |
| WO | WO-2003/051278 A2 | 6/2003 |
| WO | WO-2005/079462 A2 | 9/2005 |
| WO | WO-2005/116226 A2 | 12/2005 |
| WO | WO-2006/012695 A1 | 2/2006 |
| WO | WO-2006/045541 A1 | 5/2006 |
| WO | WO-2006/064451 A2 | 6/2006 |
| WO | WO-2006/064453 A2 | 6/2006 |
| WO | WO-2006/138145 A1 | 12/2006 |
| WO | WO-2007/047455 A2 | 4/2007 |
| WO | WO-2008/019159 | 2/2008 |
| WO | WO-2008/098248 A2 | 8/2008 |
| WO | WO-2008/141289 A1 | 11/2008 |
| WO | WO-2008/151049 A2 | 12/2008 |
| WO | WO-2010/060110 A1 | 5/2010 |
| WO | WO-2010/081049 A1 | 7/2010 |
| WO | WO-2010/120420 A1 | 10/2010 |
| WO | WO-2011/017690 A2 | 2/2011 |
| WO | WO-2011/028847 A1 | 3/2011 |
| WO | WO-2011/053940 A2 | 5/2011 |

OTHER PUBLICATIONS

Abou-Alfa et al., Randomized phase III study of exatecan and gemcitabine compared with gemcitabine alone in untreated advanced pancreatic cancer, J. Clin. Oncol., 24(27):4441-7 (2006).

Agasti et al., Photoregulated release of caged anticancer drugs from gold nanoparticles, J. Am. Chem. Soc., 131(16):5728-9 (2009).

Agrawal et al., Antisence therapeutics: Is it as simple as complementary base recognition? Mol. Med. Today, 6: 72-81 (2000).

Ahmadi et al., Shape-controlled synthesis of colloidal platinum nanoparticles. Science, 272(5270): 1924-6 (1996).

Aime et al., Insights into the use of paramagnetic Gd(III) complexes in MR-molecular imaging investigations, J. Magn. Reson. Imaging, 16(4):394-406 (2002).

(56) References Cited

OTHER PUBLICATIONS

Aime et al., Pushing the sensitivity envelope of lanthanide-based magnetic resonance imaging (MRI) contrast agents for molecular imaging applications, Acc. Chem. Res., 42(7):822-31 (2009).
Alivisatos et al., Organization of 'nanocrystal molecules' using DNA. Nature, 382: 609-11 (1996).
Alivisatos, The use of nanocrystals in biological detection, Nat. Biotechnol., 22(1):47-52 (2004).
Allara et al., Spontaneously organized molecular assemblies. 1. Formation, dynamics, and physical properties of n-alkanoic acids adsorbed from solution on an oxidized aluminum surface. Langmuir, 1(1): 45-52 (1985).
Allara et al., The study of the gas-solid interaction of acetic acid with a cuprous oxide surface using reflection-absorption spectroscopy. J. Colloid Interface Sci., 49: 410-21 (1974).
Alric et al., Gadolinium chelate coated gold nanoparticles as contrast agents for both X-ray computed tomography and magnetic resonance imaging, J. Am. Chem. Soc., 130(18):5908-15 (2008).
Altieri, Survivin, versatile modulation of cell division and apoptosis in cancer, Oncogene, 22: 8581-9 (2003).
Altschul et al., Basic local alignment search tool. J. Mol. Biol., 215: 403-10 (1990).
Amirkhanov et al., Design of (Gd-DO3A)n-polydiamidopropanoyl-peptide nucleic acid-D(Cys-Ser-Lys-Cys) magnetic resonance contrast agents. Biopolymers, 89(12): 1061-76 (2008).
Angelini et al., Reversal of P-glycoprotein-mediated multidrug resistance in human sarcoma MES-SA/Dx-5 cells by nonsteroidal anti-inflammatory drugs, Oncol. Rep., 20(4):731-5 (2008).
Anton et al., Design and production of nanoparticles formulated from nano-emulsion templates—a review, J. Control Release, 128(3):185-99 (2008).
Aynie, et al., Spongelike alginate nanoparticles as a new potential system for the delivery of antisense oligonucleotides. Antisense Nucl. Acid Drug Dev., 9: 301-12 (1999).
Bahnemann, Photochemical Conversion and Storage of Solar Energy, Pelizetti and Schiavello (Eds.) pp. 251-276 (1991).
Baker et al., Dendrimer-mediated cell transfection in vitro. Meth. Molec. Biol., 245: 67-81 (2004).
Balasubramanian et al., Biodistribution of gold nanoparticles and gene expression changes in the liver and spleen after intravenous administration in rats, Biomaterials, 31 (8):2034-42 (2010).
Balin et al., Avenues for entry of peripherally administered protein to the central nervous system in mouse, rat, and squirrel monkey, J. Comp. Neurol., 251(2):260-80 (1986).
Banks, Physiology and pathology of the blood-brain barrier: implications for microbial pathogenesis, drug delivery and neurodegenerative disorders, J. Neurovirol., 5(6):538-55 (1999).
Bardeesy et al., Pancreatic cancer biology and genetics, Nat. Rev. Cancer, 2(12):897-909 (2002).
Bath et al., DNA nanomachines, Nat. Nanotechnol., 2: 275-84 (2007).
Baudhuim, Photochemical conversion and storage of solar energy. Kluwer Academic Publishers. 251-76 (1990).
Baudhuin et al., Molecular interactions between colloidal gold, proteins, and living cells. Chapter 1: 1-17 (1989).
Berton, et al., Highly loaded nanoparticulate carrier using an hydrophobic antisense oligonucleotide complex, Eur. J. Pharma. Sci., 9: 163-70 (1999).
Besch et al., Characterization and quantification of triple helix formation in chromosomal DNA. *J. Mol. Biol.*, 341: 979-89 (2004).
Bharali et al., Organically modified silica nanoparticles: a nonviral vector for in vivo gene delivery and expression in the brain. Proc. Natl. Acad. Sci. USA, 102(32): 11539-44 (2005).
Biancone et al., Magnetic resonance imaging of gadolinium-labeled pancreatic islets for experimental transplantation, NMR Biomed., 20(1):40-8 (2007).
Bickel et al., Delivery of peptides and proteins through the blood-brain barrier, Adv. Drug Deliv. Rev., 46(1-3):247-79 (2001).

Bielinska et al., DNA complexing with polyamidoamine dendrimers: implications for transfection. Bioconjug Chem., 10(5): 843-50 (1999).
Birck et al., Mutation and allelic loss of the PTEN/MMAC1 gene in primary and metastatic melanoma biopsies, J. Invest. Dermatol., 114: 277-80 (2000).
Bisht et al., Polymeric nanoparticle-encapsulated curcumin ("nanocurcumin"): a novel strategy for human cancer therapy, J. Nanobiotechnology, 5:3 (2007) (18 pages).
Bonoiu et al., Gold nanorod-siRNA induces efficient in vivo gene silencing in the rat hippocampus, Nanomedicine, 6.4:617 (Jun. 2011).
Bowman et al., Inhibition of HIV fusion with multivalent gold nanoparticles, J. Am. Chem. Soc., 130(22):6896-7 (2008).
Bramhill, Bacterial cell division, *Annu. Rev. Cell Dev. Biol.*, 13: 395-424 (1997).
Bratu et al., Visualizing the distribution and transport of mRNAs in living cells, Proc. Natl. Acad. Sci. USA, 100: 13308-13 (2003).
Broadwell et al., Cell biological perspective for the transcytosis of peptides and proteins through the mammalian blood-brain fluid barriers, pp. 165-99, In: Pardridge (ed.), The Blood-Brain Barrier, New York: Raven Press (1993).
Broadwell et al., Expanding the definition of the blood-brain barrier to protein, Proc. Natl. Acad. Sci. USA, 78(12):7820-4 (1981).
Brown et al., Surface treatment of the hydrophobic drug danazol to improve drug dissolution, Int. J. Pharmaceutics, 165:227-37 (1998).
Brus, Quantum crystallites and nonlinear optics. Appl. Phys. A. 53(6): 465-74 (1991).
Burwell, Modified silica gels as adsorbents and catalysts. Chem. Technol., 4: 370-7 (1974).
Cao et al., Raman dye-labeled nanoparticle probes for proteins, J. Am. Chem. Soc., 125(48):14676-7 (2003).
Capaccioli et al., Cationic lipids improve antisense oligonucleotide uptake and prevent degradation in cultured cells and inhuman serum, Biochem. Biophys. Res. Commun., 197(2): 818-25 (1993).
Caravan et al., The interaction of MS-325 with human serum albumin and its effect on proton relaxation rates, J. Am. Chem. Soc., 124(12):3152-62 (2002).
Caravan, Strategies for increasing the sensitivity of gadolinium based MRI contrast agents, Chem. Soc. Rev., 35(6):512-23 (2006).
Castoldi et al., A sensitive array for microRNA expression profiling (miChip) based on locked nucleic acids (LNA), RNA. 12: 913-20 (2006).
Cha et al., Hepatocellular carcinoma: current management, Curr. Probl. Surg., 47(1):10-67 (2010).
Chari et al., Immunoconjugates containing novel maytansinoids: promising anticancer drugs, Cancer Res., 52(1):127-31 (1992).
Charreyre et al., Fluorescence energy transfer study of the conformation of oligonucleotides covalently bound to polystyrene latex particles. Langmuir, 13: 3103-10 (1997).
Chavany et al., Polyalkylcyanoacrylate nanoparticles as polymeric carriers for antisense oligonucleotides, Pharma. Res., 9(4): 441-9 (1992).
Chavany, et al., Adsorption of oligonucleotides onto polyisohexylcyanoacrylate nanoparticles protects them against nucleases and increases their cellular uptake. Pharma. Res., 11(9): 1370-8 (1994).
Chen et al., Kinetics and thermodynamics of DNA hybridization on gold nanoparticles, Nucl. Acids Res., 37: 3756-65 (2009).
Chen et al., MDR 1 activation is the predominant resistance mechanism selected by vinblastine in MES-SA cells, Br. J. Cancer, 83(7):892-8 (2000).
Cheng et al., Addressing brain tumors with targeted gold nanoparticles: a new gold standard for hydrophobic drug delivery?, Small, 7(6):2301-6 (2011).
Cheng et al., Tandem synthesis of core-shell brush copolymers and their transformation to peripherally cross-linked and hollowed nanostructures, J. Am. Chem. Soc., 128(21):6808-9 (2006).
Cheung et al., Akt3 and mutant V600E B-Raf cooperate to promote early melanoma development, Cancer Res., 68:3429-39 (2008).
Chirila et al., The use of synthetic polymers for delivery of therapeutic antisense oligodeoxynucleotides. *Biomaterials*, 23: 321-42 (2002).

(56) References Cited

OTHER PUBLICATIONS

Chithrani et al., Elucidating the mechanism of cellular uptake and removal of protein-coated gold nanoparticles of different sizes and shapes. Nano Lett., 7: 1542-50 (2007).
Chithrani, et al., Determining the size and shape dependence of gold nanoparticle uptake into mammalian cells, Nano Lett., 6(4): 662-8 (2006).
Chompoosor et al., Charge dependence of ligand release and monolayer stability of gold nanoparticles by biogenic thiols, Bioconjugate Chem., 19:1342-5 (2008).
Chrisey et al., Covalent attachment of synthetic DNA to self-assembled monolayer films, Nucl. Acids Res., 24: 3031-9 (1996).
Chu et al., Effects of photoactivated 5-aminolevulinic acid hexyl ester on MDR1 over-expressing human uterine sarcoma cells, Toxicol. Lett., 181(1):7-12 (2008).
Cload et al., Polyether tethered oligonucleotide probes. J. Am. Chem. Soc., 113(16): 6324-6 (1991).
Connor et al., Gold nanoparticles are taken up by human cells but do not cause acute cytotoxicity, Small, 1(3):325-7 (2005).
Cook, Medicinal chemistry of antisense oligonucleotides—future opportunities. Anticancer Drug Des., 6(6):585-607 (1991).
Crawford et al., A novel B-RAF inhibitor blocks interleukin-8 (IL-8) synthesis in human melanoma xenografts, revealing IL-8 as a potential pharmacodynamic biomarker, Mol. Cancer Ther., 7: 492-9 (2008).
Crawford et al., Peptide aptamers: Tools for biology and drug discovery. 2(1): 72-9 (2003).
Crich et al., Improved route for the visualization of stem cells labeled with a Gd-/Eu-chelate as dual (MRI and fluorescence) agent, Magn. Reson. Med., 51(5):938-44 (2004).
Crooke et al., Progress in antisense technology. Ann. Rev. Med., 55: 61-95 (2004).
Curtis et al., A morphology-selective copper organosol. Angew. Chem. Int. Ed. Engl., 27: 1530-3 (1988).
Daniel et al., Gold nanoparticles: assembly, supramolecular chemistry, quantum-size-related properties, and applications toward biology, catalysis, and nanotechnology. Chem Rev., 104(1): 293-346 (2004).
Dankort et al., A new mouse model to explore the initiation, progression, and therapy of BRAFV600E-induced lung tumors, Genes Dev., 21: 379-84 (2007).
Dankort et al., Braf(V600E) cooperates with Pten loss to induce metastatic melanoma, Nat Genet., 41: 544-52 (2009).
Davies et al., A novel AKT3 mutation in melanoma tumours and cell lines, Br. J. Cancer, 99: 1265-8 (2008).
Debouttiere et al., Design of gold nanoparticles for magnetic resonance imaging. Adv. Funct. Mater., 16:2330 (2006).
Dehouck et al., A new function for the LDL receptor: transcytosis of LDL across the blood-brain barrier, J. Cell Biol., 138(4):877-89 (1997).
Demers et al., Combinatorial templates generated by dip-pen nanolithography for the formation of two-dimensional particle arrays, Angew. Chem. Int. Ed., 40: 3071-3 (2003).
DeMesmaeker et al., Antisense oligonucleotides. Acc. Chem. Res., 28(9): 366-74 (1995).
DeMesmaeker et al., Backbone modifications in oligonucleotides and peptide nucleic acid systems, Curr. Opin. Struct. Biol., 5: 343-55 (1995).
Deutsch et al., Synthesis of congeners and prodrugs. 3. Water-soluble prodrugs of taxol with potent antitumor activity, J. Med. Chem., 32(4):788-92 (1989).
Devlin et al., Random peptide libraries: a source of specific protein binding molecules, Science, 249: 404-6 (1990).
Dhar et al., Polyvalent oligonucleotide gold nanoparticle conjugates as delivery vehicles for platinum(IV) warheads. *J. Am. Chem. Soc.*, 131(41): 14652-3 (2009).
Dhar et al., Targeted single wall carbon nanotube mediated Pt(IV) prodrug delivery using folate as a homing device. *J. Am. Chem. Soc.*, 130(34): 11467-76 (2008).
Dhomen et al., BRAF signaling and targeted therapies in melanoma, Hematol. Oncol. Clin. North Am., 23: 529-45, ix (2009).
Donachie, The cell cycle of *Escherichia coli., Annu. Rev. Microbiol.*, 47: 199-230 (1993).
Dreyfus et al., Simple quantitative model for the reversible associate of DNA coated colloids, Phys. Rev. Lett., 102: 048301 (2009).
Dubertret et al., Single-mismatch detection using gold-quenched fluorescent oligonucleotides, Nat. Biotechnol., 19: 365-70 (2001).
Duffy et al., Blood-brain barrier transcytosis of insulin in developing rabbits, Brain Res., 420(1):32-8 (1987).
Duimstra et al., A gadolinium chelate for detection of beta-glucuronidase: a self-immolative approach, J. Am. Chem. Soc., 127(37):12847-55 (2005).
Dulkeith et al., Gold nanoparticles quench fluorescence by phase induced radiative rate suppression, Nano Lett., 5: 585-9 (2005).
Durand et al., Circular dichroism studies of an oligodeoxyribonucleotide containing a hairpin loop made of a hexaethylene glycol chain: conformation and stability. Nucl. Acids Res., 18(21): 6353-9 (1990).
Dykxhoorn et al., Killing the messenger: short RNAs that silence gene expression, Nat. Rev. Mol. Cell Biol., 4(6):457-67 (2003).
Eckstein (Ed.), Oligonucleotides and analogues, 1st Ed., Oxford University Press, New York (1991).
Elaissari et al., Effect of charge nature on the adsorption of single-stranded DNA fragments onto latex particles. J. Colloid Interface Sci., 202: 251-60 (1998).
Elghanian et al., Selective colorimetric detection of polynucleotides based on the distance-dependent optical properties of gold nanoparticles. Science, 277: 1078-81 (1997).
Eltekova et al., Adsorption of aromatic compounds from solutions on titanium dioxide and silica. Langmuir, 3(6): 951-7 (1987).
Endres et al., DNA-Ti02 nanoconjugates labeled with magnetic resonance contract agents. *J. Am. Chem. Soc.* 129(51): 15760-1 (2007).
Englisch et al., Chemically modified oligonucleotides as probes and inhibitors, Angew. Chem. Int. Ed. English, 30: 613-29 (1991).
Enustun et al., Coagulation of colloidal gold, J. Am. Chem. Soc., 85(21):3317-28 (1963).
Fahy et al., Design and synthesis of polyacrylamide-based oligonucleotide supports for use in nucleic acid diagnostics, Nucl. Acids Res., 21: 1819-26 (1993).
Fattal et al., Biodegradable polyalkylcyanoacrylate nanoparticles for the delivery of oligonucleotides. J. Control Rel., 53(1-3): 137-43 (1998).
Faulds et al., Evaluation of surface-enhanced resonance Raman scattering for quantitative DNA analysis. Anal. Chem., 76: 412-7 (2004).
Femino et al., Visualization of single RNA transcripts in situ. Science, 280: 585-90 (1998).
Feng et al., pp. 15-34, vol. 45, In: Jain (ed.), Drug Delivery to teh Central Nervous System (2010).
Ferentz et al., Disulfide-crosslinked oligonucleotides. J. Am. Chem. Soc., 113(10): 4000-2 (1991).
Fillebeen et al., Receptor-mediated transcytosis of lactoferrin through the blood-brain barrier, J. Biol. Chem., 274(11):7011-7 (1999).
Flandroy et al., (D, L)Polyactide microspheres as embolic agent. *Neuroradiology*, 32: 311-5 (1990).
Freier et al., The ups and downs of nucleic acid duplex stability: structure-stability studies on chemically-modified DNA:RNA duplexes, Nucleic Acids Res., 25(22):4429-43 (1997).
Frens, Controlled nucleation for the regulation of the particle size in monodisperse gold suspensions. *Nat. Phys. Sci.*, 241: 20-2 (1973).
Frens, Particle size and sol stability in metal colloids, Kolloid-Zeitschrift and Zeitschrift fur Polymere, 250(7):736-41 (1972).
Frullano et al., Multimodal MRI contrast agents, J. Biol. Inorg. Chem., 12(7):939-40 (2007).
Fukuda et al., Bull. Chem. Soc. Jpn., 64:2013-5 (1991).
Fukuda et al., J. Org. Chem., 56(11):3729-31 (1991).
Furstner et al., Catalytic carbophilic activation: catalysis by platinum and gold pi acids, Angew Chem Int Ed Engl., 46(19):3410-49 (2007).

(56) References Cited

OTHER PUBLICATIONS

Gaillard et al., Targeted delivery across the blood-brain barrier, Expert Opin. Drug Deliv., 2(2):299-309 (2005).
Gao et al., Secondary structure effects on DNA hybridization kinetics: a solution versus surface comparison. Nucl. Acids Res., 34: 3370-7 (2006).
Gavrieli et al., Identification of programmed cell death in situ via specific labeling of nuclear DNA fragmentation, J. Cell Biol., 119(3):493-501 (1992).
Gerdes et al., Experimental determination and system level analysis of essential genes in *Escherichia coli* MG1655. *J. Bacteriol.*, 185: 5673-84 (2003).
Gestwicki et al., Influencing receptor-ligand binding mechanisms with multivalent ligand architecture. J. Am. Chem. Soc., 124: 14922-33 (2002).
Ghosh et al., Gold nanoparticles in delivery applications, Adv. Drug Deliv. Rev. 60(11):1307-15 (2008).
Gibson et al., Paclitaxel-functionalized gold nanoparticles, J. Am. Chem. Soc., 129(37):11653-61 (2007).
Gidwani et al., Hybridization kinetics of double-stranded DNA probes for rapid molecular analysis. Analyst, 134: 1675-81 (2009).
Giljohann et al., Gene regulation with polyvalent siRNA-nanoparticle conjugates. J. Am. Chem. Soc., 131:2072-3 (2009).
Giljohann et al., Gold nanoparticles for biology and medicine, Angew Chem. Int. Ed. Engl., 49(19):3280-94 (2010).
Giljohann et al., Oligonucleotide loading determines cellular uptake of DNA-modified gold nanoparticles. Nano Lett., 7(12): 3818-21 (2007).
Goel et al., Melanocytic nevus-like hyperplasia and melanoma in transgenic BRAFV600E mice. Oncogene, 28: 2289-98 (2009).
Golden et al., Human blood-brain barrier leptin receptor. Binding and endocytosis in isolated human brain microvessels, J. Clin. Invest., 99(1):14-8 (1997).
Goodrich et al., Non-coding-RNA regulators of RNA polymerase II transcription, Nat. Rev. Mol. Cell Biol., 7(8):612-6 (2006).
Grabar et al., Preparation and Characterization of Au Colloid Monolayers. Anal. Chem., 67(4):735-43 (1995).
Guerrero et al., Improving the brain delivery of gold nanoparticles by conjugation with an amphipathic peptide, Nanomedicine, 5(6):897-913 (2010).
Guo et al., CELL-SELEX: Novel perspectives of aptamer-based therapeutics, Int. J. Mol. Sci., 9: 668-78 (2008).
Guy et al., Transdermal drug delivery, Handbook Exp. Pharmacol., 197:399-410 (2010).
Hale et al., Recruitment of ZipA to the septal ring of *Escherichia coli* is dependent on FtsZ and independent of FtsA. J. Bacteriol., 181: 167-76 (1999).
Hames et al. (eds.), Gene Probes 1, New York: IRL Press (1995).
Hamilton et al., A species of small antisense RNA in post-transcriptional gene silencing in plants. Science, 286: 950-2 (1999).
Hammond et al., An RNA-directed nuclease mediates post-transcriptional gene silencing in *Drosophilia* cells. Nature, 404: 293-6 (2000).
Han et al., A gold nanoparticle based approach for screening triplex DNA binders, J. Am. Chem. Soc., 128(15):4954-5 (2006).
Harris et al., Effect of pegylation on pharmaceuticals, Nat. Rev. Drug Discov., 2(3):214-21 (2003).
Hashmi et al., Gold catalysis, Angew Chem Int Ed Engl., 45(47):7896-936 (2006).
Hashmi et al., Gold-catalyzed organic reactions, Chem. Rev., 107(7):3180-211 (2007).
Hayashi, Ultrafine particles, J. Vac. Sci. Technol. A, 5(4):1375-84 (1987).
Hayashi, Ultrafine particles, Physics Today, pp. 44-51 (1987).
Hayat, (Ed.) Colloidal Gold: Principles, Methods, and Applications, vol. 1, Table of Contents, pp. v-xvii; vol. 2, Table of Contents pp. v-xix; vol. 3, Table of Contents, pp. v-xiv, Academic Press, San Diego (1989-1991).

He et al., Colloidal Au-enhanced surface plasmon resonance for ultrasensitive detection of DNA hybridization. J. Am. Chem. Soc., 122(38): 9071-7 (2000).
Hegner et al., Modified DNA immobilized on bioreactive self-assembled monolayer on gold for dynamic force microscopy imaging in aqueous buffer solution, J. Vac. Sci. Technol. B, 14(2):1418-21 (1996).
Henglein et al., Absorption spectrum and some chemical reactions of colloidal platinum in aqueous solution. J. Phys. Chem., 99(38): 14129-36 (1995).
Henglein, Mechanism of reactions on colloidal microelectrodes and size quantization effects. Top. Curr. Chem., 143: 113-80 (1998).
Henglein, Small-particle research: physicochemical properties of extremely small colloidal metal and semiconductor particles. Chem. Rev., 89(8): 1861-73 (1989).
Hickman et al., Combining spontaneous molecular assembly with microfabrication to pattern surfaces: selective binding of isonitriles to platinum microwires and characterization by electrochemistry and surface spectroscopy. J. Am. Chem. Soc., 111(18): 7271-2 (1989).
Holen et al., Positional effects of short interfering RNAs targeting the human coagulation trigger tissue factor. *Nucl. Acids Res.*, 30: 1757-66 (2002).
Hsu et al., Delivery of siRNA and other macromolecules into skin and cells using a peptide enhancer, Proc. Natl. Acad. Sci. USA, 108(38):15816-21 (2011).
Hu et al., Advances in high-field magnetic resonance imaging, Annu. Rev. Biomed.Eng., 6:157-84 (2004).
Hu et al., Hollow chitosan/poly(acrylic acid) nanospheres as drug carriers, Biomacromolecules, 8(4):1069-76 (2007).
Hubbard, Electrochemistry of well-defined surfaces. Acc. Chem. Res., 13: 177-84 (1980).
Hurst et al., "Multisegmented one-dimensional nanorods prepared by hard-template synthetic methods," Angew. Chem. Int. Ed. Engl., 45:2672-2692 (2006).
Hurst et al., Maximizing DNA loading on a range of gold nanoparticle sizes, Anal. Chem., 78(24):8313-8 (2006).
Hurst et al., Maximizing DNA loading on a range of gold nanoparticle sizes. Anal. Chem., 78:8313 (2006).
Hussain et al., A novel anionic dendrimer for improved cellular delivery of antisense oligonucleotides. J. Controlled Rel., 99: 139-55 (2004).
Hwu et al., Targeted Paclitaxel by conjugation to iron oxide and gold nanoparticles, J. Am. Chem. Soc., 131(1):66-8 (2009).
ILER, The Chemistry of Silica, Chapter 6, New York: Wiley (1979).
International Preliminary Report on Patentability, International Application No. PCT/US12/55635, dated Mar. 18, 2014.
International Search Report and Written Opinion, International Application No. PCT/US2012/055635, dated Dec. 7, 2012.
Introducing Antisense Oligonucleotides into Cells, Innovation & Precision in Nucleic Acid Synthesis, Integrated DNA Technologies (2005).
Jackson et al., *Escherichia coli* O157:H7 diarrhoea associated with well water and infected cattle on an Ontario farm, *Epidemiol. Infect.*, 120:17-20 (1998).
Jackson et al., How do microRNAs regulate gene expression?, Sci STKE, 2007(367):re1 (2007).
Jaschke et al., Automated incorporation of polyethylene glycol in synthetic oligonucleotides. Tetrahedron Lett., 34: 301-4 (1993).
Jason et al., Toxicology of antisense therapeutics. Toxicol. Appl. Pharmacol., 201(1): 66-83 (2004).
Jefferies et al., Transferrin receptor on endothelium of brain capillaries, Nature, 312(5990):162-3 (1984).
Jen et al., A nonviral transfection approach in vitro: the design of a gold nanoparticle vector joint with microelectromechanical systems. Langmuir, 20(4): 1369-74 (2004).
Jeong et al., Novel intracellular delivery system of antisense oligonucleotide by self-assembled hybrid micelles composed of DNA/PEG conjugate and cationic fusogenic peptide. Bioconjugate Chem., 14: 473-9 (2003).
Jin et al., Radiosensitization of paclitaxel, etanidazole and paclitaxel+etanidazole nanoparticles on hypoxic human tumor cells in vitro, Biomaterials, 28(25):3724-30 (2007).

(56) References Cited

OTHER PUBLICATIONS

Jin et al., What controls the melting properties of DNA-linked gold nanoparticle assemblies? J. Am. Chem. Soc., 125: 1643 (2003).
Johanson, The choroid plexus-arachnoid membrane-cerebrospinal fluid system, pp. 33-104, In: Boulton et al. (eds.), Neuronal Microenvironment, New Jersey: Humana Press (1988).
Jones et al., Blood-brain barrier transport of therapeutics via receptor-mediation, Pharm. Res., 24(9):1759-71 (2007).
Kalman et al., Potentiometric and relaxometric properties of a gadolinium-based MRI contrast agent for sensing tissue pH, Inorg. Chem., 46(13):5260-70 (2007).
Kan et al., Distribution and effect of iodized poppyseed oil in the liver after hepatic artery embolization: experimental study in several animal species, Radiology, 186(3):861-6 (1993).
Kan et al., Role of Kupffer cells in iodized oil embolization, Invest. Radiol., 29(11):990-3 (1994).
Kasuya et al., Chapter 8—Bio-nanocapsule-liposome conjugates for in vivo pinpoint drug and gene delivery, Methods Enzymol., 464:147-66 (2009).
Katz et al., Integrated nanoparticle-biomolecule hybrid systems: synthesis, properties, and applications, Angew. Chem. Int. Ed., 43: 6042-108 (2004).
Katz, The reversible reaction of sodium thymonucleate and mercuric chloride, *J. Am. Chem. Soc.*, 74: 2238-45 (1952).
Khlebtsov et al., Biodistribution and toxicity of engineered gold nanoparticles: a review of in vitro and in vivo studies, Chem. Soc. Rev., 40:164771 (2011).
Kim et al., Biodegradable quantum dot nanocomposites enable live cell labeling and imaging of cytoplasmic targets, Nano Lett., 8(11):3887-92 (2008).
Kim et al., Direct synthesis of polymer nanocapsules with a noncovalently tailorable surface, Angew. Chem. Int. Ed. Engl., 46(19):3471-4 (2007).
Kim et al., Direct synthesis of polymer nanocapsules: self-assembly of polymer hollow spheres through irreversible covalent bond formation, J. Am. Chem. Soc., 132(28):9908-19 (2010).
Kim et al., Facile, template-free synthesis of stimuli-responsive polymer nanocapsules for targeted drug delivery, Angew. Chem. Int. Ed. Engl., 49(26):4405-8 (2010).
Kloosterman et al., In situ detection of miRNAs in animal embryos using LNA-modified oligonucleotide probes, Nat. Methods, 3: 27-9 (2006).
Koffie et al., Nanoparticles enhance brain delivery of blood-brain barrier-impermeable probes for in vivo optical and magnetic resonance imaging, Proc. Natl. Acad. Sci. USA (2011).
Kolarova et al., Preparation of magnetic oligo (dT) particles, Biotechniques, 20: 196-8 (1996).
Kondo et al., Nanotube formation through the continuous one-dimensional fusion of hollow nanocapsules composed of layer-by-layer poly(lactic acid) stereocomplex films, J. Am. Chem. Soc., 132(24):8236-7 (2010).
Kopylov et al., Combinatorial chemistry of nucleic acids: SELEX, Mol. Biol., 34: 940-54 (2000).
Kosturko et al., The crystal and molecular structure of a 2:1 complex of 1-methylthymine-mercury(II), Biochem., 13: 3949-52 (1974).
Kroschwitz (Ed.), The Concise Encyclopedia of Polymer Science and Engineering, pp. 858-859, John Wiley & Sons (1990).
Krutzfeldt et al., Silencing of microRNAs in vivo with 'antagomirs', Nature, 438(7068):685-9 (2005).
Kukowska-Latallo et al., Efficient transfer of genetic material into mammalian cells using Starburst polyamidoamine dendrimers, Proc. Natl. Acad. Sci. USA, 93: 4897-902 (1996).
Kusuhara et al., Efflux transport systems for drugs at the blood-brain barrier and blood-cerebrospinal fluid barrier (Part 1), Drug Discov. Today, 6(3):150-6 (2001).
Landfester et al., From polymeric particles to multifunctional nanocapsules for biomedical applications using the miniemulsion process, J. Polymer Sci. Part A, 48(3):493-515 (2010).
Lannutti et al., Human angiostatin inhibits murine hemangioendothelioma tumor growth in vivo, Cancer Res., 57: 5277-80 (1997).
Leachman et al., Therapeutic siRNAs for dominant genetic skin diseases including pachyonychia congenita, J. Dermatol. Sci., 51(3):151-7 (2008).
Lebedeva et al., Antisense oligonucleotides: Promise and reality. Annu. Rev. Pharmacol. Toxicol., 41: 403-19 (2001).
Lee et al., Adsorption of ordered zirconium phosphonate multilayer films on silicon and gold surfaces. J. Phys. Chem., 92: 2597-601 (1988).
Lee et al., Chip-based scanometric detection of mercuric ion using DNA-functionalized gold nanoparticles, Anal. Chem., 80(17):6805-8 (2008).
Lee et al., Colorimetric detection of mercuric ion (Hg2+) in aqueous media using DNA-functionalized gold nanoparticles, Angew. Chem. Int. Ed. Engl., 46(22):4093-6 (2007).
Lemaigre et al., Transcriptional control of genes that regulate glycolysis and gluconeogenesis in adult liver, *Biochem. J.*, 303: 1-14 (1994).
Leslie et al., A new tool for oligonucleotides import into cells. Clin. Chem., 55: 609-10 (2009).
Leunissen et al., Switchable self-protected attractions in DNA-functionalized colloids. Nat. Mater., 8: 590-95 (2009).
Lewis, "Controlled release of bioactive agents from lactide/glycolide polymer", pp. 1-41, In: Chasin et al. (eds.), Biodegradable Polymers as Drug Delivery Systems, Marcel Dekker (1990).
Li et al., A calcium-sensitive magnetic resonance imaging contrast agent. J. Am. Chem. Soc., 121:1413 (1999).
Li et al., Dual-reactive surfactant used for synthesis of functional nanocapsules in miniemulsion, J. Am. Chem. Soc., 132(23):7823-5 (2010).
Li et al., Gold-catalyzed organic transformations, Chem. Rev., 108(8):3239-65 (2008).
Li et al., Reversible and chemically programmable micelle assembly with DNA block-copolymer amiphiphiles, Nano Lett., 4(6):1055-8 (2004).
Lin et al., Effector/memory but not naive regulatory T cells are responsible for the loss of concomitant tumor immunity. J. Immunol., 182: 6095-104 (2009).
Lin et al., Modeling genomic diversity and tumor dependency in malignant melanoma. Cancer Res., 68: 664-73 (2003).
Link et al., J. Phys. Chem. B, 103(21):4212-7 (1999).
Lipshutz et al., High density synthetic oligonucleotide arrays. Nanotechnology, 14: R15-27 (2003).
Liu et al., Accelerated color change of gold nanoparticles assembled by DNAzymes for simple and fast colorimetric Pb2+ detection. J. Am. Chem. Soc., 126: 12298-305 (2004).
Liu et al., ARDB—Antibiotic Resistance Genes Database. *Nucl. Acids Res.*, 37: D443-7 (2009).
Liu et al., Argonaute2 is the catalytic engine of mammalian RNAi. Science, 305(5689): 1437-41 (2004).
Liu et al., Cross-linked polynorbornene-coated gold nanoparticles: dependence of particle stability on cross-linking position and cross-linker structure, Langmuir, 24(19):11169-74 (2008).
Liu et al., De-N-acetyl GM3 promotes melanoma cell migration and invasion through urokinase plasminogen activator receptor signaling-dependent MMP-2 activation. Cancer Res., 69: 8662-9 (2009).
Liu et al., DNA-based micelles: synthesis, micellar properties and size-dependent cell permeability, Chemistry, 16(12):3791-7 (2010).
Liu et al., New poly(d-glucaramidoamine)s induce DNA nanoparticle formation and efficient gene delivery into mammalian cells. J. Am. Chem. Soc., 126: 7422-3 (2004).
Liu et al., Rational design of "turn-on" allosteric DNAzyme catalytic beacons for aqueous mercury ions with ultrahigh sensitivity and selectivity, Angew. Chem. Int. Ed. Engl., 46(60):7587-90 (2007).
Liu et al., Synthesis, stability, and cellular internalization of gold nanoparticles containing mixed peptide-poly(ethylene glycol) monolayers. Anal. Chem., 79: 2221-9 (2007).

(56) References Cited

OTHER PUBLICATIONS

Llovet et al., Arterial embolisation or chemoembolisation versus symptomatic treatment in patients with unresectable hepatocellular carcinoma: a randomised controlled trial, Lancet, 359(9319):1734-9 (2002).
Loeken, Effects of mutation of the CREB binding site of the somatostatin promoter on cyclic AMP responsiveness in CV-1 cells. Gene Expr., 3: 253-64 (1993).
Love et al., Self-assembled monolayers of thiolates on metals as a form of nanotechnology. Chem. Rev., 105: 1103-69 (2005).
Lutkenhaus et al., Bacterial cell division and the Z ring. Annu. Rev. Biochem., 66: 93-116 (1997).
Lytton-Jean et al., A thermodynamic investigation into the binding properties of DNA functionalized gold nanoparticle probes and molecular fluorophore probes. J. Am. Chem Soc., 127: 12754-5 (2005).
Ma et al., Design and synthesis of RNA miniduplexes via a synthetic linker approach. 2. Generation of covalently closed, double-stranded cyclic HIV-1 TAR RNA analogs with high Tat-binding affinity. Nucl. Acids Res., 21: 2585-9 (1993).
Ma et al., Design and synthesis of RNA miniduplexes via a synthetic linker approach. Biochemistry, 32(7): 1751-8 (1993).
Major et al., Bioresponsive, cell-penetrating, and multimeric MR contrast agents, Acc. Chem. Res., 42(7):893-903 (2009).
Major et al., The synthesis and in vitro testing of a zinc-activated MRI contrast agent, Proc. Natl. Acad. Sci. USA, 104(35):13881-6 (2007).
Maoz et al., Penetration-controlled reactions in organized monolayer assemblies. 1. Aqueous permanganate interaction with monolayer and multilayer films of long-chain surfactants. Langmuir, 3: 1034-44 (1987).
Maoz et al., Penetration-controlled reactions in organized monolayer assemblies. 2. Aqueous permanganate interaction with self-assembling monolayers of long-chain surfactants. Langmuir, 3: 1045-1051 (1987).
Marinakos et al., Gold nanoparticles as templates for the synthesis of hollow nanometer-sized conductive polymer capsules. Ad. Mater., 11: 34-37 (1999).
Marinakos et al., Template synthesis of one-dimensional Au, Au-poly(pyrrole), and poly(pyrrole) nanoparticle arrays, Chem. Mater., 10:1214-9 (1998).
Marinakos et al., Template synthesis of one-dimensional Au, Au-poly(pyrrole), and poly(pyrrole) nanoparticle arrays. Chem. Mater., 10: 1214-19 (1998).
Martin et al., 38. Ein neuer zugang zu 2'-O-alkylribonucleosiden und eigenschaften deren oligonucleotide, Helv. Chim. Acta, 78: 486-504 (1995) [English abstract only.].
Martinez et al., Locked nucleic acid based beacons for surface interaction studies and biosensor development. Anal. Chem., 81: 3448-54 (2009).
Maruyama, et al., Nanoparticle DNA carrier with poly(L-lysine) grafted polysaccharide copolymer and poly(D,L-lactic acid). Bioconjugate Chem., 8: 735-742 (1997).
Massart, Preparation of aqueous magnetic liquids in alkaline and acidic media. IEEE Transactions on Magnetics. 17(2): 1247-8 (1981).
Matijevic, Fine particles part II: formation mechanisms and applications, MRS Bulletin 15(1):16-17 (1990).
Matsuura et al., Construction and characterization of protein libraries composed of secondary structure modules. Protein Sci., 11: 2631-43 (2002).
Matteucci et al., Synthesis of deoxyoligonucleotides on a polymer support. J. Am. Chem. Soc., 103: 3185-91 (1981).
Mattson et al., A practical approach to crosslinking. Molec. Biol. Rep., 17: 167-83 (1993).
Maxwell et al., Self-assembled nanoparticle probes for recognition and detection of biomolecules. J. Am. Chem. Soc., 124: 9606-12 (2002).
Maye et al., A simple method for kinetic control of DNA-induced nanoparticle assembly. J. Am. Chem. Soc., 128: 14020-1 (2006).

Mayer (ed.), Nucleic Acid and Peptide Aptamers: Methods and Protocols (Humana Press, 2009).
McCurdy et al., Deoxyligonucleotides with inverted polarity: Synthesis and use in triple-helix formation. Nucleosides & Nucleotides, 10: 287-90 (1991).
McGehee et al., Differentiation-specific element: a cis-acting developmental switch required for the sustained transcriptional expression of the angiotensinogen gene during hormonal-induced differentiation of 3T3-L1 fibroblasts to adipocytes. Mol. Endocrinol., 7: 551-60 (1993).
McKenzie et al., Sequence-specific DNA detection using high-affinity LNA-functionalized gold nanoparticles. Small, 3(11): 1866-8 (2007).
McManus et al., Gene silencing in mammals by small interfering RNAs. Nat. Rev. Genet., 3(10): 737-47 (2002).
Mendell, MicroRNAs: critical regulators of development, cellular physiology and malignancy. Cell Cycle, 4(9):1179-84 (2005).
Merbach et al. (eds.), The Chemistry of Contrast Agents in Medical Magnetic Resonance Imaging, 1st ed., New York: Wiley (2001).
Miller et al., Antisense oligonucleotides: Strategies for delivery. PSTT, 1(9): 377-86 (1998).
Milne et al., An approach to gene-specific transcription inhibition using oligonucleotides complementary to the template strand of the open complex. Proc. Natl. Acad. Sci. USA, 97(7):3136-41 (2000).
Mirkin et al., A DNA-based method for rationally assembling nanoparticles into macroscopic materials. Nature, 382(6592): 607-9 (1996).
Mitragotri et al., Ultrasound-mediated transdermal protein delivery, Science, 289:850-3 (1995).
Mittal, Improving the efficiency of RNA interference in mammals, Nat. Rev. Genet., 5(5):355-65 (2004).
Modo et al. (eds.), Molecular and Cellular MR Imaging, Florida: CRC Press (2007).
Modo et al., Mapping transplanted stem cell migration after a stroke: a serial, in vivo magnetic resonance imaging study, Neuroimage, 21(1):311-7 (2004).
Moriggi et al., Gold nanoparticles functionalized with gadolinium chelates as high-relaxivity MRI contrast agents, J. Am. Chem. Soc., 131(31):10828-9 (2009).
Moughton et al., Hollow nanostructures from self-assembled supramolecular metallo-triblock copolymers, Soft Matter, 5(12):2361-70 (2009).
Mucic et al., Synthesis and characterization of DNA with ferrocenyl groups attached to their 5-termini: electrochemical characterization of a redox-active nucleotide monolayer. Chem. Commun., 4: 555-7 (1996).
Musumeci et al., PLA/PLGA nanoparticles for sustained release of docetaxel, Int. J. Pharm., 325(1-2):172-9 (2006).
Myers et al., A cyclopentane conformational restraint for a peptide nucleic acid: design, asymmetric synthesis, and improved binding affinity to DNA and RNA. Org Lett., 5(15): 2695-8 (2003).
Nam et al., Nanoparticle-based bio-bar codes for the ultrasensitive detection of proteins. Science, 301: 1884-6 (2003).
Nielsen et al., Sequence-selective recognition of DNA by strand displacement with a thymine-substituted polyamide. Science, 254: 1497-500 (1991).
Nitin et al., Peptide-linked molecular beacons for efficient delivery and rapid mRNA detection in living cells. Nucl. Acids Res., 32: e58 (2004).
Nitin, et al. "Oligonucleotide-Coated Metallic Nanoparticles as a Flexible Platform for Molecular Imaging Agents," Bioconjugate Chem. 18:2090-2096 (2007).
Nuzzo et al., Spontaneously organized molecular assemblies. 3. Preparation and properties of solution adsorbed monolayers of organic disulfides on gold surfaces. J. Am. Chem. Soc., 109(8): 2358-68 (1987).
Nykypanchuk et al., DNA-guided crystallization of colloidal nanoparticles. Nature, 451: 549-52 (2008).
O'Meara et al., Capture of single-stranded DNA assisted by oligonucleotide modules. Anal. Biochem., 255: 195-203 (1998).
O'Reilly et al., Identification of an activating transcription factor (ATF) binding site in the human transforming growth factor-beta 2 promoter. J. Biol. Chem., 267: 19938-43 (1992).

(56) References Cited

OTHER PUBLICATIONS

Ohishi et al., Hepatocellular carcinoma detected by iodized oil. Use of anticancer agents, Radiology, 154(1):25-9 (1985).
Ohuchi et al., In vitro method for the generation of protein libraries using PCR amplification of a single DNA molecule and coupled transcription/translation, Nucl. Acids Res., 26: 4339-46 (1998).
Okayasu et al., Selective and persistent deposition and gradual drainage of iodized oil, Lipiodol in the hepatocellular carcinoma after injection into the feeding hepatic artery, Am. J. Clin. Pathol., 90(5):536-44 (1988).
Olshaysky et al., Organometallic synthesis of gallium-arsenide crystallites, exhibiting quantum confinement. J. Am. Chem. Soc., 112(25): 9438-9 (1990).
Ono et al., DNA triplex formation of oligonucleotide analogues consisting of linker groups and octamer segments that have opposite sugar-phosphate backbone polarities. Biochemistry, 30(41): 9914-2 (1991).
Opalinska et al., Nucleic-acid therapeutics: basic principles and recent applications. Nat. Rev. Drug Discov., 1: 503-14 (2002).
Ow Sullivan et al., Development of a novel gene delivery scaffold utilizing colloidal gold-polyethylenimine conjugates for DNA condensation. Gene Ther., 10(22): 1882-90 (2003).
Ozpolat et al., Nanomedicine based approaches for the delivery of siRNA in cancer, J. Intern. Med., 267(1):44-53 (2010).
Paciotti et al., Colloidal gold: a novel nanoparticle vector for tumor directed drug delivery, Drug Deliv., 11(3):169-83 (2004).
Parak et al., Biological applications of colloidal nanocrystals, Nanotechnol., 14: R15-27 (2003).
Pardridge, Blood-brain barrier biology and methodology, J. Neurovirol., 5(6):556-69 (1999).
Pardridge, Molecular Trojan horses for blood-brain barrier drug delivery, Curr. Opin. Pharmacol., 6(5):494-500 (2006).
Park et al., Array-based electrical detection of DNA with nanoparticle probes. Science, 295: 1503-6 (2002).
Park et al., DNA-programmable nanoparticle cystrallization. Nature, 451: 553-6 (2008).
Park et al., Gold nanoparticles functionalised by Gd-complex of DTPA-bis(amide) conjugate of glutathione as an MRI contrast agent, Bioorg. Med. Chem. Lett, 18(23):6135-7 (2008).
Parrish et al., Functional anatomy of a dsRNA trigger: Differential requirement for the two trigger strands in RNA interference. Mol. Cell, 6: 1077-87 (2000).
Patel et al., Peptide antisense nanoparticles. Proc. Natl. Acad. Sci. USA, 105: 17222-6 (2008).
Patel et al., Scavenger receptors mediate cellular uptake of polyvalent oligonucleotide-functionalized gold nanoparticles, Bioconjug. Chem., 21(12):2250-6 (2010).
Patil et al., DNA-based therapeutics and DNA delivery systems: a comprehensive review. AAPS J., 7(1): E61-77 (2005).
Paunecku et al., Godolinium-conjugated TiO2-DNA oligonucleotide nanocanjugates show prolonged intracellular retention period and T1-weighted contract enhancement in magnetic resonance images. *Nanomedicine*, 4(3): 201-7 (2008).
Peng et al., Real-time detection of gene expression in cancer cells using molecular beacon imaging: New strategies for cancer research. Cancer Res., 65: 1909-17 (2005).
Penn et al., Nanoparticles for bioanalysis. Curr. Opin. Chem. Biol., 7: 609-15 (2003).
Peracchi, Prospects for antiviral ribozymes and deoxyribozymes. Rev. Med. Virol., 14: 47-64 (2004).
Perlette et al., Real-time monitoring of intracellular mRNA hybridization inside single living cells. Anal. Chem., 73: 5544-50 (2001).
Pon, Solid-phase supports for oligonucleotide synthesis. *Meth. Molec. Biol.*, 20: 465-96 (1993).
Prausnitz et al., Microneedles for transdermal drug delivery, Adv. Drug Delivery Rev., 56:581-7 (2004).
Prausnitz et al., Transdermal drug delivery, Nat. Biotechnol., 26: 1261-8 (2008).
Prigodich et al., Nano-flares for mRNA regulation and detection. ACS Nano, 3: 2147-52 (2009).
Prime et al., Self-assembled organic monolayers; Model systems for studing adsorption of proteins at surfaces. Science, 252: 1164-7 (1991).
Raj et al., Stochastic mRNA synthesis in mammalian cells. PLoS Biol., 4(10): e309 (2006).
Rapoport, Blood Brain Barrier in Physiology and Medicine, New York: Raven Press (1976).
Rethore et al., Preparation of chitosan/polyglutamic acid spheres based on the use of polystyrene template as nonviral gene carrier. *Tissue Engineering*, 15(4): 605-13 (2009).
Rethore et al., Use of templates to fabricate nanoscale spherical structures for defined architectural control, Small, 6(4):488-98 (2010).
Riccelli et al., Hybridization of single-stranded DNA targets to immobilized complementary DNA probes: comparison of hairpin versus linear capture probes. Nucl. Acids Res., 29: 996-1004 (2001).
Richardson et al., Tethered oligonucleotide probes. A strategy for the recognition of structured RNA. J. Am. Chem. Soc., 113(13): 5109-11 (1991).
Rihova et al., Receptor-mediated targeted drug or toxin delivery. Adv. Drug Deliv. Rev., 29(3): 273-89 (1998).
Rizzo et al., Chimeric RNA-DNA molecular beacon assay for ribonuclease H activity. Mol. Cell Probes, 16: 277-83 (2002).
Rosi et al., Nanostructures in biodiagnostics. Chem Rev., 105(4): 1547-62 (2005).
Rosi et al., Oligonucleotide-modified gold nanoparticles for intracellular gene regulation. Science, 2312(5776): 1027-30 (2006).
Sadauskas et al., Protracted elimination of gold nanoparticles from mouse liver, Nanomedicine, 5(2):162-9 (2009).
Sambrook et al., Molecular Cloning: A Laboratory Manual, 2nd Edition, Table of Contents, pp. v-xxxii (1989).
Sandhu et al., Gold nanoparticle-mediated transfection of mammalian cells. Bioconjugate Chem., 13: 3-6 (2002).
Sanghvi et al., Heterocyclic base modifications in nucleic acids and their applications in antisense oligonucleotides, Chapter 15 In: Crooke et al. (Eds.), Antisense Research and Applications, Boca Raton: CRC Press (1993).
Santangelo et al., Dual FRET molecular beacons for mRNA detection in living cells. Nucl. Acids Res., 32:e57 (2004).
Santangelo et al., Nanostructured probes for RNA detection in living cells. Ann. Biomed. Eng., 34:39-50 (2006).
Sapra et al., Ligand-targeted liposomal anticancer drugs, Prog. Lipid Res., 42:439-62 (2003).
Schifferlers et al., Cancer siRNA therapy by tumor selective delivery with ligand-targeted sterically stabilized nanoparticle. *Nucl. Acid Res.*, 32(19): e149 (2004).
Schmid, G. (ed.) *Clusters and Colloids* (VCH, Weinheim, 1994).
Seela et al., Oligodeoxyribonucleotides containing 1,3-propanediol as nucleoside substitute. Nucl. Acids Res., 15(7): 3113-29 (1987).
Seelig et al., Catalyzed relaxation of a metastable DNA fuel. J. Am. Chem. Soc., 128: 12211-20 (2006).
Seferos et al., Locked nucleic acid-nanoparticle conjugates. Chembiochem., 8: 1230-2 (2007).
Seferos et al., Nano-flares: probes for transfection and mRNA detection in living cells. J. Am. Chem. Soc., 129: 15477-9 (2007).
Seferos et al., Polyvalent DNA nanoparticle conjugates stabilize nucleic acids. Nano Lett., 9:308-11 (2009).
Sharma et al., Characterization of MRI contrast agent-loaded polymeric nanocapsules as versatile vehicle for targeted imaging, Contrast Media Mol. Imaging, 5(2):59-69 (2010).
Sharma et al., Mutant V599EB-Raf regulates growth and vascular development of malignant melanoma tumors. Cancer Res., 65: 2412-21 (2005).
Sharma et al., Targeting Akt3 signaling in malignant melanoma using isoselenocyanates. Clin. Cancer Res., 15:.1674-85 (2009).
Sharma et al., Targeting mitogen-activated protein kinase/extracellular signal-regulated kinase kinase in the mutant (V600E) B-Raf signaling cascade effectively inhibits melanoma lung metastases. Cancer Res., 66: 8200-9 (2006).
Sharp et al., RNA interference—2001. Genes Dev., 15: 485-90 (2001).

(56) References Cited

OTHER PUBLICATIONS

Shu et al., Gradient cross-linked biodegradable polyelectrolyte nanocapsules for intracellular protein drug delivery, Biomaterials, 31(23):6039-49 (2010).
Simmel et al., DNA nanodevices. Small, 1: 284-99 (2005).
Skwarczynski et al., Paclitaxel prodrugs: toward smarter delivery of anticancer agents, J. Med. Chem., 49(25):7253-69 (2006).
Smith et al., Bioconjugated quantum dots for in vivo molecular and cellular imaging, Adv. Drug Deliv. Rev., 60(11):1226-40 (2008).
Sokol et al., Real time detection of DNA.RNA hybridization in living cells. Proc. Natl. Acad. Sci. USA, 95: 11538-43 (1998).
Sonavane et al., Biodistribution of colloidal gold nanoparticles after intravenous administration: effect of particle size, Colloids and Surfaces B: Biointerfaces, 66:274-80 (2008).
Song et al., Synthesis of multimeric MR contrast agents for cellular imaging, J. Am. Chem. Soc., 130(21):6662-3 (2008).
Soriaga et al., Determination of the orientation of aromatic molecules adsorbed on platinum electrodes. The effect of solute concentration. J. Am. Chem. Soc., 104: 3937-45 (1982).
Srivastava et al., Use of riboprobes for northern blotting analysis. Biotechniques, 11(5): Abstract (1991).
Stahl et al., Deregulated Akt3 activity promotes development of malignant melanoma, Cancer Res., 64: 7002-10 (2004).
Stegh et al., Bcl2L12 inhibits post-mitochondrial apoptosis signaling in glioblastoma, Genes Dev., 21(1):98-111 (2007).
Stegh et al., Bcl2L12-mediated inhibition of effector caspase-3 and caspase-7 via distinct mechanisms in glioblastoma, Proc. Natl. Acad. Sci. USA, 105(31):10703-8 (2008).
Stephenson et al., Inhibition of Rous sarcoma viral RNA translation by a specific oligodeoxyribonucleotide. Proc. Natl. Acad. Sci. USA, 75(1): 285-8 (1978).
Stoermer et al., Distance-dependent emission from dye-labeled oligonucleotides on striped Au/Ag nanowires: effect of secondary structure and hybridization efficiency. J. Am. Chem. Soc., 128: 13243-54 (2006).
Stoeva et al., Multiplexed detection of protein cancer markers with biobarcoded nanoparticle probes. J. Am. Chem. Soc., 128: 8378-9 (2006).
Storhoff et al., One-pot colorimetric differentiation of polynucleotides with single base imperfections using gold nanoparticle probes, J. Am. Chem. Soc., 120:1959-64 (1998).
Storhoff et al., What controls the optical properties of DNA-linked gold nanoparticle assemblies? J. Am. Chem. Soc., 122: 4640-50 (2000).
Storz et al., An abundance of RNA regulators, Annu. Rev. Biochem., 74:199-217 (2005).
Sugihara et al., One-pot synthesis of biomimetic shell cross-linked micelles and nanocages by ATRP in alcohol/water mixtures, Angew. Chem. Int. Ed. Engl., 48(20):3500-3 (2010).
Sun et al., Ganglioside loss promotes survival primarily by activating integrin-linked kinase/Akt without phosphoinositide 3-OH kinase signaling. J. Invest. Dermatol., 119: 107-17 (2002).
Sundaram et al., Particle-mediated delivery of recombinant expression vectors to rabbit skin induces high-titered polyclonal antisera (and circumvents purification of a protein immunogen). Nucl. Acids Res., 24(7): 1375-7 (1996).
Tan et al., Facile synthesis of hybrid silica nanocapsules by interfacial templating condensation and their application in fluorescence imaging, Chem. Commun. (Camb.), Nov. 7(41):6240-2 (2009).
Taton et al., Scanometric DNA array detection with nanoparticle probes, Science, 289(5485):1757-60 (2000).
Thomas et al., Conjugation to gold nanoparticles enhances polyethylenimine's transfer of plasmid DNA into mammalian cells. Proc. Natl. Acad. Sci. USA, 100(16): 9138-43 (2003).
Thomas et al., The interaction of HgCl2 with sodium thymonucleate. *J. Am. Chem. Soc.*, 76:6032-4 (1954).
Thompkins et al., The study of the gas-solid interaction of acetic acid with a cuprous oxide surface using reflection-absorption spectroscopy. J. Colloid Interface Sci., 49: 410-21 (1974).
Thurn et al., Labeling Ti02 nanoparticles with dyes for optical fluorescence microscopy and determination of Ti02-DNA nanoconjugate stability. *Small*, 5(11): 1318-25 (2009).
Timmons et al., Investigation of fatty acid monolayers on metals by contact potential measurements. J. Phys. Chem., 69(3): 984-90 (1965).
Tkachenko et al., Cellular trajectories of peptide-modified gold particle complexes: comparison of nuclear localization signals and peptide transduction domains. Bioconjugate Chem., 15(3):482-90 (2004).
Tkachenko et al., Multifunctional gold nanoparticle-peptide complexes for nuclear targeting. J. Am. Chem. Soc., 125: 4700-1 (2003).
Tondelli, et al., Highly efficient cellular uptake of c-myb antisense oligonucleotides through specifically designed polymeric nanospheres. Nucl. Acids Res., 26: 5425-31 (1998).
Treisman, The SRE: a growth factor responsive transcriptional regulator. *Semin. Cancer Biol.*, 1: 47-58 (1990).
Tsao et al., Genetic interaction between NRAS and BRAF mutations and PTEN/MMAC1 inactivation in melanoma. J. Invest. Dermatol., 122: 337-41 (2004).
Tsuji et al., Carrier-mediated or specialized transport of drugs across the blood-brain barrier, Adv. Drug Deliv. Rev., 36(2-3):277-90 (1999).
Tuerk et al., Systematic evolution of ligands by exponential enrichment: RNA ligands to bacteriophage T4 DNA polymerase. Science, 249: 505-10 (1990).
Turberfield et al., DNA fuel for free-running nanomachines. Phys. Rev. Lett., 90: 118102 (2003).
Turner et al., Nanoscale Cage-like Structures Derived from Polyisoprene-Containing Shell Cross-linked Nanoparticle Templates, Nano Lett., 4(4):683-8 (2004).
Tyagi et al., Molecular beacons: Probes that fluoresce upon hybridization. Nat. Biotechnol., 14: 303-8 (1996).
Uchida et al., GaAs nanocrystals prepared in quinoline. J. Phys. Chem. 95(14): 5382-4 (1991).
Vasiliskov et al., Parallel multiplex thermodynamic analysis of coaxial base stacking in DNA duplexes by oligodeoxyribonucleotide microchips. Nucl. Acids Res., 29: 2303-13 (2001).
Virmani et al., Comparison of two different methods for inoculating VX2 tumors in rabbit livers and hind limbs, J. Vasc. Interv. Radiol., 19(6):931-6 (2008).
Wagner et al., Gene inhibition using antisense oligodeoxynucleotides. Nature, 372: 333-5 (1994).
Wang et al., Ganglioside GM3 inhibits matrix metalloproteinase-9 activation and disrupts its association with integrin, J. Biol. Chem., 278: 25591-9 (2003).
Wang et al., Ganglioside GM3 promotes carcinoma cell proliferation via urokinase plasminogen activator-induced extracellular signal-regulated kinase-independent p70S6 kinase signaling, J. Invest. Dermatol., 126: 2687-96 (2006).
Wang et al., Inhibition of integrin-linked kinase/protein kinase B/Akt signaling: mechanism for ganglioside-induced apoptosis. J. Biol. Chem., 276: 44504-11 (2001).
Wang et al., Locked nucleic acid molecular beacons. J. Am. Chem. Soc., 127: 15664-5 (2005).
Wang et al., Molecular engineering of DNA: molecular beacons. Angew. Chem., Int. Ed., 48: 856-70 (2009).
Wang et al., Nanometer-sized semiconductor clusters: materials synthesis, quantum size effects, and photophysical properties. J. Phys. Chem., 95(2): 525-32 (1991).
Wang et al., Nanoparticles for multiplex diagnostics and imaging. Nanomedicine (Lond.), 1: 413-26 (2006).
Wang et al., Speeding up a single-molecule DNA device with a simple catalyst. Phys. Rev. E Stat. Nonlin. Soft Matter. Phys., 72: 051918 (2005).
Wang et al., Superparamagnetic sub-5 nm Fe@C nanoparticles: isolation, structure, magnetic properties, and directed assembly, Nano Lett., 8(11):3761-5 (2008).
Warnmark et al., Activation functions 1 and 2 of nuclear receptors: molecular strategies for transcriptional activation, Mol. Endocrinol., 17(10):1901-9 (2003).

(56) References Cited

OTHER PUBLICATIONS

Wasserman et al., Structure and reactivity of alkylsiloxane monolayers formed by reaction of alkyltrichlorosilanes on silicon substrates. Langmuir, 5(4): 1074-87 (1989).
Watson et al. (Eds.), *Molecular Biology of the Gene*, 4th ed., The Benjamin/Cummings Publishing Company Inc. (1987).
Wei et al., A study of the relationships between oligonucleotide properties and hybridization signal intensities from NimbleGen microarray datasets. Nucl. Acids Res., 36: 2926-38 (2008).
Wellbrock et al., V599EB-RAF is an oncogene in melanocytes. Cancer Res., 64: 2338-42 (2004).
Weller, Colloidal Semiconductor Q-particles: Chemistry in the transition region between solid state and molecules. Angew. Chem. Int. Ed. Engl., 32(1): 41-53 (1993).
Whitesides, Proceedings of the Robert A. Welch Foundation 39th Conference on Chemical Research Nanophase Chemistry, Houston, Tex., pp. 109-121 (1995).
Wikipedia entry on Aspirin, Last modified on Oct. 6, 2010 (online). Retrieved on Oct. 7, 2010). Retrieved from the Internet: <URL: http://en.wikipedia.org/wiki/Aspirin>.
Wikipedia entry on Phenylbutazone. Last modified on Sep. 20, 2010. Online. (Retrieved on Oct. 7, 2010). Retrieved from the Internet: <URL:http://en.wikipedia.org/wiki/Phenylbutazone>.
Wikipedia entry on Warfarin. Last modified on Oct. 5, 2010. (Online) (Retrieved on Oct. 8, 2010). Retrieved from the Internet: <URL:http://en.wikpedia.org/wiki/Warfarin>.
Winter et al., Molcular imaging by MRI, Curr. Cardiol. Rep. 8(1):65-9 (2006).
Wolf et al., Rapid hybridization kinetics of DNA attached to submicron latex particles. Nucl. Acids Res., 15: 2911-26 (1987).
Xia, Nanomaterials at work in biomedical research, Nat. Mater., 7(10):758-60 (2008).
Xu et al., A gold-nanoparticle-based real-time colorimetric screening method for endonuclease activity and inhibition, Angew. Chem. Int. Ed. Engl., 46(19):3468-70 (2007).
Xu et al., Homogeneous detection of nucleic acids based upon the light scattering properties of silver-coated nanoparticle probes, Anal. Chem., 79(17):6650-4 (2007).
Xu et al., Thermodynamics of DNA hybridization on gold nanoparticles. J. Am. Chem. Soc., 127(38): 13227-31 (2005).
Yamane et al., On the complexing of desoxyribonucleic acid (DNA) by mercuric ion. J. Am. Chem. Soc., 83: 2599-607 (1961).
Yan et al., Aptamers and aptamer targeted delivery. RNA Biol., 6: 316-20 (2009).
Yang et al., Evidence that processed small dsRNAs may mediate sequence-specific mRNA degradation during RNAi in *Drosophila* embryos. Curr. Biol., 10: 1191-200 (2000).
Ye et al., Characterization of a silencer regulatory element in the human interferon-gamma promoter. J. Biol. Chem., 269: 25728-34 (1994).
Yin Win et al., Effects of particle size and surface coating on cellular uptake of polymeric nonparticles for oral delivery of anticancer drugs. Biomaterials, 26: 2713-22 (2005).
You et al., Detection and identification of proteins using nanoparticle-fluorescent polymer 'chemical nose' sensors. Nat. Nanotechnol., 2: 318-23 (2007).
You et al., Engineering the nanoparticle-biomacromolecule interface. Soft Matter, 2: 190-204 (2006).
Zabner et al., Cellular and molecular barriers to gene transfer by a cationic lipid. J. Biol. Chem., 270: 18997-9007 (1995).
Zamecnik et al., Inhibition of Rous sarcoma virus replication and cell transformation by a specific oligodeoxynucleotide. Proc. Natl. Acad. Sci. USA, 75(1): 280-4 (1978).
Zamore et al., RNAi: double-stranded RNA directs the ATP-dependent cleavage of mRNA at 21 to 23 nucleotide intervals. Cell, 101: 25-33 (2000).
Zhang et al., A novel paclitaxel-loaded poly(epsilon-caprolactone)/Poloxamer 188 blend nanoparticle overcoming multidrug resistance for cancer treatment, Acta Biomater., 6(6):2045-52 (2010).
Zhang et al., An extremely stable and orthogonal DNA base pair with a simplifed three-carbon backbone. J. Am. Chem. Soc., 127: 74-5 (2005).
Zhang et al., Cationic shell-crosslinked knedel-like nanoparticles for highly efficient gene and oligonucleotide transfection of mammalian cells, Biomaterials, 30(5):968-77 (2009).
Zhang et al., Control of DNA strand displacement kinetics using toehold exchange. J. Am. Chem. Soc., 131: 17303-14 (2009).
Zhang et al., Nanopod formation through gold nanoparticle templated and catalyzed cross-linking of polymers bearing pendant propargyl ethers, J. Am. Chem. Soc., 132(43):15151-3 (2010).
Zhang et al., PowerBLAST: a new network BLAST application for interactive or automated sequence analysis and annotation, Genome Res., 7(6):649-56 (1997).
Zhang et al., PowerBlast: A new network BLAST application for interactive or automated sequence analysis and annotation. Genome, 7: 649-56 (1997).
Zhang et al., Self-assembled monolayers of terminal alkynes on gold, J. Am. Chem. Soc., 129(16):4876-7 (2007).
Zhang et al., Single-quantum-dot-based DNA sensor. Nat. Mater., 4: 826-31 (2005).
Zhao et al., A rapid bioassay for single bacterial cell quantitation using bioconjugated nanoparticles, Proc. Natl. Acad. Sci. USA, 101 (42):15027-32 (2004).
Zheng et al., Aptamer nano-flares for molecular detection in living cells. Nano Lett., 9: 3258-61 (2009).
Zimmer, Antisense oligonucleotide delivery with polyhexylcyanoacrylate nanoparticles as carriers. Methods, 18: 286-95 (1999).
Zimmerman et al., A novel silver(I)-mediated DNA base pair. J. Am. Chem. Soc., 124: 13684-5 (2002).
Gaillard, et al. "Diphtheria toxin receptor-targeted brain drug delivery," Int Congress Series 1277:185-198 (2005).
Pardridge, "The Blood-Brain Barrier: Bottleneck in Brain Drug Development," The American Society for Experimental NeuroTherapeutics, Inc., 2:3-14 (2005).
Remington's Pharmaceutical Sciences (1980).
Song, et al. "Multimodal Gadolinium-Enriched DNA-Gold Nanoparticle Conjugates for Cellular Imaging," Angew. Chem. Int. Ed. 48:9143-9147 (2009).

* cited by examiner

Figure 3A
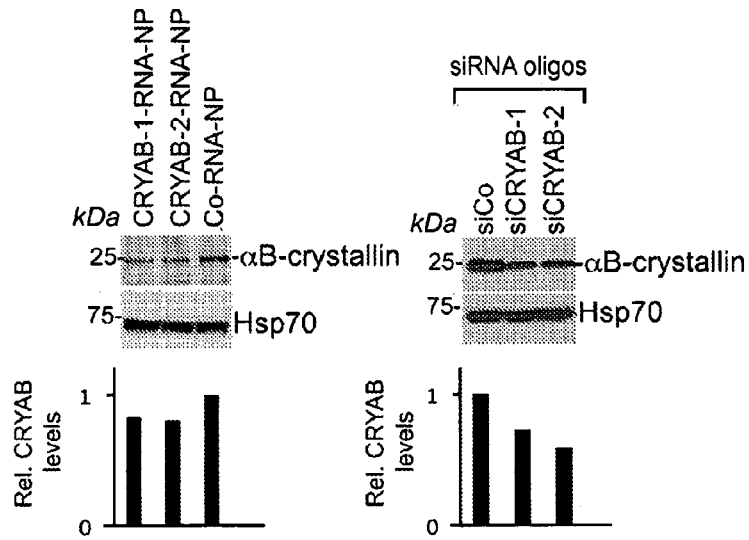
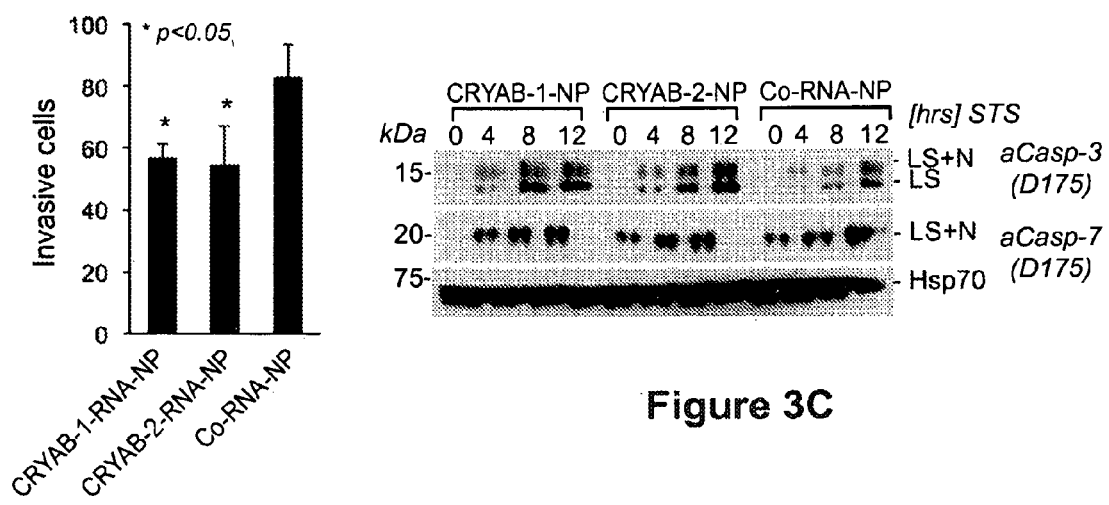
Figure 3B
Figure 3C

NANOCONJUGATES ABLE TO CROSS THE BLOOD-BRAIN BARRIER

CROSS REFERENCE TO RELATED APPLICATIONS

This application is a U.S. National Phase of International Application No. PCT/US2012/055635 filed Sep. 14, 2012, incorporated herein by reference, which claims the priority benefit under 35 U.S.C. §119(e) of U.S. Provisional Application No. 61/534,853, filed Sep. 14, 2011, the disclosure of which is incorporated herein by reference in its entirety.

STATEMENT OF GOVERNMENT INTEREST

This invention was made with government support under Grant Number U54 CA151880 awarded by the National Institutes of Health/National Cancer Institute. The government has certain rights in the invention.

FIELD OF THE INVENTION

The present disclosure is directed to nanoconjugates that cross the blood-brain barrier and methods of their therapeutic use.

BACKGROUND OF THE INVENTION

The brain is unique in allowing only select access to molecules. While this is a useful protective mechanism, it also prevents potentially beneficial molecular agents from gaining access to the central nervous system (CNS), and as such, the molecular agents are unable to exert a therapeutic effect in many neurological disorders or other conditions of the CNS.

The blood-brain barrier (BBB) performs a neuroprotective function by tightly controlling access to the brain; consequently it also impedes access of pharmacological agents to cerebral tissues, necessitating the use of vectors for their transit. Blood-brain barrier (BBB) permeability is frequently a rate-limiting factor for the penetration of drugs or peptides into the CNS [Pardridge, Neurovirol. 5: 556-569 (1999); Bickel et al., Adv. Drug Deliv. Rev. 46: 247-279 (2001)]. The brain is shielded against potentially toxic substances by the BBB, which is formed by brain capillary endothelial cells that are closely sealed by tight junctions. In addition, brain capillaries possess few fenestrae and few endocytic vesicles, compared to the capillaries of other organs [Pardridge, Neurovirol. 5: 556-569 (1999)]. There is little transit across the BBB of large, hydrophilic molecules aside from some specific proteins such as transferrin, lactoferrin and low-density lipoproteins, which are taken up by receptor-mediated transcytosis (RMT) [Pardridge, Neurovirol. 5: 556-569 (1999); Tsuji et al., Adv. Drug Deliv. Rev. 36: 277-290 (1999); Kusuhara et al., Drug Discov. Today 6: 150-156 (2001); Dehouck et al. J. Cell. Biol. 138: 877-889 (1997); and Fillebeen et al., J. Biol. Chem. 274: 7011-7017 (1999)].

Malignant glioma (MG) represent the most prevalent and lethal primary cancer of the central nervous system. Patients diagnosed with the highest grade MG, grade IV glioblastoma multiforme (GBM), survive for only 9-12 months after diagnosis despite surgical resection and aggressive treatment regimens. Multimodal approaches using radiation with conjunctive chemotherapy (temozolamide (TMZ)) resulted in only marginal increase in patients' survival up to 14.6 months. Furthermore, recurrence is nearly universal and salvage therapies for such progression remain ineffective. GBM remains a highly enigmatic and incurable disease particularly due to a highly therapy-resistant cancer stem cell population (brain tumor stem cell, BTSC) and an incomplete understanding of how catalogued genetic aberrations dictate phenotypic hallmarks of the disease. It is highly resistant even to intense therapy (apoptosis) despite florid intratumoral necrogenesis. The continued lack of success in treating high-grade gliomas with targeted receptor tyrosine kinase inhibitors, which have been proven to be effective in other malignancies, has prompted a reevaluation of all aspects of glioma drug development and underlined the overarching need to develop an innovative technological platform and refine cell culture-based and in vivo model systems to combat the disease.

SUMMARY OF THE INVENTION

Polyvalent nanoconjugates address the critical challenges described above on multiple levels. The single-entity, targeted therapeutic is able to cross the blood-brain barrier (BBB) and is thus effective in the treatment of central nervous system (CNS) disorders. Further, despite the tremendously high cellular uptake of nanoconjugates, they exhibit no toxicity in the cell types tested thus far (see Table 1, below). This property is critical for therapeutic agent delivery applications for reducing off-target effects.

TABLE 1

| Cell Type | Designation or Source |
| --- | --- |
| Breast | SKBR3, MDA-MB-321, AU-565 |
| Brain | U87, LN229 |
| Bladder | HT-1376, 5637, T24 |
| Colon | LS513 |
| Cervix | HeLa, SiHa |
| Skin | C166, KB, MCF, 10A |
| Kidney | MDCK |
| Blood | Sup T1, Jurkat |
| Leukemia | K562 |
| Liver | HepG2 |
| Kidney | 293T |
| Ovary | CHO |
| Macrophage | RAW 264.7 |
| Hippocampus Neurons | primary, rat |
| Astrocytes | primary, rat |
| Glial Cells | primary, rat |
| Bladder | primary, human |
| Erythrocytes | primary, mouse |
| Peripheral Blood Mononuclear Cell | primary, mouse |
| T-Cells | primary, human |
| Beta Islets | primary, mouse |
| Skin | primary, mouse |

While some of the cell types shown in Table 1 are cells of the brain/nervous system, the data was gathered from in vitro experiments.

In one aspect, the disclosure provides a composition comprising a nanoconjugate, the nanoconjugate comprising a polynucleotide that is sufficiently complementary to a target polynucleotide which encodes a polypeptide specifically expressed in a central nervous system (CNS) disorder, the nanoconjugate having the ability to cross the blood-brain barrier (BBB). In some embodiments, the composition further comprises a targeting moiety. In various embodiments, the disorder is caused by aberrant gene expression. In some embodiments, the composition further comprises a therapeutic agent, and in further embodiments, the therapeutic agent is temozolamide. In some embodiments, the nanoconjugate further comprises, a targeting moiety and/or a therapeutic agent.

In further embodiments, it is contemplated that the disorder is acute and/or chronic.

In some embodiments, the acute disorder is selected from the group consisting of focal brain ischemia, global brain ischemia, brain trauma, spinal cord injury, acute infections, status epilepticus, migraine headache, acute psychosis, suicidal depression and acute anxiety/phobia, and injury related maladies, including but not limited to traumatic brain injury and swelling. In further embodiments, the chronic disorder is selected from the group consisting of chronic neurodegeneration, retinal degeneration, depression, chronic affective disorders, lysosmal storage disorders, chronic infections of the brain, brain cancer, stroke rehabilitation, inborn errors of metabolism, autism, and mental retardation.

In further embodiments, the nanoconjugate has a mass that is at least about 400, about 600, about 800, about 1000, about 1200 or more Daltons. In some embodiments, the nanoconjugate has a mass that is at least about 1, about 2, about 3, about 5, about 10, about 20, about 30, about 40, about 50, about 60, about 70, about 80, about 90, about 100, about 200, about 500, about 700, about 900 or more kilodaltons.

In some embodiments, a nanoconjugate of the disclosure possesses a zeta potential (surface charge) measurement of from about −10 millivolts (mV) to about −50 millivolts (mV). In further embodiments, the nanoconjugate possesses a zeta potential measurement of from about −10 mV to about −40 mV, or from about −10 mV to about −30 mV, or from about −20 mV to about −50 mV, or from about −20 mV to about −40 mV, or from about −30 mV to about −45 mV, or from about −30 mV to about −50 mV. In some embodiments, the nanoconjugate possesses a zeta potential measurement of about −10 mV, about −15 mV, about −20 mV, about −25 mV, about −30 mV, about −35 mV, about −40 mV, about −45 mV, about −50 mV or about −60 mV.

In one aspect, the disclosure provides a method of treating a patient in need of a composition that is able to traverse the blood-brain barrier, comprising administering to the patient a therapeutically effective amount of a composition comprising a functionalized nanoconjugate, the nanoconjugate comprising a polynucleotide having a sequence sufficiently complementary to a target polynucleotide to hybridize to and inhibit expression of the target polynucleotide. In any of the aspects or embodiments of the disclosure, it is contemplated that the patient is a human.

In another aspect, the disclosure provides a method of administering a composition comprising a functionalized nanoconjugate to a patient, the method comprising administering to the patient a therapeutically effective amount of the composition; wherein the nanoconjugate comprises a polynucleotide having a sequence sufficiently complementary to a target polynucleotide to hybridize to and inhibit expression of the target polynucleotide, said composition having the ability to traverse the blood-brain barrier, and wherein the patient is in need of a composition that is able to traverse the blood-brain barrier.

In any of the aspects or embodiments of the disclosure, a composition as described herein further comprises a therapeutic agent. In any of the aspects or embodiments of the disclosure, the patient suffers from a central nervous system (CNS) disorder. In any of the aspects or embodiments of the disclosure, the patient suffers from a disorder caused by aberrant gene expression.

In some embodiments, the patient suffers from an acute and/or chronic disorder. In embodiments where the patient suffers from an acute disorder, it is further contemplated that the acute disorder is selected from the group consisting of focal brain ischemia, global brain ischemia, brain trauma, spinal cord injury, acute infections, status epilepticus (SE), migraine headache, acute psychosis, suicidal depression and acute anxiety/phobia, and injury related maladies, including but not limited to traumatic brain injury and swelling.

In embodiments where the patient suffers from a chronic disorder, it is further contemplated that the chronic disorder is selected from the group consisting of chronic neurodegeneration, retinal degeneration, depression, chronic affective disorders, lysosmal storage disorders, chronic infections of the brain, brain cancer, stroke rehabilitation, inborn errors of metabolism, autism, and mental retardation.

In some embodiments, a composition of the disclosure is administered only once. In some embodiments, a composition of the disclosure is administered at a frequency of no greater than about once per week.

In another aspect, the disclosure provides a package or kit comprising (a) a nanoconjugate or composition comprising a nanoconjugate, optionally in a container, (b) optionally an additional therapeutic agent; and (c) a package insert, package label, instructions or other labeling directing or disclosing any of the methods or embodiments disclosed herein.

BRIEF DESCRIPTION OF THE DRAWINGS

FIG. 3 shows neutralization of aB-crystallin in LN235 cells results in reduced invasive potential and increases susceptibility towards STS-instigated apoptosis. (A) LN235 cells were treated with aB-crystallin-targeting nanoconjugates or siRNAs, lysed and subjected to western blot analyses using aB-crystallin and Hsp70-specific antibodies. (B) CRYAB- and Co-RNA-nanoconjugate-treated cells were subjected to Matrigel invasion assays and numbers of invading cells were quantified by trypan blue staining. (C) Co-CRYAB-1- and CRYAB-2-RNA-nanoconjugate-treated LN235 cells were treated and analyzed as described in FIG. 2E. LS, large subunit; LS+N, large subunit+N peptide. Histograms quantify Bcl2L12 expression as assessed by densitometric analyses of corresponding western blots.

DETAILED DESCRIPTION OF THE INVENTION

Figure 1A:
FIG. 1 depicts Bcl2L12 expression (A) and RTK activation profile (B) in selected glioma, BTSC lines and explants.

The blood brain barrier is a limiting factor in the delivery of many peripherally-administered agents to the central nervous system. The present disclosure provides nanoconjugates that are able to cross the BBB, and retain their activity once across the BBB. Various aspects of the invention address these factors, by providing nanoconjugates that have one or more biomolecules associated therewith. In some embodiments, the nanoconjugate is further associated or co-administered with a therapeutic agent.

"Treatment" or "treating" as used herein includes achieving a therapeutic benefit and/or a prophylactic benefit. By therapeutic benefit is meant eradication or amelioration of the underlying disorder or condition being treated. For example, in an individual with a neurological disorder, therapeutic benefit includes partial or complete halting of the progression of the disorder, or partial or complete reversal of the disorder. Also, a therapeutic benefit is achieved with the eradication or amelioration of one or more of the physiological or psychological symptoms associated with the underlying condition such that an improvement is observed in the patient, notwithstanding the fact that the patient may still be affected by the condition. A prophylactic benefit of treatment includes prevention of a condition, retarding the progress of a condition (e.g., slowing the progression of a neurological disorder), or decreasing the likelihood of occurrence of a condition. As used herein, "treating" or "treatment" includes prophylaxis.

In some embodiments, a nanoconjugate is "administered peripherally" or "peripherally administered." As used herein, these terms refer to any form of administration of a nanoconjugate, optionally co-administered with a therapeutic agent, to an individual that is not direct administration to the CNS, i.e., that brings the agent in contact with the non-brain side of the blood-brain barrier. "Peripheral administration," as used herein, includes intravenous, subcutaneous, intramuscular, intraperitoneal, transdermal, inhalation, transbuccal, intranasal, rectal, and oral administration.

As used herein, "hybridization" means an interaction between two or three strands of nucleic acids by hydrogen bonds in accordance with the rules of Watson-Crick DNA complementarity, Hoogstein binding, or other sequence-specific binding known in the art. Hybridization can be performed under different stringency conditions known in the art. "Specifically hybridize," as used herein, is hybridization that allows for a stabilized duplex between polynucleotide strands that are complementary or substantially complementary. For example, a polynucleotide strand having 21 nucleotide units can base pair with another polynucleotide of 21 nucleotide units, yet only 19 bases on each strand are complementary or sufficiently complementary, such that the "duplex" has 19 base pairs. The remaining bases may, for example, exist as 5' and/or 3' overhangs. Further, within the duplex, 100% complementarity is not required; substantial complementarity is allowable within a duplex. Sufficient complementarity refers to 75% or greater complementarity. For example, a mismatch in a duplex consisting of 19 base pairs results in 94.7% complementarity, rendering the duplex sufficiently complementary.

The terms "therapeutically effective amount," as used herein, refer to an amount of a compound sufficient to treat, ameliorate, or prevent the identified disease or condition, or to exhibit a detectable therapeutic, prophylactic, or inhibitory effect. The effect can be detected by, for example, an improvement in clinical condition, or reduction in symptoms. The precise effective amount for a subject will depend upon the subject's body weight, size, and health; the nature and extent of the condition; and the therapeutic or combination of therapeutics selected for administration. Where a drug has been approved by the U.S. Food and Drug Administration (FDA), a "therapeutically effective amount" refers to the dosage approved by the FDA or its counterpart foreign agency for treatment of the identified disease or condition.

As used herein, a patient "in need of a composition that is able to traverse the blood-brain barrier" is a patient who would benefit from a composition that is able to traverse the blood-brain barrier. The patient may be suffering from any disease or condition for which therapy with a composition that is able to traverse the blood-brain bather may be useful in ameliorating symptoms.

A "disorder of the CNS" or "CNS disorder," as those terms are used herein, encompasses any condition that affects the brain and/or spinal cord and that leads to suboptimal function. In some embodiments, the disorder is an acute disorder. Acute disorders of the CNS include focal brain ischemia, global brain ischemia, brain trauma, spinal cord injury, acute infections, status epilepticus (SE), migraine headache, acute psychosis, suicidal depression, and acute anxiety/phobia. In some embodiments, the disorder is a chronic disorder. Chronic disorders of the CNS include chronic neurodegeneration, retinal degeneration, depression, chronic affective disorders, lysosmal storage disorders, chronic infections of the brain, brain cancer, stroke rehabilitation, inborn errors of metabolism, autism, mental retardation. Chronic neurodegeneration includes neurodegenerative diseases such as prion diseases, Alzheimer's disease (AD), Parkinson's disease (PD), Huntington's disease (HD), multiple sclerosis (MS), amyotrophic lateral sclerosis (ALS), transverse myelitis, motor neuron disease, Pick's disease, tuberous sclerosis, lysosomal storage disorders, Canavan's disease, Rett's syndrome, spinocerebellar ataxias, Friedreich's ataxia, optic atrophy, and retinal degeneration, and aging of the CNS.

As used herein, "concomitant use" is understood to be interchangeable with concurrent administration or co-administration. Thus, the terms are understood to encompass administration simultaneously, or at different times, and by the same route or by different routes, as long as the two agents are given in a manner that allows both agents to be affecting the body at the same time. For example, concomitant use can refer to a medication concomitantly administered, whether prescribed by the same or a different practitioner, or for the same or a different indication.

It is noted here that, as used in this specification and the appended claims, the singular forms "a," "an," and "the" include plural reference unless the context clearly dictates otherwise.

It is also noted that the term "about" as used herein is understood to mean approximately.

It is further noted that the terms "attached," "conjugated" and "functionalized" are used interchangeably herein and refer to the association of a polynucleotide, peptide, polypeptide, therapeutic agent, contrast agent and a combination thereof with a nanoconjugate.

The Blood-Brain Barrier (BBB)

As used herein, the "blood-brain barrier" (BBB) refers to the barrier between the peripheral circulation and the brain and spinal cord which is formed by tight junctions within the brain capillary endothelial plasma membranes, that creates a highly selective barrier that restricts the transport of molecules into the brain. The blood-brain barrier within the brain, the blood-spinal cord barrier within the spinal cord, and the blood-retinal barrier within the retina, are contiguous capillary barriers within the central nervous system (CNS), and are collectively referred to as the blood-brain barrier or BBB.

The BBB is formed by epithelial-like high resistance tight junctions within the endothelium of capillaries perfusing the vertebrate brain. Unless a therapeutic molecule is lipid-soluble with a molecular weight of 400-600 Daltons or less, brain penetration is limited [Pardridge, Curr Opin Pharmacol 6: 494-500 (2006)]. Because of the presence of the BBB, circulating molecules gain access to brain cells only via one of two processes: (i) lipid-mediated transport of small molecules through the BBB by free diffusion, or (ii) catalyzed transport. The latter includes carrier-mediated transport processes for low molecular weight nutrients and water soluble vitamins or receptor-mediated transport for circulating peptides (e.g., insulin), plasma proteins (e.g., transferrin), or viruses. While BBB permeability, per se, is controlled by the biochemical properties of the plasma membranes of the capillary endothelial cells, overall brain microvascular biology is a function of the paracrine interactions between the capillary endothelium and the other two major cells comprising the microcirculation of brain, i.e., the capillary pericyte, which shares the basement membrane with the endothelial cell, and the astrocyte foot process, which invests 99% of the abluminal surface of the capillary basement membrane in brain. Microvascular functions frequently ascribed to the capillary endothelium are actually executed by either the capillary pericyte or the capillary astrocyte foot process [Pardridge, J. Neurovir. 5: 556-569 (1999)].

The BBB largely defines the operating environment of the CNS by regulating the movement of substances between the blood and the CSF and brain interstitial fluid. The BBB is often divided into the vascular, or endothelial, barrier and the epithelial barrier at the choroid plexus (also termed the blood-CSF barrier). The endothelial cells that comprise the capillaries and line the arterioles and venules constitute the barrier function of the spinal cord and in most areas of the brain [Rapoport, *Blood Brain Barrier in Physiology and Medicine*, Raven Press, New York. (1976)]. The endothelial cells are modified in that circumferential belts of tight junctions between contiguous non-fenestrated endothelial cells of the CNS preclude the leakage found in the capillary beds of peripheral tissues. Intracellular tight junctions comparable to those of the brain endothelium exist between contiguous epithelial cells at the choroid plexus [Johanson, The choroid plexus-arachnoid membrane-cerebrospinal fluid system. In: *Neuronal Microenvironment*. Boulton A A, Baker G B, Walz W (eds). The Humana Press: Clifton, N.J., pp 33-104 (1988)] and between arachnoid mater cells [Balin et al., J Comp Neurol 251: 260-280 (1986)]. The brain endothelia have other modifications as well. They do engage in endocytosis of blood-borne macromolecules and a recycling of the luminal plasmalemma but to a lesser degree than peripheral endothelia and choroid plexus [Broadwell et al., Cell biological perspective for the transcytosis of peptides and proteins through the mammalian blood-brain fluid barriers. In: *The Blood-Brain Barrier*. Pardridge W M (ed). Raven Press Ltd: New York, pp 165-199 (1993)]. Secondary lysosomes hydrolyze many but not all macromolecules undergoing endocytosis within the BBB endothelia [Broadwell et al., Proc Natl. Acad Sci. USA 78: 7820-7824 (1981); Broadwell et al., Cell biological perspective for the transcytosis of peptides and proteins through the mammalian blood-brain fluid barriers. In: *The Blood-Brain Barrier*. Pardridge W M (ed). Raven Press Ltd: New York, pp 165-199 (1993)]. These modifications of the endothelia effectively eliminate the plasma ultrafiltrate characteristic of capillary beds in peripheral tissues and serve to define the restrictive permeability of the BBB [Banks, J. Neurovir. 5: 538-555 (1999)].

Therefore, most potentially therapeutic, diagnostic, or research molecules do not cross the BBB in pharmacologically active amounts. So as to bypass the BBB, invasive transcranial drug delivery strategies are used, such as intracerebro-ventricular (ICV) infusion, intracerebral (IC) administration, and convection enhanced diffusion (CED). Transcranial drug delivery to the brain is expensive, invasive, and largely ineffective. The ICV route typically delivers drugs only to the ependymal surface of the brain, not into brain parenchyma. The IC administration of a neurotrophin, such as nerve growth factor (NGF), only delivers drug to the local injection site, owing to the low efficiency of drug diffusion within the brain. The CED of neurotrophin results in preferential fluid flow through the white matter tracts of brain, which causes demyelination, and astrogliosis.

The present disclosure offers an alternative to these highly invasive and generally unsatisfactory methods for bypassing the BBB, allowing nanoconjugates to cross the BBB from the peripheral blood. It is based on the use of nanoconjugates that are able to transport a desired substance from the peripheral blood to the CNS. Given that brain penetration of a therapeutic agent that has a mass of 400-600 Daltons or more is limited, and further that the mass of a single base of DNA is approximately 320 daltons, it is unexpected that data presented herein demonstrates that a nanoconjugate that is functionalized with a multitude of polynucleotides, each comprising a multitude of bases, is able to cross the BBB in any appreciable quantity.

In one aspect, the disclosure provides compositions and methods that utilize a nanoconjugate capable of crossing the BBB. The compositions and methods are useful in transporting nanoconjugates and, optionally, a therapeutic agent, from the peripheral blood and across the blood brain barrier into the CNS.

Nanoconjugates

The compositions of the disclosure comprise a nanoconjugate. A nanoconjugate comprises a nanoparticle that is, in certain aspects, hollow. Nanoconjugates further comprise, in various embodiments, a biomolecule. As used herein, a "biomolecule" is understood to include a polynucleotide, peptide, polypeptide, small molecule, therapeutic agent, contrast agent, and a combination thereof. In various aspects of the nanoconjugate, all of the biomolecules are identical, or in the alternative, at least two biomolecules are different.

The nanoconjugates of the disclosure are not polymer-based nanoconjugates. Thus, nanoconjugates comprising, for example, polyethylene glycol (PEG)-coated hexadecylcyanoarcylate nanospheres; poly(butylcyanoacrylate) nanoparticles; poly(butylcyanoacrylate) nanoparticles coated with polysorbate 80; lipid nanoparticles; lipid nanoparticles consisting of emulsions of solidified oil nanodroplets loaded with, for example, iron oxide; or a nanogel consisting of cross-linked PEG and polyethylenimine are not contemplated aspects or embodiments of this disclosure.

The disclosure provides nanoconjugates that, in various embodiments, have a mass that is at least about 400, about 600, about 800, about 1000, about 1200 or more Daltons. In further embodiments, the nanoconjugate has a mass that is at least about 1, about 2, about 3, about 5, about 10, about 20, about 30, about 40, about 50, about 60, about 70, about 80, about 90, about 100, about 200, about 500, about 700, about 900 or more kilodaltons. As used herein, the mass of a nanoconjugate is understood to include the mass of a nanoparticle (if present) plus the mass of any biomolecules and/or therapeutic agent(s) that are associated with the nanoparticle.

Nanoparticle

Nanoparticles are provided which are functionalized, in some aspects, to have a biomolecule attached thereto. The size, shape and chemical composition of the nanoparticles contribute to the properties of the resulting functionalized nanoparticle. These properties include for example, optical properties, optoelectronic properties, electrochemical properties, electronic properties, stability in various solutions, magnetic properties, and pore and channel size variation. Mixtures of nanoparticles having different sizes, shapes and/or chemical compositions, as well as the use of nanoparticles having uniform sizes, shapes and chemical composition, and therefore a mixture of properties are contemplated. Examples of suitable particles include, without limitation, aggregate particles, isotropic (such as spherical particles), anisotropic particles (such as non-spherical rods, tetrahedral, and/or prisms) and core-shell particles, such as those described in U.S. Pat. No. 7,238,472 and International Publication No. WO 2003/08539, the disclosures of which are incorporated by reference in their entirety.

In one embodiment, the nanoparticle is metallic, and in various aspects, the nanoparticle is a colloidal metal. Thus, in various embodiments, nanoparticles of the invention include metal (including for example and without limitation, silver, gold, platinum, aluminum, palladium, copper, cobalt, indium, nickel, or any other metal amenable to nanoparticle formation), semiconductor (including for example and without limitation, CdSe, CdS, and CdS or CdSe coated with ZnS) and magnetic (for example, ferromagnetite) colloidal materials.

Also, as described in U.S. Patent Publication No 2003/0147966, nanoparticles of the invention include those that are available commercially, as well as those that are synthesized, e.g., produced from progressive nucleation in solution (e.g., by colloid reaction) or by various physical and chemical vapor deposition processes, such as sputter deposition. See, e.g., HaVashi, Vac. Sci. Technol. A5(4):1375-84 (1987); Hayashi, Physics Today, 44-60 (1987); MRS Bulletin, January 1990, 16-47. As further described in U.S. Patent Publication No 2003/0147966, nanoparticles contemplated are alternatively produced using $HAuCl_4$ and a citrate-reducing agent, using methods known in the art. See, e.g., Marinakos et al., Adv. Mater. 11:34-37 (1999); Marinakos et al., Chem. Mater. 10: 1214-19 (1998); Enustun & Turkevich, J. Am. Chem. Soc. 85: 3317 (1963).

Nanoparticles can range in size from about 1 nm to about 250 nm in mean diameter, about 1 nm to about 240 nm in mean diameter, about 1 nm to about 230 nm in mean diameter, about 1 nm to about 220 nm in mean diameter, about 1 nm to about 210 nm in mean diameter, about 1 nm to about 200 nm in mean diameter, about 1 nm to about 190 nm in mean diameter, about 1 nm to about 180 nm in mean diameter, about 1 nm to about 170 nm in mean diameter, about 1 nm to about 160 nm in mean diameter, about 1 nm to about 150 nm in mean diameter, about 1 nm to about 140 nm in mean diameter, about 1 nm to about 130 nm in mean diameter, about 1 nm to about 120 nm in mean diameter, about 1 nm to about 110 nm in mean diameter, about 1 nm to about 100 nm in mean diameter, about 1 nm to about 90 nm in mean diameter, about 1 nm to about 80 nm in mean diameter, about 1 nm to about 70 nm in mean diameter, about 1 nm to about 60 nm in mean diameter, about 1 nm to about 50 nm in mean diameter, about 1 nm to about 40 nm in mean diameter, about 1 nm to about 30 nm in mean diameter, or about 1 nm to about 20 nm in mean diameter, about 1 nm to about 10 nm in mean diameter. In other aspects, the size of the nanoparticles is from about 5 nm to about 150 nm (mean diameter), from about 5 to about 50 nm, from about 10 to about 30 nm, from about 10 to 150 nm, from about 10 to about 100 nm, or about 10 to about 50 nm. The size of the nanoparticles is from about 5 nm to about 150 nm (mean diameter), from about 30 to about 100 nm, from about 40 to about 80 nm. The size of the nanoparticles used in a method varies as required by their particular use or application. The variation of size is advantageously used to optimize certain physical characteristics of the nanoparticles, for example, optical properties or the amount of surface area that can be functionalized as described herein.

Nanoparticles of larger diameter are, in some aspects, contemplated to be functionalized with a greater number of biomolecules [Hurst et al., Analytical Chemistry 78(24): 8313-8318 (2006)] during nanoconjugate production. In some aspects, therefore, the number of biomolecules used in the production of a nanoconjugate is from about 10 to about 25,000 biomolecules per nanoconjugate. In further aspects, the number of, biomolecules used in the production of a nanoconjugate is from about 50 to about 10,000 biomolecules per nanoconjugate, or from about 200 to about 5,000 biomolecules per nanoconjugate, or from about 50 to about 100 biomolecules per nanoconjugate, or from about 20 to about 100, biomolecules per nanoconjugate, or from about 20 to about 50 biomolecules per nanoconjugate. Thus, in various embodiments, the number of biomolecules used in the production of a nanoconjugate is about 10, about 15, about 20, about 25, about 30, about 35, about 40, about 45, about 50, about 55, about 60, about 65, about 70, about 75, about 80, about 85, about 90, about 95, about 100, about 150, about 200, about 250, about 300, about 350, about 400, about 500, about 600, about 700, about 800, about 900, about 1,000, about 2,000, about 5000, about 10,000, about 15,000, about 20,000, about 25,000 or more per nanoconjugate.

Hollow Nanoconjugates

As described herein, in various aspects the nanoconjugates provided by the disclosure are hollow. The porosity and/or rigidity of a hollow nanoconjugate depends in part on the density of biomolecules that are crosslinked on the surface of a nanoparticle during nanoconjugate production. In general, a lower density of biomolecules crosslinked on the surface of the nanoparticle results in a more porous nanoconjugate, while a higher density of biomolecules crosslinked on the surface of the nanoparticle results in a more rigid nanoconjugate. Porosity and density of a hollow nanoconjugate also depends on the degree and type of crosslinking between biomolecules.

Methods of making hollow nanoconjugates are known in the art, and are generally described in International Patent Application Number PCT/US2010/055018 and Zhang et al. [J Am Chem Soc. 132(43): 15151-15153 (2010)], which are each incorporated by reference herein in their entirety.

In some embodiments, hollow nanoconjugates are prepared via poly alkyne chemistry [Zhang et al., J Am Chem. Soc. 132(43): 15151-15153 (2010)]. Additional cross linking strategies, such as through the use of a homobifunctional cross linker (e.g., Sulfo-EGS) or other reactive group (for example and without limitation, amines, amides, alcohols, esters, aldehydes, ketones, thiols, disulfides, carboxylic acids, phenols, imidazoles, hydrazines, hydrazones, azides, and alkynes) are also contemplated.

An additional method of preparing a hollow nanoconjugate, called surface assisted crosslinking (SAC), comprises a mixed monolayer of modified nucleic acids and reactive thiolated molecules that are assembled on the nanoparticle surface and crosslinked together. As used herein, a "monolayer" means that only a single stratum of biomolecules is crosslinked at the surface of a nanoconjugate. A biomolecule as used herein includes without limitation a polynucleotide, peptide, polypeptide, small molecule, therapeutic agent, contrast agent and a combination thereof.

The chemical that causes crosslinking of the biomolecules of interest are known to those of skill in the art, and include without limitation Disuccinimidyl glutarate, Disuccinimidyl suberate, Bis[sulfosuccinimidyl] suberate, Tris-succinimidyl aminotriacetate, succinimidyl 4-hydrazinonicotinate acetone hydrazone, succinimidyl 4-hydrazidoterephthalate hydrochloride, succinimidyl 4-formylbenzoate, Dithiobis [succinimidyl propionate], 3,3'-Dithiobis[sulfosuccinimidylpropionate], Disuccinimidyl tartarate, Bis[2-(succinimidooxycarbonyloxy)ethyl]sulfone, Ethylene glycol bis [succinimidylsuccinate], Ethylene glycol bis [sulfosuccinimidylsuccinate], Dimethyl adipimidate.2 HCl, Dimethyl pimelimidate.2 HCl, Dimethyl Suberimidate.2 HCl, 1,5-Difluoro-2,4-dinitrobenzene, β-[Tris(hydroxymethyl) phosphino] propionic acid, Bis-maleimidoethane, 1,4-bismaleimidobutane, Bismaleimidohexane, Tris[2-maleimidoethyl]mine, 1,8-Bis-maleimido-diethyleneglycol, 1,11-Bis-maleimido-triethyleneglycol, 1,4 bismaleimidyl-2,3-dihydroxybutane, Dithio-bismaleimidoethane, 1,4-Di-[3'-(2'-pyridyldithio]-propionamido/butane, 1,6-Hexane-bis-vinylsulfone, Bis-[b-(4-Azidosalicylamido)ethyl]disulfide, N-(a-Maleimidoacetoxy) succinimide ester, N-[β-Maleimidopropyloxy]succinimide ester, N-[g-Maleimidobutyryloxy]succinimide ester, N-[g-Maleimidobutyryloxy]sulfosuccinimide ester, m-Maleimidobenzoyl-N-hydroxysuccinimide ester, m-Maleimidobenzoyl-N-hydroxysulfosuccinimide ester, Succinimidyl 4-[N-maleimidomethyl]cyclohexane-1-carboxylate, Sulfosuccinimidyl 4-[N-maleimidomethyl]cyclohexane-1-carboxylate, N-e-Maleimidocaproyloxy]succinimide ester, N-e-Maleimidocaproyloxy]sulfosuccinimide ester, Succinimidyl 4-[p-maleimidophenyl]butyrate, Sulfosuccinimidyl 4-[p-maleimidophenyl]butyrate, Succinimidyl-6-[β-maleimidopropionamido]hexanoate, Succinimidyl-4-[N-Maleimidomethyl]cyclohexane-1-carboxy-[6-amidocaproate], N-[k-Maleimidoundecanoyloxy]sulfosuccinimide ester, N-Succinimidyl 3-(2-pyridyldithio)-propionate, Succinimidyl 6-(3-[2-pyridyldithio]-propionamido)hexanoate, 4-Succinimidyloxycarbonyl-methyl-a-[2-pyridyldithio]toluene, 4-Sulfosuccinimidyl-6-methyl-a-(2-pyridyldithio)toluamido]hexanoate), N-Succinimidyl iodoacetate, Succinimidyl 3-[bromoacetamido]propionate, N-Succinimidyl[4-iodoacetyl]aminobenzoate, N-Sulfosuccinimidyl[4-iodoacetyl]aminobenzoate, N-Hydroxysuccinimidyl-4-azidosalicylic acid, N-5-Azido-2-nitrobenzoyloxysuccinimide, N-Hydroxysulfosuccinimidyl-4-azidobenzoate, Sulfosuccinimidyl[4-azidosalicylamido]hexanoate, N-Succinimidyl-6-(4'-azido-2'-nitrophenylamino) hexanoate, N-Sulfosuccinimidyl-6-(4'-azido-2'-nitrophenylamino) hexanoate, Sulfosuccinimidyl-(perfluoroazidobenzamido)-ethyl-1,3'-dithioproprionate, Sulfosuccinimidyl-2-(m-azido-o-nitrobenzamido)-ethyl-1, 3'-proprionate, Sulfosuccinimidyl 2-[7-amino-4-methylcoumarin-3-acetamido]ethyl-1,3' dithiopropionate, Succinimidyl 4,4'-azipentanoate, Succinimidyl 6-(4,4'-azipentanamido)hexanoate, Succinimidyl 2-([4,4'-azipentanamido]ethyl)-1,3'-dithioproprionate, Sulfosuccinimidyl 4,4'-azipentanoate, Sulfosuccinimidyl 6-(4,4'-azipentanamido)hexanoate, Sulfosuccinimidyl 2-([4, 4'-azipentanamido]ethyl)-1,3'-dithioproprionate, Dicyclohexylcarbodiimide, 1-Ethyl-3-[3-dimethylaminopropyl]carbodiimide Hydrochloride, N-[4-(p-Azidosalicylamido) butyl]-3''-(2'-pyridyldithio)propionamide, N-[β-Maleimidopropionic acid] hydrazide, trifluoroacetic acid salt, [N-e-Maleimidocaproic acid] hydrazide, trifluoroacetic acid salt, 4-(4-N-Maleimidophenyl)butyric acid hydrazide hydrochloride, N-[k-Maleimidoundecanoic acid]hydrazide, 3-(2-Pyridyldithio)propionyl hydrazide, p-Azidobenzoyl hydrazide, N-[p-Maleimidophenyl] isocyanate, and Succinimidyl-[4-(psoralen-8-yloxy)]-butyrate.

Biomolecules

As described herein, a biomolecule includes without limitation a polynucleotide, peptide, polypeptide, small molecule, therapeutic agent, contrast agent and a combination thereof. In various aspects of the disclosure a biomolecule as described herein is covalently associated with the nanoparticle.

Polynucleotides

Polynucleotides contemplated by the present disclosure include DNA, RNA, modified forms and combinations thereof as defined herein. Accordingly, in some aspects, the nanoconjugate comprises DNA. In some embodiments, the DNA is double stranded, and in further embodiments the DNA is single stranded. In further aspects, the nanoconjugate comprises RNA, and in still further aspects the nanoconjugate comprises double stranded RNA, and in a specific embodiment, the double stranded RNA agent is a small interfering RNA (siRNA). The term "RNA" includes duplexes of two separate strands, as well as single stranded structures. Single stranded RNA also includes RNA with secondary structure. In one aspect, RNA having a hairpin loop is contemplated.

When a nanoconjugate comprise a plurality of structural polynucleotides, the polynucleotide is, in some aspects, comprised of a sequence that is sufficiently complementary to a target sequence of a polynucleotide such that hybridization of the polynucleotide that is part of the nanoconjugate and the target polynucleotide takes place. The polynucleotide in various aspects is single stranded or double stranded, as long as the double stranded molecule also includes a single strand sequence that hybridizes to a single strand sequence of the target polynucleotide. In some aspects, hybridization of the polynucleotide that is part of the nanoconjugate can form a triplex structure with a double-stranded target polynucleotide. In another aspect, a triplex structure can be formed by hybridization of a double-stranded polynucleotide that is part of a nanoconjugate to a single-stranded target polynucleotide. Further description of triplex polynucleotide complexes is found in PCT/US2006/40124, which is incorporated herein by reference in its entirety.

In some aspects, polynucleotides contain a spacer as described herein. The spacer, in one aspect, comprises one or more crosslinking moieties that facilitate the crosslinking of one polynucleotide to another polynucleotide.

A "polynucleotide" is understood in the art to comprise individually polymerized nucleotide subunits. The term "nucleotide" or its plural as used herein is interchangeable with modified forms as discussed herein and otherwise known in the art. In certain instances, the art uses the term "nucleobase" which embraces naturally-occurring nucleotide, and non-naturally-occurring nucleotides which include modified nucleotides. Thus, nucleotide or nucleobase means the naturally occurring nucleobases adenine (A), guanine (G), cytosine (C), thymine (T) and uracil (U). Non-naturally occurring nucleobases include, for example and without limitations, xanthine, diaminopurine, 8-oxo-N-6-methyladenine, 7-deazaxanthine, 7-deazaguanine, N4,N4-ethanocytosin, N',N'-ethano-2,6-diaminopurine, 5-methylcytosine (mC), 5-(C3-C6)-alkynyl-cytosine, 5-fluorouracil, 5-bromouracil, pseudoisocytosine, 2-hydroxy-5-methyl-4-tr-iazolopyridin, isocytosine, isoguanine, inosine and the "non-naturally occurring" nucleobases described in Benner et al., U.S. Pat. No. 5,432,272 and Susan M. Freier and Karl-Heinz Altmann, 1997, Nucleic Acids Research, vol. 25: pp 4429-4443. The term "nucleobase" also includes not only the known purine and pyrimidine heterocycles, but also heterocyclic analogues and tautomers thereof. Further naturally and non-naturally occurring nucleobases include those disclosed in U.S. Pat. No. 3,687,808 (Merigan, et al.); in Chapter 15 by Sanghvi, in Antisense Research and Application, Ed. S. T. Crooke and B. Lebleu, CRC Press, 1993, in Englisch et al., 1991, Angewandte Chemie, International Edition, 30: 613-722 (see especially pages 622 and 623, and in the Concise Encyclopedia of Polymer Science and Engineering, J. I. Kroschwitz Ed., John Wiley & Sons, 1990, pages 858-859, Cook, Anti-Cancer Drug Design 1991, 6, 585-607, each of which are hereby incorporated by reference in their entirety). In various aspects, polynucleotides also include one or more "nucleosidic bases" or "base units" which are a category of non-naturally-occurring nucleotides that include compounds such as heterocyclic compounds that can serve like nucleobases, including certain "universal bases" that are not nucleosidic bases in the most classical sense but serve as nucleosidic bases. Universal bases include 3-nitropyrrole, optionally substituted indoles (e.g., 5-nitroindole), and optionally substituted hypoxanthine. Other desirable universal bases include, pyrrole, diazole or triazole derivatives, including those universal bases known in the art.

Modified nucleotides are described in EP 1 072 679 and WO 97/12896, the disclosures of which are incorporated herein by reference. Modified nucleotides include without limitation, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil, and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified bases include tricyclic pyrimidines such as phenoxazine cytidine(1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzox-azin-2 (3H)-one), carbazole cytidine (2H-pyrimido[4,5-b]indol-2-one), pyridoindole cytidine (H-pyrido[3',2': 4,5]pyrrolo[2,3-d]pyrimidin-2-one). Modified bases may also include those in which the purine or pyrimidine base is replaced with other heterocycles, for example 7-deazaadenine, 7-deazaguanosine, 2-aminopyridine and 2-pyridone. Additional nucleobases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., 1991, Angewandte Chemie, International Edition, 30: 613, and those disclosed by Sanghvi, Y. S., Chapter 15, Antisense Research and Applications, pages 289-302, Crooke, S. T. and Lebleu, B., ed., CRC Press, 1993. Certain of these bases are useful for increasing the binding affinity and include 5-substituted pyrimidines, 6-azapyrimidines and N2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. and are, in certain aspects combined with 2'-O-methoxyethyl sugar modifications. See, U.S. Pat. Nos. 3,687,808, 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,645,985; 5,830,653; 5,763,588; 6,005,096; 5,750,692 and 5,681,941, the disclosures of which are incorporated herein by reference.

Methods of making polynucleotides of a predetermined sequence are well-known. See, e.g., Sambrook et al., Molecular Cloning: A Laboratory Manual (2nd ed. 1989) and F. Eckstein (ed.) Oligonucleotides and Analogues, 1st Ed. (Oxford University Press, New York, 1991). Solid-phase synthesis methods are preferred for both polyribonucleotides and polydeoxyribonucleotides (the well-known methods of synthesizing DNA are also useful for synthesizing RNA). Polyribonucleotides can also be prepared enzymatically. Non-naturally occurring nucleobases can be incorporated into the polynucleotide, as well. See, e.g., U.S. Pat. No. 7,223,833; Katz, J. Am. Chem. Soc., 74:2238 (1951); Yamane, et al., J. Am. Chem. Soc., 83:2599 (1961); Kosturko, et al., Biochemistry, 13:3949 (1974); Thomas, J. Am. Chem. Soc., 76:6032 (1954); Zhang, et al., J. Am. Chem. Soc., 127:74-75 (2005); and Zimmermann, et al., J. Am. Chem. Soc., 124:13684-13685 (2002).

A nanoconjugate of the disclosure generally comprises a polynucleotide from about 5 nucleotides to about 100 nucleotides in length. More specifically, nanoconjugates comprise polynucleotides that are about 5 to about 90 nucleotides in length, about 5 to about 80 nucleotides in length, about 5 to about 70 nucleotides in length, about 5 to about 60 nucleotides in length, about 5 to about 50 nucleotides in length about 5 to about 45 nucleotides in length, about 5 to about 40 nucleotides in length, about 5 to about 35 nucleotides in length, about 5 to about 30 nucleotides in length, about 5 to about 25 nucleotides in length, about 5 to about 20 nucleotides in length, about 5 to about 15 nucleotides in length, about 5 to about 10 nucleotides in length, and all polynucleotides intermediate in length of the sizes specifically disclosed to the extent that the polynucleotide is able to achieve the desired result. Accordingly, polynucleotides of 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more nucleotides in length are contemplated.

In some aspects, a polynucleotide as described herein comprises an alkyne. In various embodiments, from 1 to 100 alkyne moieties are present on a polynucleotide. In further aspects, from about 5 to about 50 alkyne moieties, or about 10 to about 20 alkyne moieties are present on a polynucleotide. In one aspect, 10 alkyne moieties are present on the polynucleotide. In further aspects, 1, 2, 3, 4, 5, 6, 7, 8, 9, 10, 11, 12, 13, 14, 15, 16, 17, 18, 19, 20, 21, 22, 23, 24, 25, 26, 27, 28; 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68; 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more alkyne moieties are present on a polynucleotide.

In another embodiment, the alkyne moieties on a polynucleotide are on the 5' end. In a further embodiment, the alkyne moieties on a polynucleotide are on the 3' end. It is contemplated that in some aspects the alkyne moieties represent only a portion of the length of a polynucleotide. By way of example, if a polynucleotide is 20 nucleotides in length, then it is contemplated that the first 10 nucleotides (counting, in various aspects from either the 5' or 3' end) comprise an alkyne moiety. Thus, 10 nucleotides comprising an alkyne moiety out of a total of 20 nucleotides results in 50% of the nucleotides in a polynucleotide being associated with an alkyne moiety. In various aspects it is contemplated that from about 0.01% to about 100% of the nucleotides in a polynucleotide are associated with an alkyne moiety. In further aspects, about 1% to about 70%, or about 2% to about 60%, or about 5% to about 50%, or about 10% to about 50%, or about 10% to about 40%, or about 20% to about 50%, or about 20% to about 40% of nucleotides in a polynucleotide are associated with an alkyne moiety.

Polynucleotides, as defined herein, also includes aptamers. The production and use of aptamers is known to those of ordinary skill in the art. In general, aptamers are nucleic acid or peptide binding species capable of tightly binding to and discreetly distinguishing target ligands [Yan et al., RNA Biol. 6(3) 316-320 (2009), incorporated by reference herein in its entirety]. Aptamers, in some embodiments, may be obtained by a technique called the systematic evolution of ligands by exponential enrichment (SELEX) process [Tuerk et al., Science 249:505-10 (1990), U.S. Pat. No. 5,270,163, and U.S. Pat. No. 5,637,459, each of which is incorporated herein by reference in their entirety]. General discussions of nucleic acid aptamers are found in, for example and without limitation, Nucleic Acid and Peptide Aptamers: Methods and Protocols (Edited by Mayer, Humana Press, 2009) and Crawford et al., Briefings in Functional Genomics and Proteomics 2(1): 72-79 (2003). Additional discussion of aptamers, including but not limited to selection of RNA aptamers, selection of DNA aptamers, selection of aptamers capable of covalently linking to a target protein, use of modified aptamer libraries, and the use of aptamers as a diagnostic agent and a therapeutic agent is provided in Kopylov et al., Molecular Biology 34(6): 940-954 (2000) translated from Molekulyamaya Biologiya, Vol. 34, No. 6, 2000, pp. 1097-1113, which is incorporated herein by reference in its entirety. In various embodiments, an aptamer is between about 10 to about 100 nucleotides in length.

Spacers

In certain aspects, nanoconjugates are contemplated which include those wherein a nanoconjugate comprises a polynucleotide which further comprises a spacer. The spacer, in various aspects, comprises one or more crosslinking moieties as described below.

"Spacer" as used herein means a moiety that serves to contain one or more crosslinking moieties, or, in some aspects wherein the nanoconjugate comprises a nanoparticle, increase distance between the nanoparticle and the polynucleotide, or to increase distance between individual polynucleotides when attached to the nanoparticle in multiple copies. In aspects of the disclosure wherein a nanoconjugate is used for a biological activity, it is contemplated that the spacer does not directly participate in the activity of the polynucleotide to which it is attached.

Thus, in some aspects, the spacer is contemplated herein to facilitate crosslinking via one or more crosslinking moieties. Spacers are additionally contemplated, in various aspects, as being located between individual polynucleotides in tandem, whether the polynucleotides have the same sequence or have different sequences. In one aspect, the spacer when present is an organic moiety. In another aspect, the spacer is a polymer, including but not limited to a water-soluble polymer, a nucleic acid, a polypeptide, an oligosaccharide, a carbohydrate, a lipid, or combinations thereof.

In some embodiments, the spacer is functionalized to a nanoparticle but is not linked to another biomolecule. The function of the spacer in these embodiments is to protect the nanoconjugate in vivo. Thus, in some embodiments, a spacer is functionalized to a nanoparticle. In further embodiments, the spacer is polyethylene glycol (PEG). In embodiments wherein the water soluble polymer is PEG, it is contemplated that the PEG is functionalized to a nanoparticle via a covalent bond. In some embodiments, the PEG is attached to the nanoparticle via a thiol bond. PEGylation is contemplated to protect the nanoconjugate in circulation and improve its pharmacodynamic and pharmacokinetic profiles [Harris et al., Nat Rev Drug Discov. 2: 214-21 (2003)]. The PEGylation process attaches repeating units of ethylene glycol (polyethylene glycol (PEG)) to a nanoparticle. PEG molecules have a large hydrodynamic volume (5-10 times the size of globular proteins), are highly water soluble and hydrated, non-toxic, non-immunogenic and rapidly cleared from the body. PEGylation of nanoconjugates leads, in various embodiments, to increased resistance to enzymatic degradation, increased half-life in vivo, reduced dosing frequency, decreased immunogenicity, increased physical and thermal stability, increased solubility, increased liquid stability, and reduced aggregation.

The length of the spacer in various embodiments at least about 5 nucleotides, at least about 10 nucleotides, 10-30 nucleotides, or even greater than 30 nucleotides. The spacer may have any sequence which does not interfere with the ability of the polynucleotides to become bound to the nanoparticles or to the target polynucleotide. The spacers should not have sequences complementary to each other or to that of the polynucleotides, but may be all or in part complementary to the target polynucleotide. In certain aspects, the bases of the polynucleotide spacer are all adenines, all thymines, all cytidines, all guanines, all uracils, or all some other modified base.

Modified Polynucleotides

As discussed above, modified polynucleotides are contemplated for use in producing nanoconjugates. In various aspects, a polynucleotide is completely modified or partially modified. Thus, in various aspects, one or more, or all, sugar and/or one or more or all internucleotide linkages of the nucleotide units in the polynucleotide are replaced with "non-naturally occurring" groups.

In one aspect, this embodiment contemplates a peptide nucleic acid (PNA). In PNA compounds, the sugar-backbone of a polynucleotide is replaced with an amide containing backbone. See, for example U.S. Pat. Nos. 5,539,082; 5,714,331; and 5,719,262, and Nielsen et al., Science, 1991, 254, 1497-1500, the disclosures of which are herein incorporated by reference.

Other linkages between nucleotides and unnatural nucleotides contemplated for the disclosed polynucleotides include those described in U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920; U.S. Patent Publication No. 20040219565; International Patent Publication Nos. WO 98/39352 and WO 99/14226; Mesmaeker et. al., Current Opinion in Structural Biology 5:343-355 (1995) and Susan M. Freier and Karl-Heinz Altmann, Nucleic Acids Research, 25:4429-4443 (1997), the disclosures of which are incorporated herein by reference.

Specific examples of polynucleotides include those containing modified backbones or non-natural internucleoside linkages. Polynucleotides having modified backbones include those that retain a phosphorus atom in the backbone and those that do not have a phosphorus atom in the backbone. Modified polynucleotides that do not have a phosphorus atom in their internucleoside backbone are considered to be within the meaning of "polynucleotide."

Modified polynucleotide backbones containing a phosphorus atom include, for example, phosphorothioates, chiral phosphorothioates, phosphorodithioates, phosphotriesters, aminoalkylphosphotriesters, methyl and other alkyl phosphonates including 3'-alkylene, phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Also contemplated are polynucleotides having inverted polarity comprising a single 3' to 3' linkage at the 3'-most internucleotide linkage, i.e. a single inverted nucleoside residue which may be abasic (the nucleotide is missing or has a hydroxyl group in place thereof). Salts, mixed salts and free acid forms are also contemplated.

Representative United States patents that teach the preparation of the above phosphorus-containing linkages include, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, the disclosures of which are incorporated by reference herein.

Modified polynucleotide backbones that do not include a phosphorus atom have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages; siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. In still other embodiments, polynucleotides are provided with phosphorothioate backbones and oligonucleosides with heteroatom backbones, and including —CH2-NH—O—CH2-, —CH2-N(CH3)-O—CH2-, —CH2-O—N(CH3)-CH2-, —CH2-N(CH3)-N(CH3)—CH2- and —O—N(CH3)-CH2-CH2- described in U.S. Pat. Nos. 5,489,677, and 5,602,240. See, for example, U.S. Pat. Nos. 5,034,506; 5,166,315; 5,185,444; 5,214,134; 5,216, 141; 5,235,033; 5,264,562; 5,264,564; 5,405,938; 5,434, 257; 5,466,677; 5,470,967; 5,489,677; 5,541,307; 5,561, 225; 5,596,086; 5,602,240; 5,610,289; 5,602,240; 5,608, 046; 5,610,289; 5,618,704; 5,623,070; 5,663,312; 5,633, 360; 5,677,437; 5,792,608; 5,646,269 and 5,677,439, the disclosures of which are incorporated herein by reference in their entireties.

In various forms, the linkage between two successive monomers in the polynucleotide consists of 2 to 4, desirably 3, groups/atoms selected from —CH2-, —O—, —S—, —NRH—, >C=O, >C=NRH, >C=S, —Si(R")2-, —SO—, —S(O)2-, —P(O)2-, —PO(BH3)-, —P(O,S)—, —P(S)2-, —PO(R")—, —PO(OCH3) —, and —PO (NHRH)—, where RH is selected from hydrogen and C1-4-alkyl, and R" is selected from C1-6-alkyl and phenyl. Illustrative examples of such linkages are —CH2-CH2-CH2-, —CH2-CO—CH2-, —CH2-CHOH—CH2-, —O—CH2-O—, —O—CH2-CH2-, —O—CH2-CH=(including R5 when used as a linkage to a succeeding monomer), —CH2-CH2-O—, —NRH—CH2-CH2-, —CH2-CH2-NRH—, —CH2-NRH—CH2-, —O—CH2-CH2-

NRH—, —NRH—CO—O—, —NRH—CO—NRH—, —NRH—CS—NRH—, —NRH—C(=NRH)—NRH—, —NRH—CO—CH2-NRH—O—CO—O—, —O—CO—CH2-O—, —O—CH2-CO—O—, —CH2-CO—NRH—, —O—CO—NRH—, —NRH—CO—CH2-O—CH2-CO—NRH—, —O—CH2-CH2-NRH—, —CH=N—O—, —CH2-NRH—O—, —CH2-O—N=(including R5 when used as a linkage to a succeeding monomer), —CH2-O—NRH—, —CO—NRH—CH2-, —CH2-NRH—O—, —CH2-NRH—CO—, —O—NRH—CH2-, —O—NRH, —O—CH2-S—, —S—CH2-O—, —CH2-CH2-S—, —O—CH2-CH2-S—, —S—CH2-CH=(including R5 when used as a linkage to a succeeding monomer), —S—CH2-CH2-, —S—CH2-CH2-O—, —S—CH2-CH2-S—, —CH2-S—CH2-, —CH2-SO—CH2-, —CH2-SO2-CH2-, —O—SO—O—, —O—S(O)2-O—, —O—S(O)2-CH2-, —O—S(O)2-NRH—, —NRH—S(O)2-CH2-; —O—S(O)2-CH2-, —O—P(O)2-O—, —O—P(O,S)—O—, —O—P(S)2-O—, —S—P(O)2-O—, —S—P(O,S)—O—, —S—P(S)2-O—, —O—P(O)2-S—, —O—P(O,S)—S—, —O—P(S)2-S—, —S—P(O)2-S—, —S—P(O,S)—S—, —S—P(S)2-S—, —O—PO(R")—O—, —O—PO(OCH3)-O—, —O—PO(OCH2CH3)-O—, —O—PO(OCH2CH2S—R)—O—, —O—PO(BH3)-O—, —O—PO(NHRN)—O—, —O—P(O)2-NRH H—, —NRH—P(O)2-O—, —O—P(O,NRH)—O—, —CH2-P(O)2-O—, —O—P(O)2-CH2-, and —O—Si(R")2-O—; among which —CH2-CO—NRH—, CH2-NRH—O —, —S—CH2-O—, —O—P(O)2-O-β-P(—O,S)—O—, —O—P(S)2-O—, —NRH P(O)2-O—, —O—P(O,NRH)—O—, —O—PO(R")—O—, —O—PO(CH3)-O—, and —O—PO(NHRN)—O—, where RH is selected form hydrogen and C1-4-alkyl, and R" is selected from C1-6-alkyl and phenyl, are contemplated. Further illustrative examples are given in Mesmaeker et. al., 1995, Current Opinion in Structural Biology, 5: 343-355 and Susan M. Freier and Karl-Heinz Altmann, 1997, Nucleic Acids Research, vol 25: pp 4429-4443.

Still other modified forms of polynucleotides are described in detail in U.S. Patent Application No. 20040219565, the disclosure of which is incorporated by reference herein in its entirety.

Modified polynucleotides may also contain one or more substituted sugar moieties. In certain aspects, polynucleotides comprise one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted C1 to C10 alkyl or C2 to C10 alkenyl and alkynyl. Other embodiments include O[(CH2)nO]mCH3, O(CH2)nOCH3, O(CH2)nNH2, O(CH2)nCH3, O(CH2)nONH2, and O(CH2)nON[(CH2)nCH3]2, where n and m are from 1 to about 10. Other polynucleotides comprise one of the following at the 2' position: C1 to C10 lower alkyl, substituted lower alkyl, alkenyl, alkynyl, alkaryl, aralkyl, O-alkaryl or O-aralkyl, SH, SCH3, OCN, Cl, Br, CN, CF3, OCF3, SOCH3, SO2CH3, ONO2, NO2, N3, NH2, heterocycloalkyl, heterocycloalkaryl, aminoalkylamino, polyalkylamino, substituted silyl, an RNA cleaving group, a reporter group, an intercalator, a group for improving the pharmacokinetic properties of a polynucleotide, or a group for improving the pharmacodynamic properties of a polynucleotide, and other substituents having similar properties. In one aspect, a modification includes 2'-methoxyethoxy (2'-O—CH2CH2OCH3, also known as 2'-O-(2-methoxyethyl) or 2'-MOE) (Martin et al., 1995, Helv. Chim. Acta, 78: 486-504) i.e., an alkoxyalkoxy group. Other modifications include 2'-dimethylaminooxyethoxy, i.e., a O(CH2)2ON(CH3)2 group, also known as 2'-DMAOE, and 2'-dimethylaminoethoxyethoxy (also known in the art as 2'-O-dimethyl-amino-ethoxy-ethyl or 2'-DMAEOE), i.e., 2'-O—CH2-O—CH2-N(CH3)2.

Still other modifications include 2'-methoxy (2'-O—CH3), 2'-aminopropoxy (2'-OCH2CH2CH2NH2), 2'-allyl (2'-CH2-CH=CH2), 2'-O-allyl (2'-O—CH2-CH=CH2) and 2'-fluoro (2'-F). The 2'-modification may be in the arabino (up) position or ribo (down) position. In one aspect, a 2'-arabino modification is 2'-F. Similar modifications may also be made at other positions on the polynucleotide, for example, at the 3' position of the sugar on the 3' terminal nucleotide or in 2'-5' linked polynucleotides and the 5' position of 5' terminal nucleotide. Polynucleotides may also have sugar mimetics such as cyclobutyl moieties in place of the pentofuranosyl sugar. See, for example, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, the disclosures of which are incorporated by reference in their entireties herein.

In one aspect, a modification of the sugar includes Locked Nucleic Acids (LNAs) in which the 2'-hydroxyl group is linked to the 3' or 4' carbon atom of the sugar ring, thereby forming a bicyclic sugar moiety. The linkage is in certain aspects a methylene (—CH2-)$_n$ group bridging the 2' oxygen atom and the 4' carbon atom wherein n is 1 or 2. LNAs and preparation thereof are described in WO 98/39352 and WO 99/14226, the disclosures of which are incorporated herein by reference.

Polynucleotide Features

A nanoconjugate of the disclosure, in various aspects, comprises a plurality of polynucleotides. As a result, each nanoconjugate has the ability to bind to a plurality of target polynucleotides having a sufficiently complementary sequence. For example, if a specific polynucleotide is targeted, a single nanoconjugate has the ability to bind to multiple copies of the same molecule. In one aspect, methods are provided wherein the nanoconjugate comprises identical polynucleotides, i.e., each polynucleotide has the same length and the same sequence. In other aspects, the nanoconjugate comprises two or more polynucleotides which are not identical, i.e., at least one of the polynucleotides of the nanoconjugate differ from at least one other polynucleotide of the nanoconjugate in that it has a different length and/or a different sequence. In aspects wherein a nanoconjugate comprises different polynucleotides, these different polynucleotides bind to the same single target polynucleotide but at different locations, or bind to different target polynucleotides which encode different gene products. Accordingly, in various aspects, a single nanoconjugate may be used in a method to inhibit expression of more than one gene product. Polynucleotides are thus used to target specific polynucleotides, whether at one or more specific regions in the target polynucleotide, or over the entire length of the target polynucleotide as the need may be to effect a desired level of inhibition of gene expression.

Accordingly, in one aspect, the polynucleotides are designed with knowledge of the target sequence. Alternatively, a polynucleotide in a nanoconjugate need not hybridize to a target polynucleotide in order to achieve a desired effect as described herein.

Polynucleotides contemplated for production of a nanoconjugate include, in one aspect, those which modulate expression of a gene product expressed from a target polynucleotide. Accordingly, antisense polynucleotides which hybridize to a target polynucleotide and inhibit translation, siRNA polynucleotides which hybridize to a target polynucleotide and initiate an RNAse activity (for example RNAse H), triple helix forming polynucleotides which hybridize to double-stranded polynucleotides and inhibit transcription, and ribozymes which hybridize to a target polynucleotide and inhibit translation, are contemplated.

In some aspects, a polynucleotide-based nanoconjugate allows for efficient uptake of the nanoconjugate. In various aspects, the polynucleotide comprises a nucleotide sequence that allows increased uptake efficiency of the nanoconjugate. As used herein, "efficiency" refers to the number or rate of uptake of nanoconjugates in/by a cell. Because the process of nanoconjugates entering and exiting a cell is a dynamic one, efficiency can be increased by taking up more nanoconjugates or by retaining those nanoconjugates that enter the cell for a longer period of time. Similarly, efficiency can be decreased by taking up fewer nanoconjugates or by retaining those nanoconjugates that enter the cell for a shorter period of time.

Thus, the nucleotide sequence can be any nucleotide sequence that is desired may be selected for, in various aspects, increasing or decreasing cellular uptake of a nanoconjugate or gene regulation. The nucleotide sequence, in some aspects, comprises a homopolymeric sequence which affects the efficiency with which the nanoparticle to which the polynucleotide is attached is taken up by a cell. Accordingly, the homopolymeric sequence increases or decreases the efficiency. It is also contemplated that, in various aspects, the nucleotide sequence is a combination of nucleobases, such that it is not strictly a homopolymeric sequence. For example and without limitation, in various aspects, the nucleotide sequence comprises alternating thymidine and uridine residues, two thymidines followed by two uridines or any combination that affects increased uptake is contemplated by the disclosure. In some aspects, the nucleotide sequence affecting uptake efficiency is included as a domain in a polynucleotide comprising additional sequence. This "domain" would serve to function as the feature affecting uptake efficiency, while the additional nucleotide sequence would serve to function, for example and without limitation, to regulate gene expression. In various aspects, the domain in the polynucleotide can be in either a proximal, distal, or center location relative to the nanoconjugate. It is also contemplated that a polynucleotide comprises more than one domain.

The homopolymeric sequence, in some embodiments, increases the efficiency of uptake of the nanoconjugate by a cell. In some aspects, the homopolymeric sequence comprises a sequence of thymidine residues (polyT) or uridine residues (polyU). In further aspects, the polyT or polyU sequence comprises two thymidines or uridines. In various aspects, the polyT or polyU sequence comprises from about 3 to about 500 thymidine or uridine residues. In further embodiments, the polyT or polyU sequence comprises from about 3 to about 10, about 20, about 30, about 40, about 50, about 60, about 70, about 80, about 90, about 100, about 150, about 200 or more thymidine or uridine residues. In some embodiments, the polyT or polyU sequences comprises from about 10 to about 50, about 20 to about 100, or about 40 to about 200 thymidine or uridine residues. Accordingly, in various embodiments, the polyT or polyU sequence comprises 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, about 55, about 60, about 65, about 70, about 75, about 80, about 85, about 90, about 95, about 100, about 125, about 150, about 0.175, about 200, about 250, about 300, about 350, about 400, about 450, about 500 or more thymidine or uridine residues.

In some embodiments, it is contemplated that a nanoconjugate comprising a polynucleotide that comprises a homopolymeric sequence is taken up by a cell with greater efficiency than a nanoconjugate comprising the same polynucleotide but lacking the homopolymeric sequence. In various aspects, a nanoconjugate comprising a polynucleotide that comprises a homopolymeric sequence is taken up by a cell about 2-fold, about 3-fold, about 4-fold, about 5-fold, about 6-fold, about 7-fold, about 8-fold, about 9-fold, about 10-fold, about 20-fold, about 30-fold, about 40-fold, about 50-fold, about 100-fold or higher, more efficiently than a nanoconjugate comprising the same polynucleotide but lacking the homopolymeric sequence.

In other aspects, the domain is a phosphate polymer (C3 residue). In some aspects, the domain comprises a phosphate polymer (C3 residue) that is comprised of two phosphates. In some embodiments, the C3 residue comprises from about 3 to about 500, or from about 5 to about 50 phosphates, or from about 10 to about 50 phosphates, or from about 20 to about 70 phosphates, or from about 50 to about 200 phosphates. In various aspects, the C3 residue comprises 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, about 55, about 60, about 65, about 70, about 75, about 80, about 85, about 90, about 95, about 100, about 125, about 150, about 175, about 200, about 250, about 300, about 350, about 400, about 450, about 500 or more phosphates.

In some embodiments, it is contemplated that a nanoconjugate comprising a polynucleotide which comprises a domain is taken up by a cell with lower efficiency than a nanoconjugate comprising the same polynucleotide but lacking the domain. In various aspects, a nanoconjugate comprising a polynucleotide which comprises a domain is taken up by a cell about 2-fold, about 3-fold, about 4-fold, about 5-fold, about 6-fold, about 7-fold, about 8-fold, about 9-fold, about 10-fold, about 20-fold, about 30-fold, about 40-fold, about 50-fold, about 100-fold or higher, less efficiently than a nanoconjugate comprising the same polynucleotide but lacking the domain.

A surface density adequate to make the nanoconjugates stable and the conditions necessary to obtain it for a desired combination of nanoconjugates and polynucleotides can be determined empirically. Generally, a surface density of at least 2 pmol/cm$^2$ will be adequate to provide stable nanoconjugate-polynucleotide compositions. In some aspects, the surface density is at least 15 pmol/cm$^2$. In additional aspects, the polynucleotide is associated with the nanoconjugate at a surface density of about 0.3 pmol/cm$^2$ to about 10 pmol/cm$^2$, or from about 0.6 pmol/cm$^2$ to about 15 pmol/cm$^2$, or from about 1 pmol/cm$^2$ to about 20 pmol/cm$^2$, or from about 0.3 pmol/cm$^2$ to about 100 pmol/cm$^2$. Methods are also provided wherein the polynucleotide is associate with the nanoconjugate at a surface density of at least 2 pmol/cm$^2$, at least 3 pmol/cm$^2$, at least 4 pmol/cm$^2$, at least 5 pmol/cm$^2$, at least 6 pmol/cm$^2$, at least 7 pmol/cm$^2$, at least 8 pmol/cm$^2$, at least 9 pmol/cm$^2$, at least 10 pmol/cm$^2$, at least about 15 pmol/cm$^2$, at least about 19 pmol/cm$^2$, at least about 20 pmol/cm$^2$, at least about 25 pmol/cm$^2$, at least about 30 pmol/cm$^2$, at least about 35 pmol/cm$^2$, at least about 40 pmol/cm$^2$, at least about 45 pmol/cm$^2$, at least about 50 pmol/cm$^2$, at least about 55 pmol/cm$^2$, at least about 60 pmol/cm$^2$, at least about 65 pmol/cm$^2$, at least about 70 pmol/cm², at least about 75 pmol/cm², at least about 80 pmol/cm², at least about 85 pmol/cm², at least about 90 pmol/cm², at least about 95 pmol/cm², at least about 100 pmol/cm², at least about 125 pmol/cm², at least about 150 pmol/cm² at least about 175 pmol/cm², at least about 200 pmol/cm², at least about 250 pmol/cm², at least about 300 pmol/cm² at least about 350 pmol/cm², at least about 400 pmol/cm² at least about 450 pmol/cm², at least about 500 pmol/cm², at least about 550 pmol/cm² at least about 600 pmol/cm², at least about 650 pmol/cm², at least about 700 pmol/cm² at least about 750 pmol/cm², at least about 800 pmol/cm², at least about 850 pmol/cm² at least about 900 pmol/cm², at least about 950 pmol/cm², at least about 1000 pmol/cm² or more.

As used herein, a "conjugation site" is understood to mean a site on a polynucleotide to which a contrast agent is attached. Methods of attaching a contrast agent to a polynucleotide are generally known in the art [see, for example, Song et al., Chem Ing Engl 48(48): 9143-9147 (2009)]. In certain aspects, the disclosure also provides one or more polynucleotides that are part of the nanoconjugate do not comprise a conjugation site while one or more polynucleotides that are part of the same nanoconjugate do comprise a conjugation site. Conjugation of a contrast agent to a nanoconjugate through a conjugation site is generally described in PCT/US2010/44844, which is incorporated herein by reference in its entirety. The disclosure provides, in one aspect, a nanoconjugate comprising a polynucleotide wherein the polynucleotide comprises one to about ten conjugation sites. In another aspect, the polynucleotide comprises five conjugation sites. In general, for a nucleotide, both its backbone (phosphate group) and nucleobase can be modified. Accordingly, the present disclosure contemplates that there are 2n conjugation sites, where n=length of the polynucleotide template. In related aspects, it is contemplated that the composition comprises a nanoconjugate comprising a plurality of polynucleotides. In some aspects, the plurality of polynucleotides comprises at least one polynucleotide to which contrast agents are associated through one or more conjugation sites, as well as at least one polynucleotide that has gene regulatory activity as described herein.

Accordingly, in some embodiments, it is contemplated that one or more polynucleotides that are part of the nanoconjugate is not conjugated to a contrast agent while one or more polynucleotides that are part of the same nanoconjugate are conjugated to a contrast agent.

Polynucleotide Marker/Label

A polynucleotide as described herein, in various aspects, optionally comprises a detectable label. Accordingly, the disclosure provides compositions and methods wherein polynucleotide hybridization is detected by a detectable change. In one aspect, hybridization gives rise to a color change which is observed with the naked eye or spectroscopically.

Methods for visualizing the detectable change resulting from polynucleotide hybridization also include any fluorescent detection method, including without limitation fluorescence microscopy, a microtiter plate reader or fluorescence-activated cell sorting (FACS).

It will be understood that a label contemplated by the disclosure includes any of the fluorophores described herein as well as other detectable labels known in the art. For example, labels also include, but are not limited to, redox active probes, chemiluminescent molecules, radioactive labels, dyes, fluorescent molecules, phosphorescent molecules, imaging and/or contrast agents as described below, quantum dots, as well as any marker which can be detected using spectroscopic means, i.e., those markers detectable using microscopy and cytometry. In aspects of the disclosure wherein a detectable label is to be detected, the disclosure provides that any luminescent, fluorescent, or phosphorescent molecule or particle can be efficiently quenched by noble metal surfaces, or by a quencher molecule known in the art (quencher molecules contemplated by the disclosure include but are not limited to Dabsyl (dimethylamino-azobenzenesulfonic acid), Black Hole Quenchers, Qxl quenchers, Iowa black FQ, Iowa black RQ, IRDye QC-1 and a combination thereof). Accordingly, each type of molecule is contemplated for use in the compositions and methods disclosed.

Methods of labeling biomolecules with fluorescent molecules and measuring fluorescence are well known in the art.

Suitable fluorescent molecules are also well known in the art and include without limitation 1,8-ANS (1-Anilinonaphthalene-8-sulfonic acid), 1-Anilinonaphthalene-8-sulfonic acid (1,8-ANS), 5-(and -6)-Carboxy-2',7'-dichlorofluorescein pH 9.0, 5-FAM pH 9.0, 5-ROX (5-Carboxy-X-rhodamine, triethylammonium salt), 5-ROX pH 7.0, 5-TAMRA, 5-TAMRA pH 7.0, 5-TAMRA-MeOH, 6 JOE, 6,8-Difluoro-7-hydroxy-4-methylcoumarin pH 9.0, 6-Carboxyrhodamine 6G pH 7.0, 6-Carboxyrhodamine 6G, hydrochloride, 6-HEX, SE pH 9.0, 6-TET, SE pH 9.0, 7-Amino-4-methylcoumarin pH 7.0, 7-Hydroxy-4-methylcoumarin, 7-Hydroxy-4-methylcoumarin pH 9.0, Alexa 350, Alexa 405, Alexa 430, Alexa 488, Alexa 532, Alexa 546, Alexa 555, Alexa 568, Alexa 594, Alexa 647, Alexa 660, Alexa 680, Alexa 700, Alexa Fluor 430 antibody conjugate pH 7.2, Alexa Fluor 488 antibody conjugate pH 8.0, Alexa Fluor 488 hydrazide-water, Alexa Fluor 532 antibody conjugate pH 7.2, Alexa Fluor 555 antibody conjugate pH 7.2, Alexa Fluor 568 antibody conjugate pH 7.2, Alexa Fluor 610 R-phycoerythrin streptavidin pH 7.2, Alexa Fluor 647 antibody conjugate pH 7.2, Alexa Fluor 647 R-phycoerythrin streptavidin pH 7.2, Alexa Fluor 660 antibody conjugate pH 7.2, Alexa Fluor 680 antibody conjugate pH 7.2, Alexa Fluor 700 antibody conjugate pH 7.2, Allophycocyanin pH 7.5, AMCA conjugate, Amino Coumarin, APC (allophycocyanin), Atto 647, BCECF pH 5.5, BCECF pH 9.0, BFP (Blue Fluorescent Protein), BO-PRO-1-DNA, BO-PRO-3-DNA, BOBO-1-DNA, BOBO-3-DNA, BODIPY 650/665-X, MeOH, BODIPY FL conjugate, BODIPY FL, MeOH, Bodipy R6G SE, BODIPY R6G, MeOH, BODIPY TMR-X antibody conjugate pH 7.2, Bodipy TMR-X conjugate, BODIPY TMR-X, MeOH, BODIPY TMR-X, SE, BODIPY TR-X phallacidin pH 7.0, BODIPY TR-X, MeOH, BODIPY TR-X, SE, BOPRO-1, BOPRO-3, Calcein, Calcein pH 9.0, Calcium Crimson, Calcium Crimson Ca2+, Calcium Green, Calcium Green-1 Ca2+, Calcium Orange, Calcium Orange Ca2+, Carboxynaphthofluorescein pH 10.0, Cascade Blue, Cascade Blue BSA pH 7.0, Cascade Yellow, Cascade Yellow antibody conjugate pH 8.0, CFDA, CFP (Cyan Fluorescent Protein), CI-NERF pH 2.5, CI-NERF pH 6.0, Citrine, Coumarin, Cy 2, Cy 3, Cy 3.5, Cy 5, Cy 5.5, CyQUANT GR-DNA, Dansyl Cadaverine, Dansyl Cadaverine, MeOH, DAPI, DAPI-DNA, Dapoxyl (2-aminoethyl) sulfonamide, DDAO pH 9.0, Di-8 ANEPPS, Di-8-ANEPPS-lipid, DiI, DiO, DM-NERF pH 4.0, DM-NERF pH 7.0, DsRed, DTAF, dTomato, eCFP (Enhanced Cyan Fluorescent Protein), eGFP (Enhanced Green Fluorescent Protein), Eosin, Eosin antibody conjugate pH 8.0, Erythrosin-5-isothiocyanate pH 9.0, Ethidium Bromide, Ethidium homodimer, Ethidium homodimer-1-DNA, eYFP (Enhanced Yellow Fluorescent Protein), FDA, FITC, FITC antibody conjugate pH 8.0, FlAsH, Fluo-3, Fluo-3 Ca2+, Fluo-4, Fluor-Ruby, Fluorescein, Fluorescein 0.1 M NaOH, Fluorescein antibody conjugate pH 8.0, Fluorescein dextran pH 8.0, Fluorescein pH 9.0, Fluoro-Emerald, FM 1-43, FM 1-43 lipid, FM 4-64, FM 4-64, 2% CHAPS, Fura Red Ca2+, Fura Red, high Ca, Fura Red, low Ca, Fura-2 Ca2+, Fura-2, high Ca, Fura-2, no Ca, GFP (S65T), HcRed, Hoechst 33258, Hoechst 33258-DNA, Hoechst 33342, Indo-1 Ca2+, Indo-1, Ca free, Indo-1, Ca saturated, JC-1, JC-1 pH 8.2, Lissamine rhodamine, LOLO-1-DNA, Lucifer Yellow, CH, LysoSensor Blue, LysoSensor Blue pH 5.0, LysoSensor Green, LysoSensor Green pH 5.0, LysoSensor Yellow pH 3.0, LysoSensor Yellow pH 9.0, LysoTracker Blue, LysoTracker Green, LysoTracker Red, Magnesium Green, Magnesium Green Mg2+, Magnesium Orange, Marina Blue, mBanana, mCherry, mHoneydew, MitoTracker Green, MitoTracker Green FM, MeOH, MitoTracker Orange, MitoTracker Orange, MeOH, MitoTracker Red, MitoTracker Red, MeOH, mOrange, mPlum, mRFP, mStrawberry, mTangerine, NBD-X, NBD-X, MeOH, NeuroTrace 500/525, green fluorescent Nissl stain-RNA, Nile Blue, EtOH, Nile Red, Nile Red-lipid, Nissl, Oregon Green 488, Oregon Green 488 antibody conjugate pH 8.0, Oregon Green 514, Oregon Green 514 antibody conjugate pH 8.0, Pacific Blue, Pacific Blue antibody conjugate pH 8.0, Phycoerythrin, PicoGreen dsDNA quantitation reagent, PO-PRO-1, PO-PRO-1-DNA, PO-PRO-3, PO-PRO-3-DNA, POPO-1, POPO-1-DNA, POPO-3, Propidium Iodide, Propidium Iodide-DNA, R-Phycoerythrin pH 7.5, ReAsH, Resorufin, Resorufin pH 9.0, Rhod-2, Rhod-2 Ca2+, Rhodamine, Rhodamine 110, Rhodamine 110 pH 7.0, Rhodamine 123, MeOH, Rhodamine Green, Rhodamine phalloidin pH 7.0, Rhodamine Red-X antibody conjugate pH 8.0, Rhodaminen Green pH 7.0, Rhodol Green antibody conjugate pH 8.0, Sapphire, SBFI-Na+, Sodium Green Na+, Sulforhodamine 101, EtOH, SYBR Green I, SYPRO Ruby, SYTO 13-DNA, SYTO 45-DNA, SYTOX Blue-DNA, Tetramethylrhodamine antibody conjugate pH 8.0, Tetramethylrhodamine dextran pH 7.0, Texas Red-X antibody conjugate pH 7.2, TO-PRO-1-DNA, TO-PRO-3-DNA, TOTO-1-DNA, TOTO-3-DNA, TRITC, X-Rhod-1 Ca2+, YO-PRO-1-DNA, YO-PRO-3-DNA, YOYO-1-DNA, and YOYO-3-DNA.

Polypeptides

Nanoconjugates, in various aspects, comprise a polypeptide. The polypeptide may be associated with the nanoconjugate or may be delivered in a composition with a nanoconjugate as, in some embodiments, a therapeutic agent. As used herein a "polypeptide" refers to a polymer comprised of amino acid residues. Polypeptides are understood in the art and include without limitation an antibody, an enzyme and a hormone. In related aspects, the nanoconjugate comprising a polypeptide recognizes and associates with a target molecule and enables detection of the target molecule.

Polypeptides of the disclosure may be either naturally occurring or non-naturally occurring. Polypeptides optionally include a spacer as described herein above.

Naturally Occurring Polypeptides

Naturally occurring polypeptides include without limitation biologically active polypeptides (including antibodies) that exist in nature or can be produced in a form that is found in nature by, for example, chemical synthesis or recombinant expression techniques. Naturally occurring polypeptides also include lipoproteins and post-translationally modified proteins, such as, for example and without limitation, glycosylated proteins.

Antibodies contemplated for use in the methods and compositions of the present disclosure include without limitation antibodies that recognize and associate with a target molecule either in vivo or in vitro.

Non-Naturally Occurring Polypeptides

Non-naturally occurring polypeptides contemplated by the present disclosure include but are not limited to synthetic polypeptides, as well as fragments, analogs and variants of naturally occurring or non-naturally occurring polypeptides as defined herein. Non-naturally occurring polypeptides also include proteins or protein substances that have D-amino acids, modified, derivatized, or non-naturally occurring amino acids in the D- or L-configuration and/or peptidomimetic units as part of their structure. The term "protein" typically refers to large polypeptides. The term "peptide" typically refers to short (i.e., equal to or less than about 50 amino acids) polypeptides.

Non-naturally occurring polypeptides are prepared, for example, using an automated polypeptide synthesizer or, alternatively, using recombinant expression techniques using a modified polynucleotide which encodes the desired polypeptide.

As used herein a "fragment" of a polypeptide is meant to refer to any portion of a polypeptide or protein smaller than the full-length polypeptide or protein expression product.

As used herein an "analog" refers to any of two or more polypeptides substantially similar in structure and having the same biological activity, but can have varying degrees of activity, to either the entire molecule, or to a fragment thereof. Analogs differ in the composition of their amino acid sequences based on one or more mutations involving substitution, deletion, insertion and/or addition of one or more amino acids for other amino acids. Substitutions can be conservative or non-conservative based on the physico-chemical or functional relatedness of the amino acid that is being replaced and the amino acid replacing it.

As used herein a "variant" refers to a polypeptide, protein or analog thereof that is modified to comprise additional chemical moieties not normally a part of the molecule. Such moieties may modulate, for example and without limitation, the molecule's solubility, absorption, and/or biological half-life. Moieties capable of mediating such effects are disclosed in Remington's Pharmaceutical Sciences (1980). Procedures for coupling such moieties to a molecule are well known in the art. In various aspects, polypeptides are modified by glycosylation, PEGylation, and/or polysialylation.

Fusion proteins, including fusion proteins wherein one fusion component is a fragment or a mimetic, are also contemplated. A "mimetic" as used herein means a peptide or protein having a biological activity that is comparable to the protein of which it is a mimetic. By way of example, an endothelial growth factor mimetic is a peptide or protein that has a biological activity comparable to the native endothelial growth factor. The term further includes peptides or proteins that indirectly mimic the activity of a protein of interest, such as by potentiating the effects of the natural ligand of the protein of interest.

Polypeptides include antibodies along with fragments and derivatives thereof, including but not limited to Fab' fragments, F(ab)$_2$ fragments, Fv fragments, Fc fragments, one or more complementarity determining regions (CDR) fragments, individual heavy chains, individual light chain, dimeric heavy and light chains (as opposed to heterotetrameric heavy and light chains found in an intact antibody, single chain antibodies (scAb), humanized antibodies (as well as antibodies modified in the manner of humanized antibodies but with the resulting antibody more closely resembling an antibody in a non-human species), chelating recombinant antibodies (CRABS), bispecific antibodies and multispecific antibodies; and other antibody derivative or fragments known in the art.

Contrast Agents

Disclosed herein are, in various aspects, methods and compositions comprising a nanoconjugate, wherein a biomolecule is conjugated to a contrast agent through a conjugation site. In various aspects, a contrast agent is conjugated to a polynucleotide and/or a polypeptide. As used herein, a "contrast agent" is a compound or other substance introduced into a cell in order to create a difference in the apparent density of various organs and tissues, making it easier to see the delineate adjacent body tissues and organs. It will be understood that conjugation of a contrast agent to a polynucleotide or polypeptide described herein is useful in the compositions and methods of the disclosure.

Methods provided by the disclosure include those wherein relaxivity of the contrast agent in association with a nanoconjugate is increased relative to the relaxivity of the contrast agent in the absence of being associated with a nanoconjugate. In some aspects, the increase is about 1-fold to about 20-fold. In further aspects, the increase is about 2-fold fold to about 10-fold, and in yet further aspects the increase is about 3-fold.

In some embodiments, the contrast agent is selected from the group consisting of gadolinium, xenon, iron oxide, a manganese chelate (Mn-DPDP) and copper. Thus, in some embodiments the contrast agent is a paramagnetic compound, and in some aspects, the paramagnetic compound is gadolinium.

The present disclosure also contemplates contrast agents that are useful for positron emission tomography (PET) scanning. In some aspects, the PET contrast agent is a radionuclide. In certain embodiments the contrast agent comprises a PET contrast agent comprising a label selected from the group consisting of $^{11}C$, $^{13}N$, $^{18}F$, $^{64}Cu$, $^{68}Ge$, $^{99m}Tc$ and $^{82}Ru$. In particular embodiments the contrast agent is a PET contrast agent selected from the group consisting of [$^{11}C$]choline, [$^{18}F$]-fluorodeoxyglucose(FDG), [$^{11}C$]methionine, [$^{11}C$]choline, [$^{11}C$]acetate, [$^{18}F$]fluorocholine, $^{64}Cu$ chelates, $^{99m}Tc$ chelates, and [$^{18}F$]polyethyleneglycol stilbenes.

The disclosure also provides methods wherein a PET contrast agent is introduced into a polynucleotide during the polynucleotide synthesis process or is conjugated to a nucleotide following polynucleotide synthesis. For example and without limitation, nucleotides can be synthesized in which one of the phosphorus atoms is replaced with $^{32}P$ or $^{33}P$, one of the oxygen atoms in the phosphate group is replaced with $^{35}S$, or one or more of the hydrogen atoms is replaced with $^3H$. A functional group containing a radionuclide can also be conjugated to a nucleotide through conjugation sites.

In certain embodiments, the MRI contrast agent conjugated to a polynucleotide is iron or paramagnetic radiotracers and/or complexes, including but not limited to gadolinium, xenon, iron oxide, and copper. MRI contrast agents can include, but are not limited to positive contrast agents and/or negative contrast agents. Positive contrast agents cause a reduction in the $T_1$ relaxation time (increased signal intensity on $T_1$ weighted images). They (appearing bright on MRI) are typically small molecular weight compounds containing as their active element Gadolinium, Manganese, or Iron. All of these elements have unpaired electron spins in their outer shells and long relaxivities. A special group of negative contrast agents (appearing dark on MRI) include perfluorocarbons (perfluorochemicals), because their presence excludes the hydrogen atoms responsible for the signal in MR imaging.

The composition of the disclosure, in various aspects, is contemplated to comprise a nanoconjugate that comprises about 50 to about $2.5 \times 10^6$ contrast agents. In some embodiments, the nanoconjugate comprises about 500 to about $1 \times 10^6$ contrast agents.

Targeting Moiety

The term "targeting moiety" as used herein refers to any molecular structure which assists a compound or other molecule in binding or otherwise localizing to a particular target, a target area, entering target cell(s), or binding to a target receptor. For example and without limitation, targeting moieties may include proteins, including antibodies and protein fragments capable of binding to a desired target site in vivo or in vitro, peptides, small molecules, anticancer agents, polynucleotide-binding agents, carbohydrates, ligands for cell surface receptors, aptamers, lipids (including cationic, neutral, and steroidal lipids, virosomes, and liposomes), antibodies and hormones may serve as targeting moieties. Targeting moieties are useful for delivery of the nanoconjugate to specific cell types, as well as sub-cellular locations.

Receptor-mediated transport mechanisms are present at the BBB, and these involve the vesicular trafficking system of the brain endothelium [Jones et al., Pharm Res. 24(9): 1759-1771 (2007)]. Brain influx of nutrients such as iron [Jefferies et al., Nature 312: 162-163 (1984)], insulin [Duffy et al., Brain Res 420: 32-38 (1987)], and leptin [Golden et al., J Clin Invest 99: 14-18 (1997)] occurs by a transcellular, receptor-mediated transport mechanism known as transcytosis.

In some embodiments, the targeting moiety is a protein. The protein portion of the composition of the present disclosure is, in some aspects, a protein capable of targeting the composition to a target cell. The targeting protein of the present disclosure may bind to a receptor, substrate, antigenic determinant, or other binding site on a target cell or other target site.

Antibodies useful as targeting proteins may be polyclonal or monoclonal. A number of monoclonal antibodies (MAbs) that bind to a specific type of cell have been developed. Antibodies derived through genetic engineering or protein engineering may be used as well (e.g., IgG, IgA, IgM, IgD, IgE antibodies).

The antibody employed as a targeting agent in the present disclosure may be an intact molecule, a fragment thereof, or a functional equivalent thereof. Examples of antibody fragments useful in the compositions of the present disclosure are F(ab')$_2$, Fab' Fab and Fv fragments, which may be produced by conventional methods or by genetic or protein engineering.

In additional aspects, targeting moieties contemplated by the disclosure include, but are not limited to sugars (e.g., mannose, mannose-6-phosphate, galactose). In further aspects, the moiety targets any one or a combination of the transferrin receptor (TfR), which is highly expressed by brain capillaries to mediate the delivery of iron to the brain [Jefferies et al., Nature 312: 162-163 (1984)]; the insulin receptor and insulin-like growth factor receptor [Duffy et al., Brain Res 420:32-38 (1987)]; the low density lipoprotein receptor-related protein 1 and low density lipoprotein receptor-related protein 2 [Gaillard et al., Expert Opin Drug Deliv 2:299-309 (2005)]; and the diphtheria toxin receptor/heparin binding epidermal growth factor-like growth factor [Gaillard et al., Int Congres. Series 1277:185-198 (2005)]. Additional moieties contemplated by the disclosure that are capable of effecting receptor-mediated transcytosis (RMT) include, but are not limited to, those disclosed in Feng et al. [In: *Drug Delivery to the Central Nervous System*, Kewal K. Jain (Editor), vol. 45: 15-34 (2010)].

In some embodiments, the polynucleotide portion of the nanoconjugate may serve as an additional or auxiliary targeting moiety. The polynucleotide portion may be selected or designed to assist in extracellular targeting, or to act as an intracellular targeting moiety. That is, the polynucleotide portion may act as a DNA probe seeking out target cells. This additional targeting capability will serve to improve specificity in delivery of the composition to target cells. The polynucleotide may additionally or alternatively be selected or designed to target the composition within target cells, while the targeting protein targets the conjugate extracellularly.

It is contemplated that the targeting moiety can, in various embodiments, be associated with a nanoconjugate. In aspects wherein the nanoconjugate comprises a nanoparticle (i.e., is not hollow), it is contemplated that the targeting moiety is attached to either the nanoparticle, the polynucleotide/polypeptide or both. In further aspects, the targeting moiety is associated with the nanoconjugate composition, and in other aspects the targeting moiety is administered before, concurrent with, or after the administration of a composition of the disclosure.

Therapeutic Agents

In any of the aspects or embodiments of the disclosure, it is contemplated that a therapeutic agent is delivered with a nanoconjugate. Such delivery can be, in various embodiments, facilitated by associating the therapeutic agent with a nanoconjugate, or delivery can be facilitated by co-administering the therapeutic agent with a nanoconjugate. Methods for associating a therapeutic agent to a nanoconjugate are known in the art and described, for example and without limitation, in International Patent Application Number PCT/US2010/055018, which is incorporated by reference herein in its entirety. In some embodiments, the therapeutic agent is a neurotrophic factor.

Neurotrophins

Many neurotrophic factors are neuroprotective in brain, but do not cross the blood-brain barrier. These factors are suitable for use in the compositions and methods of the disclosure and include brain-derived neurotrophic factor (BDNF), nerve growth factor (NGF), neurotrophin-4/5, fibroblast growth factor (FGF)-2 and other FGFs, neurotrophin (NT)-3, erythropoietin (EPO), hepatocyte growth factor (HGF), epidermal growth factor (EGF), transforming growth factor (TGF)-α, TGF-β, vascular endothelial growth factor (VEGF), interleukin-1 receptor antagonist (IL-1ra), ciliary neurotrophic factor (CNTF), glial-derived neurotrophic factor (GDNF), neurturin, platelet-derived growth factor (PDGF), heregulin, neuregulin, artemin, persephin, interleukins, granulocyte-colony stimulating factor (CSF), granulocyte-macrophage-CSF, netrins, cardiotrophin-1, hedgehogs, leukemia inhibitory factor (LIF), midkine, pleiotrophin, bone morphogenetic proteins (BMPs), netrins, saposins, semaphorins, and stem cell factor (SCF).

Anticancer Agent

In some aspects, a composition of the disclosure comprises an anticancer agent. Suitable anticancer agents include, but are not limited to, Actinomycin D, Alemtuzumab, Allopurinol sodium, Amifostine, Amsacrine, Anastrozole, Ara-CMP, Asparaginase, Azacytadine, Bendamustine, Bevacizumab, Bicalutimide, Bleomycin (e.g., Bleomycin $A_2$ and $B_2$), Bortezomib, Busulfan, Camptothecin sodium salt, Capecitabine, Carboplatin, Carmustine, Cetuximab, Chlorambucil, Cisplatin, Cladribine, Clofarabine, Cyclophosphamide, Cytarabine, Dacarbazine, Dactinomycin, Daunorubicin, Daunorubicin liposomal, Dacarbazine, Decitabine, Docetaxel, Doxorubicin, Doxorubicin liposomal, Epirubicin, Estramustine, Etoposide, Etoposide phosphate, Exemestane, Floxuridine, Fludarabine, Fluadarabine phosphate, 5-Fluorouracil, Fotemustine, Fulvestrant, Gemcitabine, Goserelin, Hexamethylmelamine, Hydroxyurea, Idarubicin, Ifosfamide, Imatinib, Irinotecan, Ixabepilone, Lapatinib, Letrozole, Leuprolide acetate, Lomustine, Mechlorethamine, Melphalan, 6-Mercaptopurine, Methotrexate, Mithramycin, Mitomycin C, Mitotane, Mitoxantrone, Nimustine, Ofatumumab, Oxaliplatin, Paclitaxel, Panitumumab, Pegaspargase, Pemetrexed, Pentostatin, Pertuzumab, Picoplatin, Pipobroman, Plerixafor, Procarbazine, Raltitrexed, Rituximab, Streptozocin, Temozolomide, Teniposide, 6-Thioguanine, Thiotepa, Topotecan, Trastuzumab, Treosulfan, Triethylenemelamine, Trimetrexate, Uracil Nitrogen Mustard, Valrubicin, Vinblastine, Vincristine, Vindesine, Vinorelbine, and analogues, precursors, derivatives and pro-drugs thereof. It is noted that two or more of the above compounds may be used in combination in the compositions of the disclosure.

Small Molecule

The term "small molecule," as used herein, refers to a chemical compound, for instance a peptidometic that may optionally be derivatized, or any other low molecular weight organic compound, either natural or synthetic. Such small molecules may be a therapeutically deliverable substance or may be further derivatized to facilitate delivery.

By "low molecular weight" is meant compounds having a molecular weight of less than 1000 Daltons, typically between 300 and 700 Daltons. Low molecular weight compounds, in various aspects, are about 100, about 150, about 200, about 250, about 300, about 350, about 400, about 450, about 500, about 550, about 600, about 650, about 700, about 750, about 800, about 850, about 900, or about 1000 Daltons.

Methods

The disclosure provides compositions comprising a nanoconjugate that are able to cross the BBB. Such compositions are useful, in various aspects, for the treatment of acute and chronic disorders of the CNS. For example and without limitation, the compositions of the disclosure are useful in the treatment of acute brain and spinal cord conditions, such as focal brain ischemia, global brain ischemia, and spinal cord injury, and chronic treatment of neurodegenerative disease, including prion diseases, Alzheimer's disease (AD), Parkinson's disease (PD), Huntington's disease (HD), ALS, multiple sclerosis, transverse myelitis, motor neuron disease, Pick's disease, tuberous sclerosis, lysosomal storage disorders, Canavan's disease, Rett's syndrome, spinocerebellar ataxias, Friedreich's ataxia, optic atrophy, and retinal degeneration. Also contemplated for treatment are lower motor neuron diseases such as SMA and ALS as well as Pompe disease, lysosomal storage disorders, Glioblastoma multiforme and Parkinson's disease. Lysosomal storage disorders include, but are not limited to, Activator Deficiency/GM2 Gangliosidosis, Alpha-mannosidosis, Aspartylglucosaminuria, Cholesteryl ester storage disease, Chronic Hexosaminidase A Deficiency, Cystinosis, Danon disease, Fabry disease, Farber disease, Fucosidosis, Galactosialidosis, Gaucher Disease (Type I, Type II, Type III), GM1 gangliosidosis (Infantile, Late infantile/Juvenile, Adult/Chronic), I-Cell disease/Mucolipidosis II, Infantile Free Sialic Acid Storage Disease/ISSD, Juvenile Hexosaminidase A Deficiency, Krabbe disease (Infantile Onset, Late Onset), Metachromatic Leukodystrophy, Mucopolysaccharidoses disorders (Pseudo-Hurler polydystrophy/Mucolipidosis IIIA, MPSI Hurler Syndrome, MPSI Scheie Syndrome, MPS I Hurler-Scheie Syndrome, MPS II Hunter syndrome, Sanfilippo syndrome Type A/MPS III A, Sanfilippo syndrome Type B/MPS III B, Sanfilippo syndrome Type C/MPS III C, Sanfilippo syndrome Type D/MPS III D, Morquio Type A/MPS IVA, Morquio Type B/MPS IVB, MPS IX Hyaluronidase Deficiency, MPS VI Maroteaux-Lamy, MPS VII Sly Syndrome, Mucolipidosis I/Sialidosis, Mucolipidosis IIIC, Mucolipidosis type IV), Multiple sulfatase deficiency, Niemann-Pick Disease (Type A, Type B, Type C), Neuronal Ceroid Lipofuscinoses (CLN6 disease (Atypical Late Infantile, Late Onset variant, Early Juvenile), Batten-Spielmeyer-Vogt/Juvenile NCL/CLN3 disease, Finnish Variant Late Infantile CLN5, Jansky-Bielschowsky disease/Late infantile CLN2/TPP1 Disease, Kufs/Adult-onset NCL/CLN4 disease, Northern Epilepsy/variant late infantile CLN8, Santavuori-Haltia/Infantile CLN1/PPT disease, Beta-mannosidosis, Pompe disease/Glycogen storage disease type II, Pycnodysostosis, Sandhoff Disease/Adult Onset/GM2 Gangliosidosis, Sandhoff Disease/GM2 gangliosidosis—Infantile, Sandhoff Disease/GM2 gangliosidosis—Juvenile, Schindler disease, Salla disease/Sialic Acid Storage Disease, Tay-Sachs/GM2 gangliosidosis, and/or Wolman disease. In further embodiments, use of the methods and materials is indicated for treatment of nervous system disease such as Rett Syndrome, along with nervous system injury including spinal cord and brain trauma/injury, stroke, and brain cancers.

In some aspects, a composition of the disclosure comprises a polypeptide that is a trophic or protective factor. In some embodiments, the trophic or protective factor is co-administered with a nanoconjugate of the disclosure. In various embodiments, use of a trophic or protective factor is indicated for neurodegenerative disorders contemplated herein, including but not limited to Alzheimer's Disease, Parkinson's Disease, Huntington's Disease along with nervous system injury including spinal cord and brain trauma/injury, stroke, and brain cancers. Non-limiting examples of known nervous system growth factors include nerve growth factor (NGF), brain-derived neurotrophic factor (BDNF), neurotrophin-3 (NT-3), neurotrophin-4/5 (NT-4/5), neurotrophin-6 (NT-6), ciliary neurotrophic factor (CNTF), glial cell line-derived neurotrophic factor (GDNF), the fibroblast growth factor family (e.g., FGF's 1-15), leukemia inhibitory factor (LIF), certain members of the insulin-like growth factor family (e.g., IGF-1), the neurturins, persephin, the bone morphogenic proteins (BMPs), the immunophilins, the transforming growth factor (TGF) family of growth factors, the neuregulins, epidermal growth factor (EGF), platelet-derived growth factor (PDGF), vascular endothelial growth factor family (e.g., VEGF 165), follistatin, and Hifl. Also generally contemplated are zinc finger transcription factors that regulate each of the trophic or protective factors contemplated herein. In further embodiments, methods to modulate neuro-immune function are contemplated, including but not limited to, inhibition of microglial and astroglial activation through, for example, NFκB inhibition, or NFκB for neuroprotection (dual action of NFκB and associated pathways in different cell types.) by siRNA, shRNA, antisense, or miRNA. As is understood by one of skill in the art, any one or more of the aforementioned inhibitory RNAs is, in various embodiments, associated with a nanoconjugate as described herein.

In still further embodiments, the nanoconjugate comprises a polynucleotide that specifically hybridizes to and inhibits a Bcl-2 family member. In one embodiment, the Bcl-2 family member is Bcl2L12.

In some embodiments, use of materials and methods of the disclosure is indicated for neurodegenerative disorders such as Parkinson's disease. In various embodiments, the nanoconjugate is co-administered with Aromatic acid dopa decarboxylase (AADC), Tyrosine hydroxylase, GTP-cyclohydrolase 1 (gtpch1), an apoptotic inhibitor (e.g., bcl2, bclxL), glial cell line-derived neurotrophic factor (GDNF), the inhibitory neurotransmitter-amino butyric acid (GABA), and enzymes involved in dopamine biosynthesis. In further embodiments, the nanoconjugate is co-administered with a modifier of Parkin and/or synuclein.

In some embodiments, use of materials and methods of the disclosure is indicated for neurodegenerative disorders such as Alzheimer's disease. In further embodiments, methods to increase acetylcholine production are contemplated. In still further embodiments, methods of increasing the level of a choline acetyltransferase (ChAT) or inhibiting the activity of an acetylcholine esterase (AchE) are contemplated.

In some embodiments, the nanoconjugate comprises a polynucleotide that inhibits mutant Huntington protein (htt) expression through siRNA, shRNA, antisense, and/or miRNA for treating a neurodegenerative disorder such as Huntington's disease.

In some embodiments, use of materials and methods of the disclosure is indicated for neurodegenerative disorders such as ALS. In some aspects, treatment with the embodiments contemplated by the disclosure results in a decrease in the expression of molecular markers of disease, such as TNFα, nitric oxide, peroxynitrite, and/or nitric oxide synthase (NOS).

In other aspects, the nanoconjugate comprises a short hairpin RNA directed at mutated proteins such as superoxide dismutase for ALS.

In some embodiments, use of materials and methods of the disclosure is indicated for preventing or treating neurodevelopmental disorders such as Rett Syndrome. For embodiments relating to Rett Syndrome, the nanoconjugate is co-administered with methyl cytosine binding protein 2 (MeCP2).

Methods of Inhibiting Gene Expression

Additional methods provided by the disclosure include methods of inhibiting expression of a gene product expressed from a target polynucleotide comprising contacting the target polynucleotide with a composition as described herein, wherein the contacting is sufficient to inhibit expression of the gene product. Inhibition of the gene product results from the hybridization of a target polynucleotide with a composition of the disclosure.

It is understood in the art that the sequence of a polynucleotide that is part of a nanoconjugate need not be 100% complementary to that of its target polynucleotide in order to specifically hybridize to the target polynucleotide. Moreover, a polynucleotide that is part of a nanoconjugate may hybridize to a target polynucleotide over one or more segments such that intervening or adjacent segments are not involved in the hybridization event (for example and without limitation, a loop structure or hairpin structure). The percent complementarity is determined over the length of the polynucleotide that is part of the nanoconjugate. For example, given a nanoconjugate comprising a polynucleotide in which 18 of 20 nucleotides of the polynucleotide are complementary to a 20 nucleotide region in a target polynucleotide of 100 nucleotides total length, the polynucleotide that is part of the nanoconjugate would be 90 percent complementary. In this example, the remaining noncomplementary nucleotides may be clustered or interspersed with complementary nucleotides and need not be contiguous to each other or to complementary nucleotides. Percent complementarity of a polynucleotide that is part of a nanoconjugate with a region of a target polynucleotide can be determined routinely using BLAST programs (basic local alignment search tools) and PowerBLAST programs known in the art (Altschul et al., J. Mol. Biol., 1990, 215, 403-410; Zhang and Madden, Genome Res., 1997, 7, 649-656).

Methods for inhibiting gene product expression provided include those wherein expression of the target gene product is inhibited by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, at least about 99%, or 100% compared to gene product expression in the absence of a nanoconjugate comprising a polynucleotide. In other words, methods provided embrace those which results in essentially any degree of inhibition of expression of a target gene product.

The degree of inhibition is determined in vivo from a body fluid sample or from a biopsy sample or by imaging techniques well known in the art. Alternatively, the degree of inhibition is determined in vitro in a cell culture assay, generally as a predictable measure of a degree of inhibition that can be expected in vivo resulting from use of a composition as described herein. It is contemplated by the disclosure that the inhibition of a target polynucleotide is used to assess the effects of the inhibition on a given cell. By way of non-limiting example, one can study the effect of the inhibition of a gene product wherein the gene product is part of a signal transduction pathway. Alternatively, one can study the inhibition of a gene product wherein the gene product is hypothesized to be involved in an apoptotic pathway.

It will be understood that any of the methods described herein can be used in combination to achieve a desired result. For example and without limitation, methods described herein can be combined to allow one to both detect a target polynucleotide as well as regulate its expression. In some embodiments, this combination can be used to quantitate the inhibition of target polynucleotide expression over time either in vitro or in vivo. The quantitation over time is achieved, in one aspect, by removing cells from a culture at specified time points and assessing the relative level of expression of a target polynucleotide at each time point. A decrease in the amount of target polynucleotide as assessed, in one aspect, through visualization of a detectable label, over time indicates the rate of inhibition of the target polynucleotide.

Thus, determining the effectiveness of a given polynucleotide to hybridize to and inhibit the expression of a target polynucleotide, as well as determining the effect of inhibition of a given polynucleotide on a cell, are aspects that are contemplated.

Use of a Nanoconjugate as a Probe

The nanoconjugates are, in one aspect, used as probes in diagnostic assays for detecting a nucleic acid or a cell.

Some embodiments of the method of detecting a target nucleic acid utilize a substrate. Any substrate can be used which allows observation of the detectable change. Suitable substrates include transparent solid surfaces (e.g., glass, quartz, plastics and other polymers), opaque solid surface (e.g., white solid surfaces, such as TLC silica plates, filter paper, glass fiber filters, cellulose nitrate membranes, nylon membranes), and conducting solid surfaces (e.g., indium-tin-oxide (ITO)). The substrate can be any shape or thickness, but generally will be flat and thin. Preferred are transparent substrates such as glass (e.g.; glass slides) or plastics (e.g., wells of microtiter plates). Methods of attaching polynucleotides to a substrate and uses thereof with respect to nanoconjugates are disclosed in U.S. Patent Application 20020172953, incorporated herein by reference in its entirety:

By employing a substrate, the detectable change can be amplified and the sensitivity of the assay increased. In one aspect, the method comprises the steps of contacting a target polynucleotide with a substrate having a polynucleotide attached thereto, the polynucleotide (i) having a sequence complementary to a first portion of the sequence of the target nucleic acid, the contacting step performed under conditions effective to allow hybridization of the polynucleotide on the substrate with the target nucleic acid, and (ii) contacting the target nucleic acid bound to the substrate with a first type of nanoconjugate having a polynucleotide attached thereto, the polynucleotide having a sequence complementary to a second portion of the sequence of the target nucleic acid, the contacting step performed under conditions effective to allow hybridization of the polynucleotide that is part of the nanoconjugate with the target nucleic acid. Next, the first type of nanoconjugate bound to the substrate is contacted with a second type of nanoconjugate comprising a polynucleotide, the polynucleotide on the second type of nanoconjugate having a sequence complementary to at least a portion of the sequence of the polynucleotide used to produce the first type of nanoconjugate, the contacting step taking place under conditions effective to allow hybridization of the polynucleotides on the first and second types of nanoconjugates. Finally, a detectable change produced by these hybridizations is observed.

The detectable change that occurs upon hybridization of the polynucleotides on the nanoconjugates to the nucleic acid may be a color change, the formation of aggregates of the nanoconjugates, detection of a radiological marker, or the precipitation of the aggregated nanoconjugates. The color changes can be observed with the naked eye or spectroscopically. The formation of aggregates of the nanoconjugates can be observed by electron microscopy or by nephelometry. The precipitation of the aggregated nanoconjugates can be observed with the naked eye or microscopically. Preferred are changes observable with the naked eye. Particularly preferred is a color change observable with the naked eye.

The methods of detecting target nucleic acid hybridization based on observing a color change with the naked eye are cheap, fast, simple, robust (the reagents are stable), do not require specialized or expensive equipment, and little or no instrumentation is required. These advantages make them particularly suitable for use in, e.g., research and analytical laboratories in DNA sequencing, in the field to detect the presence of specific pathogens, in the doctor's office for quick identification of an infection to assist in prescribing a drug for treatment, and in homes and health centers for inexpensive first-line screening.

A nanoconjugate comprising a polynucleotide can be used in an assay to target a target molecule of interest. Thus, the nanoconjugate comprising a polynucleotide can be used in an assay such as a bio barcode assay. See, e.g., U.S. Pat. Nos. 6,361,944; 6,417,340; 6,495,324; 6,506,564; 6,582,921; 6,602,669; 6,610,491; 6,678,548; 6,677,122; 6682,895; 6,709,825; 6,720,147; 6,720,411; 6,750,016; 6,759,199; 6,767,702; 6,773,884; 6,777,186; 6,812,334; 6,818,753; 6,828,432; 6,827,979; 6,861,221; and 6,878,814, the disclosures of which are incorporated herein by reference.

In some embodiments, the compositions of the disclosure are useful in nano-flare technology. The nano-flare has been previously described in the context of polynucleotide-functionalized nanoparticles that can take advantage of a sicPN architecture for fluorescent detection of polynucleotide levels inside a living cell [described in WO 2008/098248 and U.S. Patent Application Publication Number U.S. 2011/0111974, each of which is incorporated by reference herein in its entirety]. In this system the sicPN acts as the "flare" and is detectably labeled and displaced or released from the surface by an incoming target polynucleotide. It is thus contemplated that the nano-flare technology is useful in the context of the nanoconjugates described herein.

Dosing and Pharmaceutical Compositions

It will be appreciated that any of the compositions described herein may be administered to a mammal in a therapeutically effective amount to achieve a desired therapeutic effect.

The compositions described herein may be formulated in pharmaceutical compositions with a pharmaceutically acceptable excipient, carrier, or diluent. The compound or composition can be administered by any route that permits treatment of, for example and without limitation, a disease, disorder or infection as described herein. Depending on the circumstances, a pharmaceutical composition is applied or instilled into body cavities, absorbed through the skin or mucous membranes, ingested, inhaled, and/or introduced into circulation. In some embodiments, a composition comprising a nanoconjugate is administered intravenously, intraarterially, or intraperitoneally to introduce the composition into circulation. Non-intravenous administration also is appropriate, particularly with respect to low molecular weight therapeutics. In certain circumstances, it is desirable to deliver a pharmaceutical composition comprising the nanoconjugate peripherally, orally, topically, sublingually, vaginally, rectally; through injection by intracerebral (intraparenchymal), intracerebroventricular, intramuscular, intraocular, intraportal, intralesional, intramedullary, intrathecal, intraventricular, transdermal, subcutaneous, intranasal, urethral, or enteral means; by sustained release systems; or by implantation devices.

Administration may take the form of single dose administration, or the compound of the embodiments can be administered over a period of time, either in divided doses or in a single dose. However the compounds of the embodiments are administered to the subject, the amounts of compound administered and the route of administration chosen should be selected to permit efficacious treatment of the disease condition. Administration of combinations of therapeutic agents (i.e., combination therapy) is also contemplated, and in some of these embodiments, at least one of the therapeutic agents is in association with a nanoconjugate as described herein.

In embodiments wherein a nanoconjugate is to be studied in a glioma cell line and/or patient-derived tumor neurospheres (TNS), it is contemplated that about 0.1 nM to about 10 nM, or about 0.5 nM to about 8 nM, or about 1 nM to about 10 nM, or about 0.1 nM to about 0.5 nM, or about 0.1 nM to about 5 nM are administered. In specific embodiments, it is contemplated that about 0.1, 0.2, 0.3, 0.4, 0.5, 0.6, 0.7, 0.8, 0.9, 1, 2, 3, 4, 5, 6, 7, 8, 9, 10 nM or more of the nanoconjugate is administered to a glioma cell line and/or patient-derived TNS. In some embodiments, the administration of the nanoconjugate proceeds for about 24-48, or about 24-36, or about 24-40, or about 36-48, or about 24, about 30, about 36, about 40, or about 48 hours or more.

In further embodiments, administration of a nanoconjugate composition as described herein is from about 1 mg/kg to about 50 mg/kg, or about 5 mg/kg to about 50 mg/kg, or from about 5 mg/kg to about 30 mg/kg, or from about 5 mg/kg to about 20 mg/kg, or from about 5 mg/kg to about 10 mg/kg. In one embodiment, the administration is intravenous administration and the amount that of the nanoconjugate composition that is administered is 7 mg/kg. In further embodiments, the nanoconjugate composition is administered daily, weekly or monthly. In some embodiments, a single administration is given per day. In further embodiments, 2, 3, 4, 5, 6, 7, 8, 9, 10 or more administrations of a nanoconjugate composition and/or therapeutic agent are given per day, or every other day, or every week, or every month.

Administration of a nanoconjugate composition with a therapeutic agent as described herein is contemplated, in various embodiments, will begin at the same time, or the therapeutic agent will be administered 1, 2, 3, 4, 5, 6, 7, 8, 9, 10 or more days after the nanoconjugate composition. In alternative embodiments, the therapeutic agent is administered 1, 2, 3, 4, 5, 6, 7, 8, 9, 10 or more days before the nanoconjugate composition is administered. Therapeutically and prophylactically effective amounts of a composition for a given situation may be determined by routine experimentation that is within the skill and judgment of the clinician. For example and without limitation, the amount of temozolamide that is administered is about 10 mg/kg, or about 20 mg/kg, or about 30 mg/kg, or about 40 mg/kg, or about 50 mg/kg or more.

In an embodiment, the pharmaceutical compositions may be formulated with pharmaceutically acceptable excipients such as carriers, solvents, stabilizers, adjuvants, and/or diluents, depending upon the particular mode of administration and dosage form. The pharmaceutical compositions should generally be formulated to achieve a physiologically compatible pH, and may range from a pH of about 3 to a pH of about 11, preferably about pH 3 to about pH 7, depending on the formulation and route of administration. In alternative embodiments, it may be preferred that the pH is adjusted to a range from about pH 5.0 to about pH 8. More particularly, the pharmaceutical compositions comprises in various aspects a therapeutically or prophylactically effective amount of at least one composition as described herein, together with one or more pharmaceutically acceptable excipients. As described herein, the pharmaceutical compositions may optionally comprise a combination of the compounds described herein.

The term "pharmaceutically acceptable excipient" refers to an excipient for administration of a pharmaceutical agent, such as the compounds described herein. The term refers to any pharmaceutical excipient that may be administered without undue toxicity.

Pharmaceutically acceptable excipients are determined in part by the particular composition being administered, as well as by the particular method used to administer the composition. Accordingly, there exists a wide variety of suitable formulations of pharmaceutical compositions (see, e.g., Remington's Pharmaceutical Sciences).

Suitable excipients may be carrier molecules that include large, slowly metabolized macromolecules such as proteins, polysaccharides, polylactic acids, polyglycolic acids, polymeric amino acids, amino acid copolymers, and inactive virus particles. Other exemplary excipients include antioxidants (e.g., ascorbic acid), chelating agents (e.g., EDTA), carbohydrates (e.g., dextrin, hydroxyalkylcellulose, and/or hydroxyalkylmethylcellulose), stearic acid, liquids (e.g., oils, water, saline, glycerol and/or ethanol) wetting or emulsifying agents, pH buffering substances, and the like.

Additionally, the pharmaceutical compositions may be in the form of a sterile injectable preparation, such as a sterile injectable aqueous emulsion or oleaginous suspension. This emulsion or suspension may be formulated by a person of ordinary skill in the art using suitable dispersing or wetting agents and suspending agents. The sterile injectable preparation may also be a sterile injectable solution or suspension in a non-toxic parenterally acceptable diluent or solvent, such as a solution in 1,2-propane-diol.

The sterile injectable preparation may also be prepared as a lyophilized powder. In addition, sterile fixed oils may be employed as a solvent or suspending medium. For this purpose any bland fixed oil may be employed including synthetic mono- or diglycerides. In addition, fatty acids (e.g., oleic acid) may likewise be used in the preparation of injectables.

Kits

Also provided are kits comprising a composition of the disclosure. In one embodiment, the kit comprises at least one container, the container holding at least one type of nanoconjugate as described herein comprising one or more biomolecules as described herein. In aspects of the disclosure wherein the biomolecule is a polynucleotide, it is contemplated that the polynucleotides that are part of the first type of nanoconjugate have one or more sequences complementary (or sufficiently complementary as disclosed herein) to one or more sequences of a first portion of a target polynucleotide. The container optionally includes one or more additional type of nanoconjugates comprising a polynucleotide with a sequence complementary to one or more sequence of a second portion of the target polynucleotide.

In another embodiment, the kit comprises at least two containers. The first container holds one or more nanoconjugates as disclosed herein comprising one or more polynucleotides as described herein which can associate with one or more portions of a target polynucleotide. The second container holds one or more nanoconjugates comprising one or more polynucleotides that can associate with one or more sequences of the same or a different portion of the target polynucleotide.

In another embodiment, the kits have polynucleotides and nanoparticles in separate containers, and the nanoconjugates are produced prior to use for a method described herein. In one aspect, the polynucleotides and/or the nanoparticles are functionalized so that the nanoconjugates can be produced. Alternatively, the polynucleotides and/or nanoparticles are provided in the kit without functional groups, in which case they must be functionalized prior to performing the assay.

In various aspects of the kits provided, polynucleotides include a label or the kit includes a label which can be attached to the polynucleotides. Alternatively, the kits include labeled nanoparticles or labels which can be attached to the nanoparticles. In each embodiment, the kit optionally includes instructions, each container contains a label, the kit itself includes a label, the kit optionally includes one or more non-specific polynucleotides (for use as controls).

EXAMPLES

Example 1

Figure 1B:
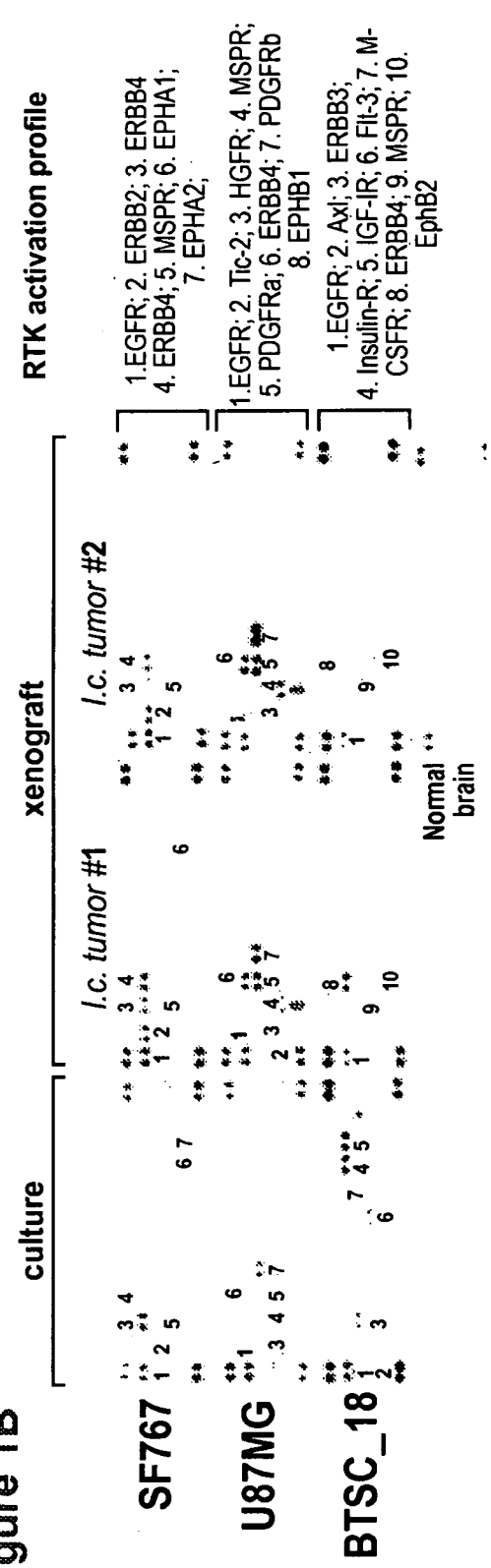

Bcl-2-like protein 12 (Bcl2L12) expression was assessed, and the compendium of activated receptor tyrosine kinases (RTKs) in human brain tumor stem cells (BTSCs) and derived orthotopic xenografts (FIG. 1). In line with previous studies in primary GBM tumor specimens [Stegh et al., Genes Dev. 21: 98-111 (2007)], robust expression of Bcl2L12 was identified in a majority of BTSCs tested and BTSC line 18 (huBTSC_18) with high Bcl2L12 expression was selected for initial functional studies (FIG. 1A). In addition, it was established that multiple RTKs are co-activated in glioma cells and in their corresponding orthotopic explants (FIG. 1B). Notably, the activation profile of RTKs in glioma cell lines in vitro is largely maintained in the explanted tumor—BTSC-derived grafts exhibit a more distinctive RTK signature when compared to the corresponding cultures, suggesting that the tumor microenvironment significantly impacts intratumoral RTK activation status of BTSC-initiated tumors.

Example 2

Figure 2:
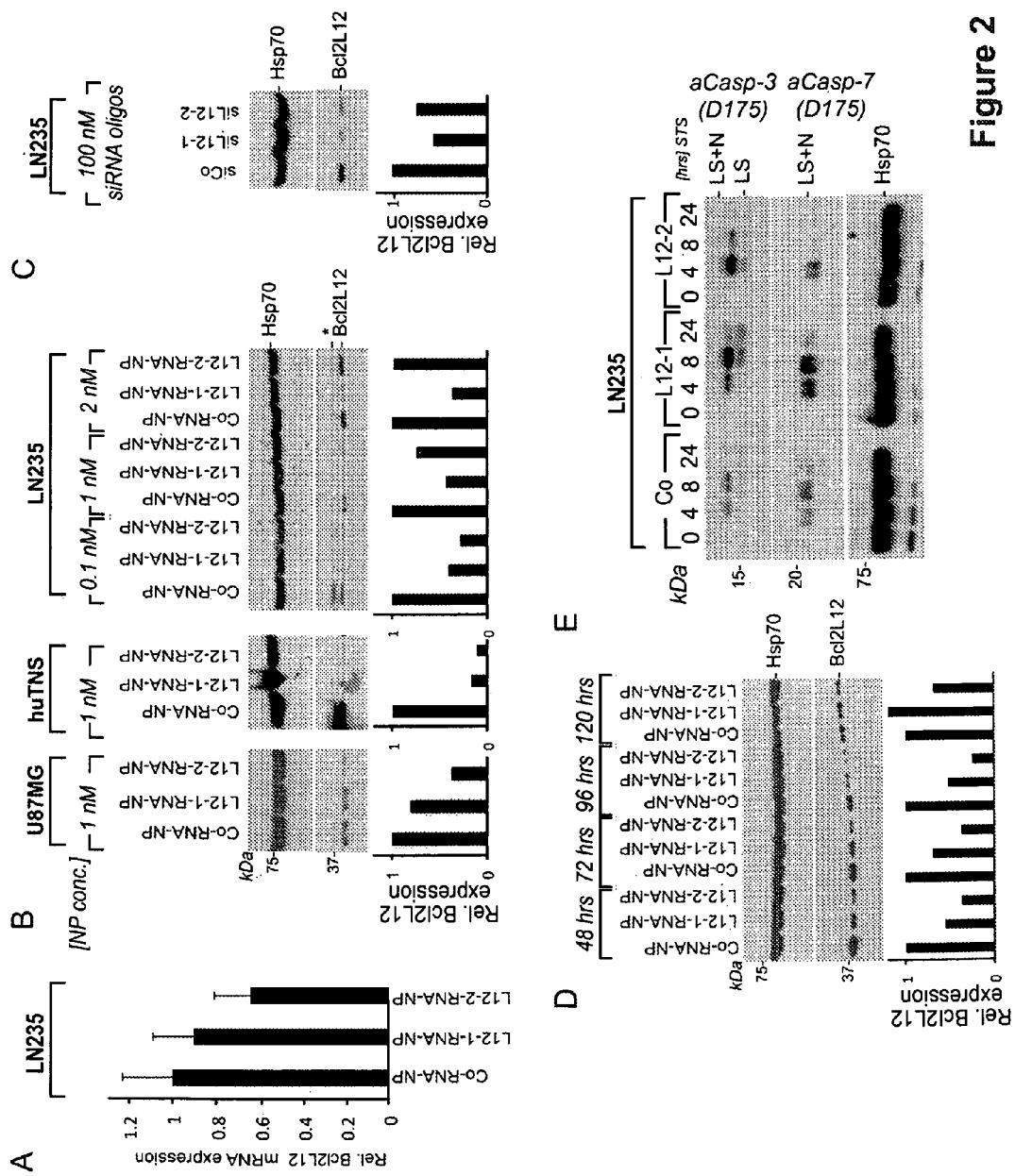
FIG. 2 shows that RNA-nanoconjugates effectively silence Bcl2L12 expression. (A and B) Glioma cell lines and huBTSC_18 were treated with indicated amounts of RNA-nanoconjugates (control (Co)/scrambled-RNA sequence-RNA-Au NPs—Co-RNA-nanoconjugate and Bcl2L12 targeting RNA-nanoconjugates—L12-1- and L12-2-RNA-nanoconjugates) and subjected to qRT-PCR (A) and western blot (B) analyses. The migration positions of Bcl2L12 and Hsp70 are indicated. *-labeled band represents post-translationally modified Bcl2L12. (C) Knockdown efficacies were compared to conventional lipoplex-delivered siRNAs. (D) For studies of knockdown persistence, LN235 cells were treated with L12-RNA-nanoconjugates (1 nM) for 5 days, and subjected to anti-Bcl2L12 western blot analyses. (E) RNA-nanoconjugate-mediated knockdown of Bcl2L12 results in enhanced caspase activation. Co-, L12-1- and L12-2-nanoconjugate-treated LN235 cells were treated with staurosporine (STS, 500 nM) for the indicated periods of time, lysed and subjected to western blot analyses for active caspases 3 and 7. The migration positions of the active subunits (large, LS; large and large+N peptide, LS+N) and Hsp70 (loading control) are indicated. Histograms quantify Bcl2L12 expression as assessed by densitometric analyses of corresponding western blots.

For therapeutic development, Bcl2L12 targeting RNAi gold nanoparticles (RNA-Au NP; nanoconjugates as described herein) were generated and screened for their ability to knockdown endogenous Bcl2L12 in glioma cell lines and huBTSC_18. Bcl2L12-RNA-nanoconjugates that were capable of reducing Bcl2L12 mRNA levels by 40% were identified (FIG. 2A) and Bcl2L12 protein abundance by 60-95% (FIG. 2B)—L12-1- and L12-2-RNA nanoconjugates. Subsequently, a nanoconjugate concentration (0.1 nM) to robustly neutralize Bcl2L12 protein expression in LN235 cells was determined (FIG. 2B), which compared to 100 nM of conventional, lipoplex-delivered siRNA oligonucleotides (FIG. 2C) required to achieve a similar effect, indicating that RNAi-functionalized nanoconjugates are significantly more effective in silencing gene expression than conventional methods. Importantly, similar, highly robust KD efficacies in BTSC and confirmed persistence of Bcl2L12 protein knockdown up to 5 days post nanoconjugate-treatment was established (FIG. 2D). Finally, and as shown with Bcl2L12-targeting siRNA and shRNAs [Stegh et al., Genes Dev. 21: 98-111 (2007)], nanoconjugate-mediated knockdown of Bcl2L12 resulted in enhanced effector caspase activation as evidenced by Western Blot analyses for active caspase-3 and -7 (FIG. 2E), confirming the functionality of nanoconjugate-driven Bcl2L12 knockdown.

Demonstration of knockdown of a second target: To further demonstrate the capacity of RNA-nanoconjugates to effectively silence gene expression in cells, the Bcl2L12 downstream effector aB-crystallin (CRYAB) was selected as a second prototypic gliomagenic target. aB-crystallin is transcriptionally induced by Bcl2L12 and functions to promote tumor cell migration/invasion and inhibit effector caspase-3 activation. FIG. 3 shows RNA-nanoconjugate-mediated knockdown of endogenous aB-crystallin (FIG. 3A; comparison of RNA-nanoconjugate (10 nM) and siRNA/lipoplex-mediated knockdown (100 nM)), reduced invasive properties (FIG. 3B), and enhanced caspase-3 activation of glioma cells upon aB-crystallin ablation (FIG. 3C). These studies demonstrated potent knockdown of two prototypic glioma oncoproteins with efficacies and impact on downstream signaling (i.e., caspase activation and cell invasion) similar to retrovirally/lipolex-delivered sh/siRNAs [Stegh et al., Genes Dev. 21: 98-111 (2007); Stegh et al., Proc Natl Acad Sci U.S.A. 105: 10703-8 (2008)].

Example 3

Figure 4A:
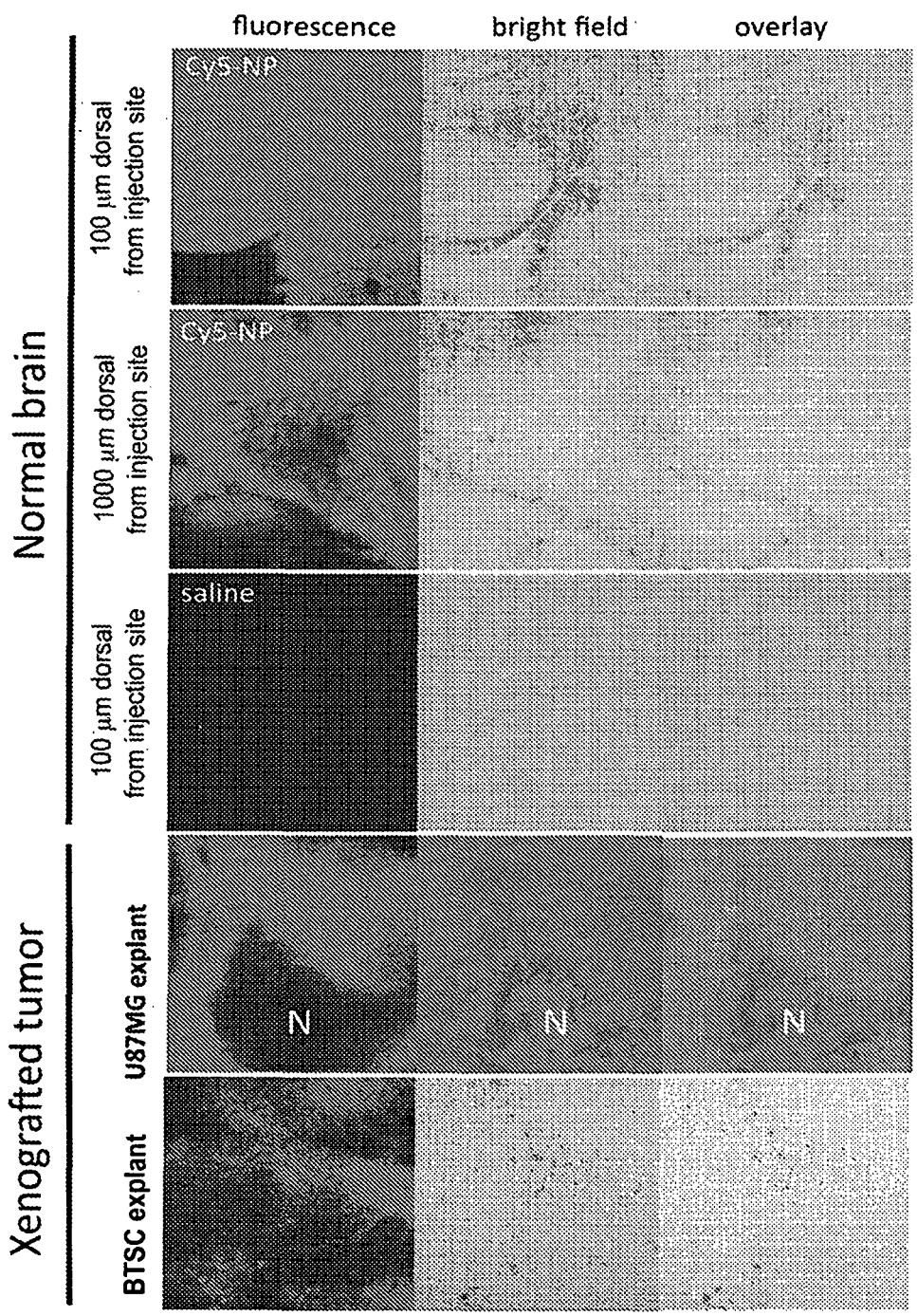
FIG. 4 shows intratumoral uptake of nanoconjugates as assessed by confocal immunofluorescence of Cy5-labeled Au-NPs (A), by ICP-MS (C) and by MRI (D) of locally delivered DNA-Gd(III)-nanoconjugates in normal brain and explant structures. (B) shows quantification of dispersion over time see using confocal IF images of serial coronal sections.
Figure 4B:
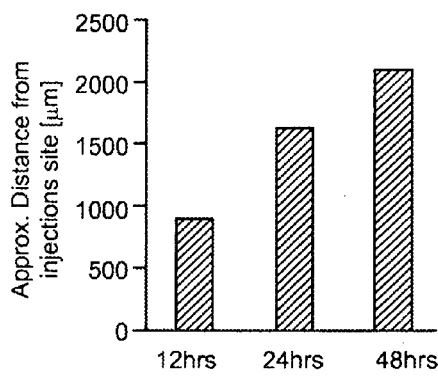
Figure 4C:
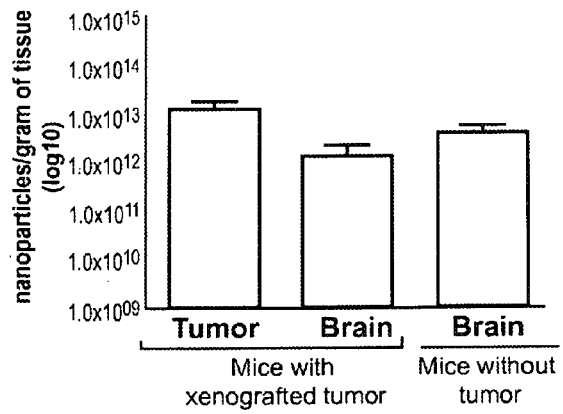

Having established broad pro-apoptotic activities of BCl2L12- and CRYAB-RNA-nanoconjugates in cell culture, the RNA-nanoconjugates functionality in orthotopic explant and genetically engineered mice was validated in vivo. These studies tested tumor regression in a genetically engineered glioma mouse model. Expanding on the known cellular and tissue uptake properties of these nanoconjugates, penetration of RNA-nanoconjugates into normal and cancerous intracranial tissues was documented and its uptake into BTSC xenografts was assessed (FIG. 4) upon IC injection. Following BTSC inoculation and Cy5-Au-NP administration, brains were dissected, and coronal sections were subjected to confocal fluorescence microscopy. FIG. 4A (lower panel) shows robust dispersion of RNA-nanoconjugates within the BTSC orthotopic tumor explant similar to U87MG grafts and FIG. 4B shows quantification of intracranial dispersion of fluorescence signal. Intracranial nanoconjugate uptake into tumor and non-tumor elements was verified by. Inductively Coupled Plasma Mass Spectrometry (ICP-MS; FIG. 4C), and also by magnetic resonance (MR) imaging using a multimodal, gadolinium (Gd(III))-enriched polyvalent DNA gold nanoparticle (DNA-Gd(III)-Au NPs) conjugate (FIG. 4D).

Figure 4D:
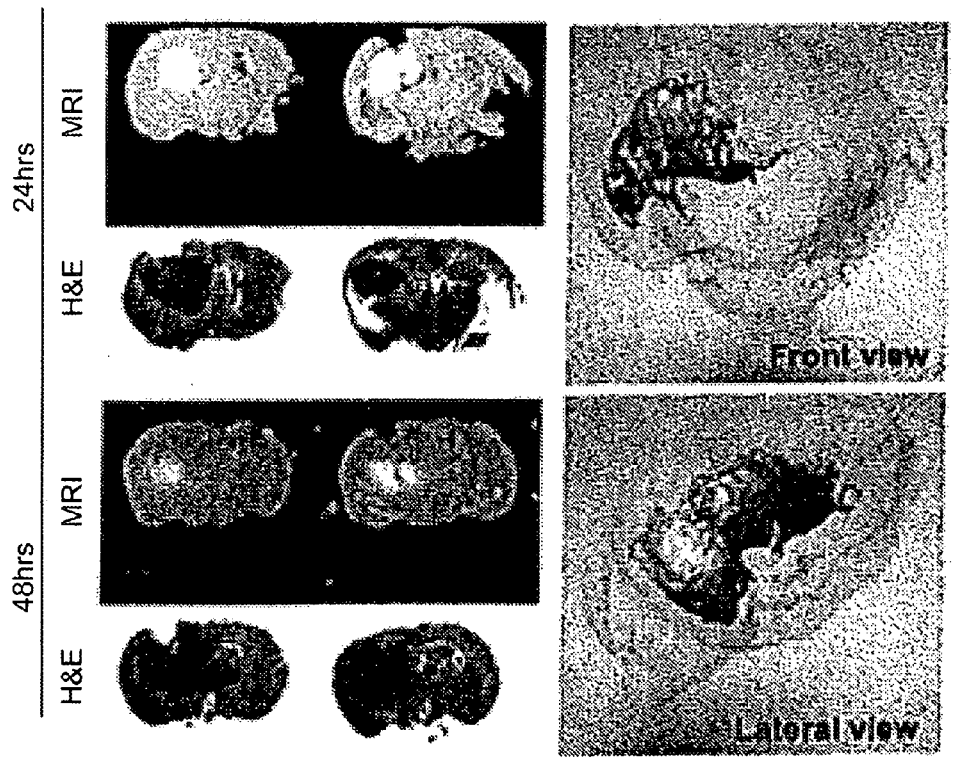
Figure 5A:
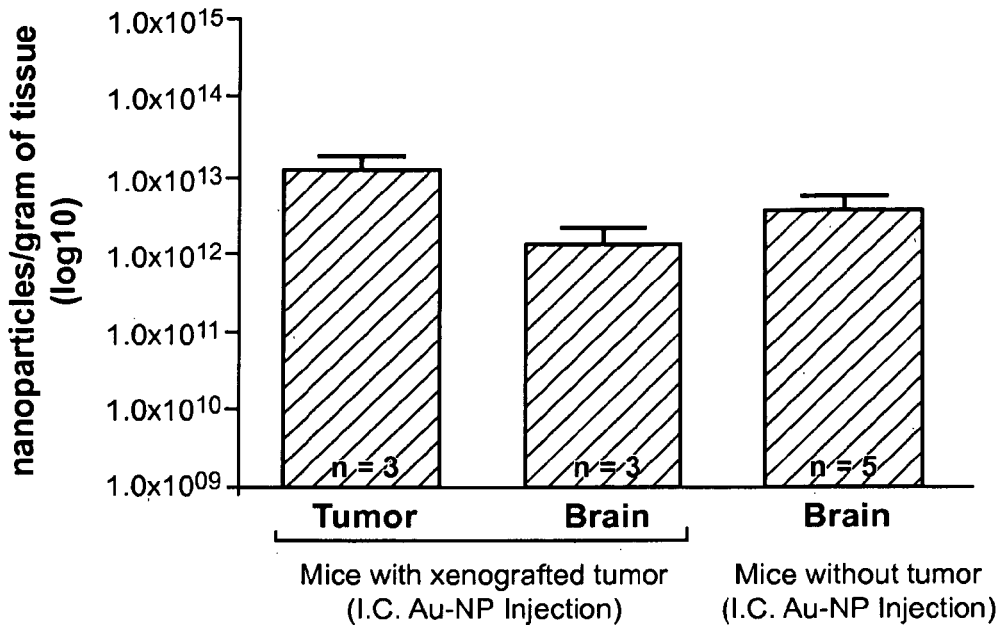
FIG. 5 shows intratumoral uptake of nanoconjugates—Intracranial versus Intravenous Administration as assessed by ICP-MS (A) Direct intracranial (I.C.) delivery of Co-RNA-nanoconjugates (5 µl, 300 nM). Nanoconjugates were locally delivered once and then the brain and tumor tissues were harvested 48 hours post administration. (B) Systemic intravenous (I.V.) injection of Co-RNA-nanoconjugates (100 µl, 300 nM). Four injections of nanoconjugates every 48 hours. The tissues were harvested 24 hours after the fourth injection.
Figure 5B:
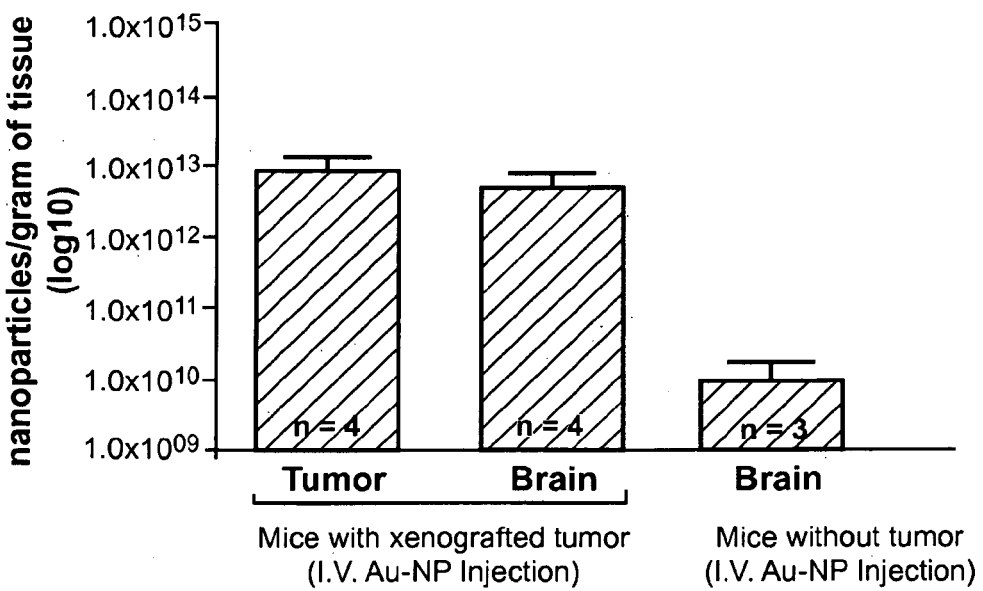

Predominant accumulation of DNA-Gd(III)-nanoconjugates within the intracranial U87MG-xenograft is evidenced by MR and corresponding hematoxylin and eosin (H&E) images (FIG. 4D, left panel). It is important to note that tumor cells and DNA-Gd(III)-nanoconjugates were injected in close proximity to Bregma; however, tumor formation and (intratumoral) accumulation of DNA-Gd(III)-nanoconjugates were most prominent in forebrain structures. This indicates that nanoconjugates migrated along the anteroposterior axis to selectively enrich tumor elements. Building on the extensive intratumoral dispersion of nanoconjugates (see FIG. 4D right panel for 3D reconstruction of MR images to quantifiably assess intracranial space occupied by DNA-Gd(III)-nanoconjugates), we compared the distribution of RNA-nanoconjugates in the mouse brain using intracranial (I.C.) injection directly to the brain with systematic intravenous (I.V.) injection via tail vein. A significantly higher amount of nanoconjugates were found in the xenografted tumor than in the rest of the brain, reconfirming enhanced intratumoral accumulation of the nanoconjugates (FIG. 5).

Figure 6:
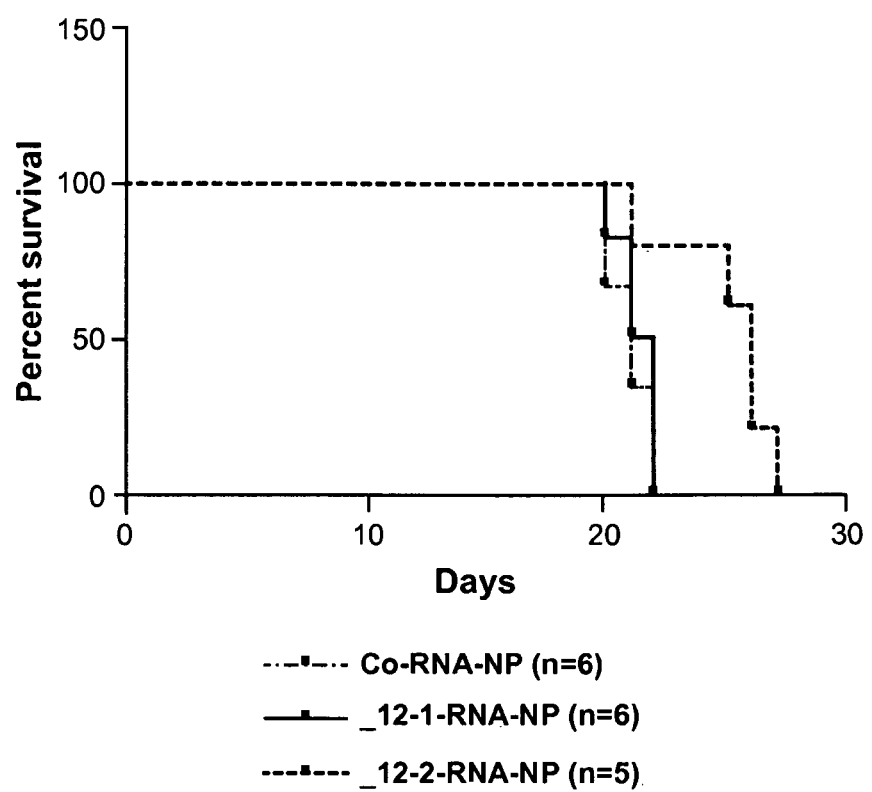
FIG. 6 shows the effects of RNA-nanoconjugates on survival of tumor mice. Co-, L12-1-, and L12-2-RNA-nanoconjugates were administered to mice via tail vein injection (I.V.). Each mouse received 5 injections (1.4 mg/kg RNA per injection totaling at 7 mg/kg treatment, approximately 150-200 µl of RNA-nanoconjugates at 500 nM). No difference in survival days was seen between Co- and L12-1-RNA nanoconjugate treatment groups (p=0.50). However, a significant difference was observed between Co- and L12-2-RNA-nanoconjugate treatment groups (p=0.01).

Finally, the impact of Bcl2L12-targeting RNA-nanoconjugates on tumor regression was tested in U87 glioma cell line xenogenic grafts in vivo using systemic injection. It was found that, in parallel with the in vitro findings (see FIG. 2B, left panel, U87MG), mice treated with L12-2-nanoconjugate showed significantly prolonged life span (p-value=0.01) explained by reduced activity of Bcl2L12 protein (FIG. 6). L12-1-nanoconjugates did not have a significant effect (p-value=0.50) on the life span and were not effective in knockdown of Bcl2L12 in vitro in U87 cell line.

The disclosed subject matter has been described with reference to various aspects, embodiments and techniques. It should be understood, however, that many variations and modifications may be made while remaining within the spirit and scope of the disclosed subject matter. All references cited herein are hereby incorporated by reference in their entireties, or to the extent that they provide relevant disclosure, as would be ascertained from context.

What is claimed is:

1. A method of treating a patient suffering from Glioblastoma multiforme, comprising administering to the patient a therapeutically effective amount of a composition comprising a functionalized nanoconjugate having a mass that is at least about 1 kilodalton, the nanoconjugate comprising a surface-attached polynucleotide having a sequence sufficiently complementary to a target polynucleotide to hybridize to and inhibit expression of the target polynucleotide, wherein the target polynucleotide is a Bcl-2 family member, and wherein the administration is not intracranial administration and the nanoconjugate does not comprise a targeting moiety.

2. A method of administering a composition comprising a functionalized nanoconjugate having a mass that is at least about 1 kilodalton to a patient, the method comprising administering to the patient a therapeutically effective amount of the composition;
   wherein the nanoconjugate comprises a surface-attached polynucleotide having a sequence sufficiently complementary to a target polynucleotide to hybridize to and inhibit expression of the target polynucleotide, wherein the target polynucleotide is a Bcl-2 family member, wherein the administration is not intracranial administration and the nanoconjugate does not comprise a targeting moiety, and wherein the patient suffers from Glioblastoma multiforme and is in need of a composition that is able to traverse the blood-brain barrier.

3. The method of claim 1 wherein the composition further comprises a therapeutic agent.

4. The method of claim 1 wherein the composition is administered only once.

5. The method of claim 1 wherein the composition is administered at a frequency of no greater than about once per week.

6. The method of claim 1 wherein the patient is a human.

7. The method of claim 1 wherein the Bcl-2 family member is Bcl2L12.

8. The method of claim 1 wherein the nanoconjugate comprises a nanoparticle that is metallic.

9. The method of claim 2 wherein the nanoconjugate comprises a nanoparticle that is metallic.

10. The method of claim 8 wherein the nanoparticle is a gold nanoparticle.

11. The method of claim 9 wherein the nanoparticle is a gold nanoparticle.

12. The method of claim 1 wherein the administering is transdermal administering.

13. The method of claim 2 wherein the administering is transdermal administering.

14. The method of claim 1 wherein the polynucleotide is DNA or RNA.

15. The method of claim 14 wherein the polynucleotide is small interfering RNA (siRNA).

16. The method of claim 2 wherein the polynucleotide is DNA or RNA.

17. The method of claim 16 wherein the polynucleotide is small interfering RNA (siRNA).

18. The method of claim 1 wherein the nanoconjugate comprises a nanoparticle that is hollow.

19. The method of claim 2 wherein the nanoconjugate comprises a nanoparticle that is hollow.

20. The method of claim 1 wherein the nanoconjugate comprises a nanoparticle that is from about 5 nanometers (nm) to about 150 nm in mean diameter.

21. The method of claim 2 wherein the nanoconjugate comprises a nanoparticle that is from about 5 nanometers (nm) to about 150 nm in mean diameter.

22. The method of claim 1 wherein the polynucleotide is covalently associated with the nanoconjugate.

23. The method of claim 2 wherein the polynucleotide is covalently associated with the nanoconjugate.

24. The method of claim 1 wherein the polynucleotide is present on the surface of the nanoconjugate at a surface density of at least 0.3 pmol/cm$^2$.

25. The method of claim 2 wherein the polynucleotide is present on the surface of the nanoconjugate at a surface density of at least 0.3 pmol/cm$^2$.

26. The method of claim 1 wherein the polynucleotide is present on the surface of the nanoconjugate at a surface density of at least 2 pmol/cm$^2$.

27. The method of claim 2 wherein the polynucleotide is present on the surface of the nanoconjugate at a surface density of at least 2 pmol/cm$^2$.

28. The method of claim 1 wherein the polynucleotide is present on the surface of the nanoconjugate at a surface density of about 15 pmol/cm$^2$.

29. The method of claim 2 wherein the polynucleotide is present on the surface of the nanoconjugate at a surface density of about 15 pmol/cm$^2$.

30. The method of claim 3 wherein the therapeutic agent is temozolamide, brain-derived neurotrophic factor (BDNF), nerve growth factor (NGF), neurotrophin-4/5, a fibroblast growth factor (FGF), neurotrophin (NT)-3, erythropoietin (EPO), hepatocyte growth factor (HGF), epidermal growth factor (EGF), transforming growth factor (TGF)-α, TGF-β, vascular endothelial growth factor (VEGF), interleukin-1 receptor antagonist (IL-1ra), ciliary neurotrophic factor (CNTF), glial-derived neurotrophic factor (GDNF), neurturin, platelet-derived growth factor (PDGF), heregulin, neuregulin, artemin, persephin, an interleukin, granulocyte-colony stimulating factor (CSF), granulocyte-macrophage-CSF, cardiotrophin-1, hedgehog, leukemia inhibitory factor (LIF), midkine, pleiotrophin, a bone morphogenetic protein (BMP), netrin, saposin, semaphorin, or stem cell factor (SCF).

31. The method of claim 1 wherein the nanoconjugate has a mass that is about 2, about 3, about 5, about 10, about 20, about 30, about 40, about 50, about 60, about 70, about 80, about 90, about 100, about 200, about 500, about 700, about 900 or more kilodaltons.

32. The method of claim 2 wherein the nanoconjugate has a mass that is about 2, about 3, about 5, about 10, about 20, about 30, about 40, about 50, about 60, about 70, about 80, about 90, about 100, about 200, about 500, about 700, about 900 or more kilodaltons.

33. The method of claim 1, further comprising administering a therapeutic agent to the patient.

34. The method of claim 1 wherein the nanoconjugate comprises a nanoparticle that is from about 30 nm to about 100 nm.

35. The method of claim 1 wherein the nanoconjugate comprises a nanoparticle that is from about 40 nm to about 80 nm in mean diameter.

36. The method of claim 2 wherein the nanoconjugate comprises a nanoparticle that is from about 30 nm to about 100 nm.

37. The method of claim 2 wherein the nanoconjugate comprises a nanoparticle that is from about 40 nm to about 80 nm in mean diameter.

38. The method of claim 2 wherein the Bcl-2 family member is Bcl2L12.

* * * * *